US012642838B2

(12) United States Patent
Chong et al.

(10) Patent No.: US 12,642,838 B2
(45) Date of Patent: Jun. 2, 2026

(54) METHOD OF MODULATING SENSITIVITY TO TYROSINE KINASE INHIBITOR

(71) Applicant: SINGAPORE HEALTH SERVICES PTE LTD, Singapore (SG)

(72) Inventors: Fui Teen Chong, Singapore (SG); Dorival Mendes Rodrigues-Junior, Singapore (SG); Narayanan Gopalakrishna Iyer, Singapore (SG); Hui Sun Leong, Singapore (SG); Daniel Shao-Weng Tan, Singapore (SG); Darren Shen Yon Toh, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 442 days.

(21) Appl. No.: 18/021,705

(22) PCT Filed: Aug. 25, 2021

(86) PCT No.: PCT/SG2021/050500
§ 371 (c)(1),
(2) Date: Feb. 16, 2023

(87) PCT Pub. No.: WO2022/045976
PCT Pub. Date: Mar. 3, 2022

(65) Prior Publication Data
US 2024/0024419 A1      Jan. 25, 2024

(30) Foreign Application Priority Data
Aug. 25, 2020    (SG) ............................ 10202008169Q

(51) Int. Cl.
| | |
|---|---|
| *A61K 38/17* | (2006.01) |
| *A61K 31/506* | (2006.01) |
| *A61K 31/517* | (2006.01) |
| *A61K 31/5377* | (2006.01) |
| *A61P 35/00* | (2006.01) |

(52) U.S. Cl.
CPC .......... *A61K 38/179* (2013.01); *A61K 31/506* (2013.01); *A61K 31/517* (2013.01); *A61K 31/5377* (2013.01); *A61P 35/00* (2018.01)

(58) Field of Classification Search
CPC .. A61K 38/179; A61K 31/506; A61K 31/517; A61K 31/5377; A61P 35/00
See application file for complete search history.

(56) References Cited

U.S. PATENT DOCUMENTS

2017/0035797 A1      2/2017  Bader et al.

FOREIGN PATENT DOCUMENTS

| | | | | |
|---|---|---|---|---|
| WO | WO-2017209697 A1 | * | 12/2017 | ............... C12Q 1/68 |
| WO | WO-2019070856 A1 | * | 4/2019 | ............. C07K 14/71 |

OTHER PUBLICATIONS

Google Search; EGFR isoform D (Year: 2025).*
Tan et al.; Long noncoding RNA EGFR-AS1 mediates epidermal growth factor receptor addiction and modulates treatment response in squamous cell carcinoma; Springer Nature; Nature Medicine, vol. 23, No. 10, 2017, 1167-1175 (Year: 2017).*
Google Search; what produces EGFR isoform D (Year: 2025).*
Tan et al.; Long noncoding RNA EGFR-AS1 mediates epidermal growth factor receptor addiction and modulates treatment response in squamous cell carcinoma; Springer Nature; Nature Medicine, vol. 23, No. 10, 2017, 1167-1175; Supplementary Information (Year: 2017).*
Google Search; do exosomes produce EGFR isoform D (Year: 2025).*
Baron, A., et al., "Clinical implementation of soluble EGFR (sEGFR) as a theragnostic serum biomarker of breast, lung and ovarian cancer", IDrugs, 2009, vol. 12, No. 5, pp. 302-308.
Michmerhuizen, N., et al., "Rationale for Using Irreversible Epidermal Growth Factor Receptor Inhibitors in Combination with Phosphatidylinositol 3-Kinase Inhibitors for Advanced Head and Neck Squamous Cell Carcinoma", Molecular Pharmacology, 2019, vol. 95, No. 5, pp. 528-536.
Sanderson, M., et al., "Generation of Novel, Secreted Epidermal Growth Factor Receptor (EGFR/ErbB1) Isoforms Via Metalloprotease-Dependent Ectodomain Shedding and Exosome Secretion", Journal of Cellular Biochemistry, 2008, vol. 103, No. 6 pp. 1783-1797.

* cited by examiner

*Primary Examiner* — Robert A Wax
*Assistant Examiner* — John W Lippert, III
(74) *Attorney, Agent, or Firm* — ArentFox Schiff LLP; Daniel W. Clarke

(57) ABSTRACT

The invention relates to methods of increasing sensitivity of an epidermal growth factor receptor (EGFR)-related cancer to EGFR tyrosine kinase inhibitor (TKI) comprising administering a therapeutically effective amount of EGFR isoform D to a subject in need thereof. The invention also relates to methods of treating a subject suffering from an EGFR-related cancer comprising administering to the subject an effective amount of EGFR isoform D and a TKI. In one embodiment, the EGFR-related cancer is head and neck squamous cell carcinoma (HNSCC).

13 Claims, 79 Drawing Sheets

Specification includes a Sequence Listing.

A

B

- No EV
- 1uM PS2
- 293T pBob EV
- 293T pBob EV + 1uM PS2
- 293T pBob-IsoD EV
- 293T pBob-IsoD EV + 1uM PS2

% Survival

Log[Gefitinib], μM

NCC-HN120M

NCC-HN120M

NCC-HN1

NCC-HN1

NCC-HN120M

NCC-HN120M

FIG. 11G

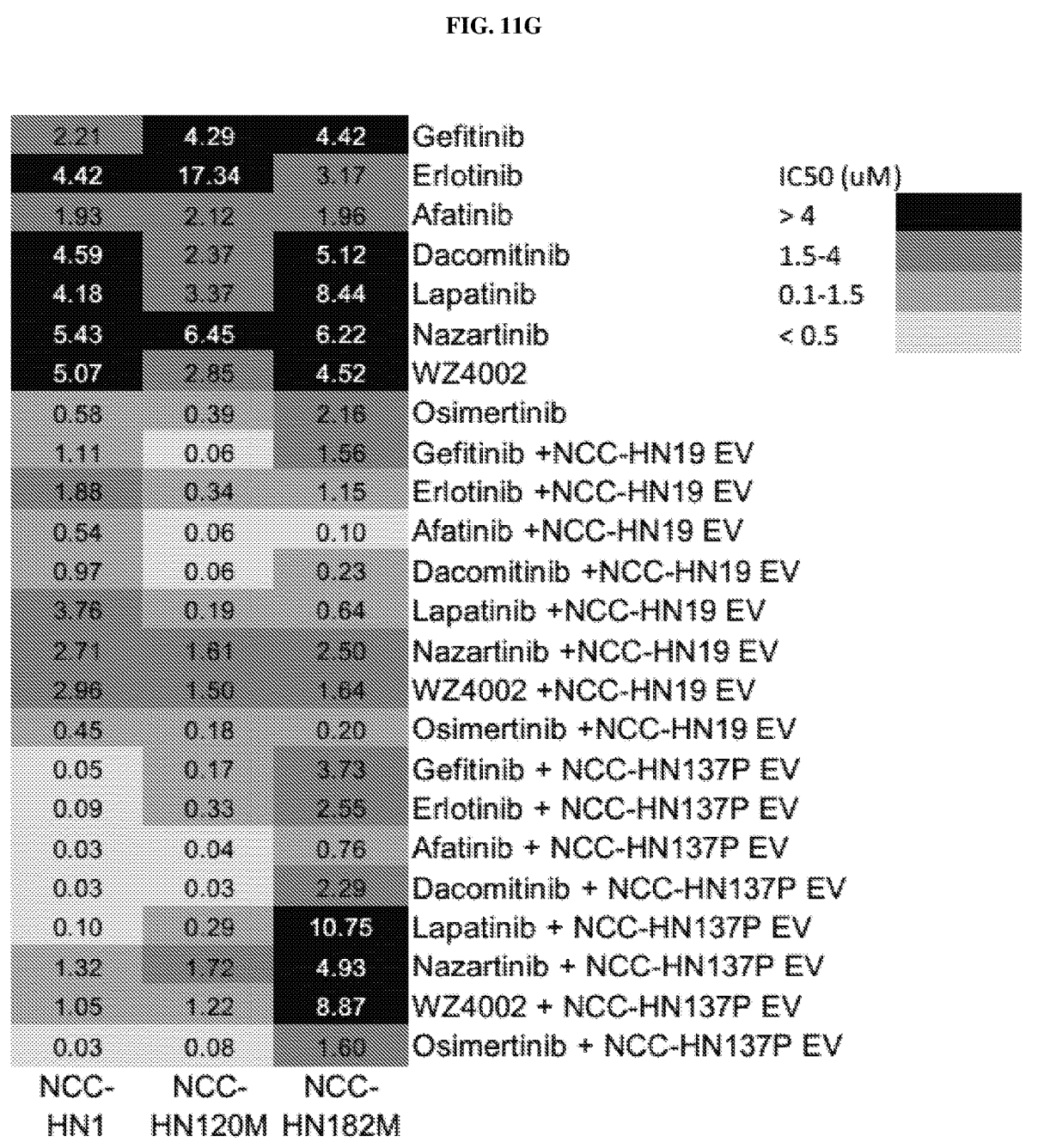

| NCC-HN1 | NCC-HN120M | NCC-HN182M | |
|---|---|---|---|
| 2.?1 | 4.29 | 4.42 | Gefitinib |
| 4.42 | 17.34 | 3.?7 | Erlotinib |
| 1.9? | 2.12 | 1.?6 | Afatinib |
| 4.59 | 2.?7 | 5.12 | Dacomitinib |
| 4.18 | 3.?7 | 8.44 | Lapatinib |
| 5.43 | 6.45 | 6.22 | Nazartinib |
| 5.07 | 2.?5 | 4.52 | WZ4002 |
| 0.58 | 0.39 | 2.1? | Osimertinib |
| 1.11 | 0.06 | 1.?6 | Gefitinib +NCC-HN19 EV |
| 1.8? | 0.34 | 1.15 | Erlotinib +NCC-HN19 EV |
| 0.54 | 0.06 | 0.10 | Afatinib +NCC-HN19 EV |
| 0.97 | 0.06 | 0.23 | Dacomitinib +NCC-HN19 EV |
| 3.76 | 0.19 | 0.64 | Lapatinib +NCC-HN19 EV |
| 2.71 | 1.?1 | 2.?0 | Nazartinib +NCC-HN19 EV |
| 2.?6 | 1.?0 | 1.?4 | WZ4002 +NCC-HN19 EV |
| 0.45 | 0.18 | 0.20 | Osimertinib +NCC-HN19 EV |
| 0.05 | 0.17 | 3.?3 | Gefitinib + NCC-HN137P EV |
| 0.09 | 0.33 | 2.?5 | Erlotinib + NCC-HN137P EV |
| 0.03 | 0.04 | 0.76 | Afatinib + NCC-HN137P EV |
| 0.03 | 0.03 | 2.?9 | Dacomitinib + NCC-HN137P EV |
| 0.10 | 0.29 | 10.75 | Lapatinib + NCC-HN137P EV |
| 1.32 | 1.7? | 4.93 | Nazartinib + NCC-HN137P EV |
| 1.05 | 1.22 | 8.87 | WZ4002 + NCC-HN137P EV |
| 0.03 | 0.08 | 1.?0 | Osimertinib + NCC-HN137P EV |

IC50 (uM)
> 4
1.5-4
0.1-1.5
< 0.5

NCC-HN1

NCC-HN120M

NCC-HN120M

NCC-HN120M

NCC-HN1

NCC-HN120M

NCC-HN182M

NCC-HN1

NCC-HN120M

NCC-HN182M

NCC-HN1

NCC-HN120M

NCC-HN182M

NCC-HN1

NCC-HN120M

NCC-HN182M

NCC-HN1

NCC-HN120M

NCC-HN182M

FIG. 19A CONTINUED    Afatinib
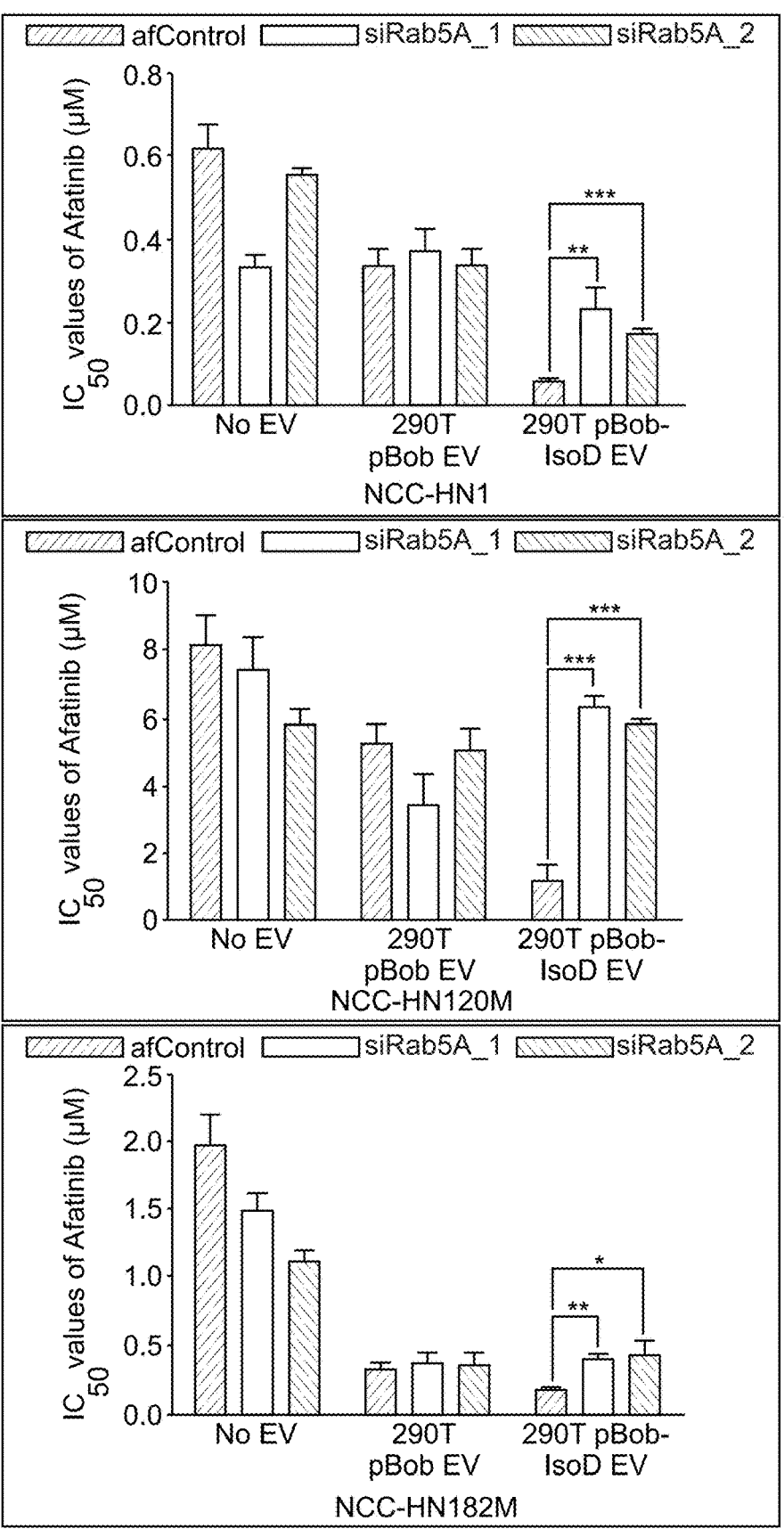

Dacomitinib

Gefitinib

NCC-HN1

NCC-HN120M

NCC-HN182M

Dacomitinib

NCC-HN1

NCC-HN182M

Afatinib

Dacomitinib

IP using EGFR Isoform D Antibody

IP using EGFR Isoform A Antibody

NCC-HN1 (IP)

1h

NC    pBob    IsoD    IgG (293T EV)

EGFR Iso D →

IsoD Monoclonal Ab

EGFR Iso A →

EGFR C-Ter

EGFR Iso A →

EGFR Iso D →

EGFR N-Ter

NCC-HN1 (Lysate)

1h

NC    pBob    IsoD    IgG (293T EV)

EGFR Iso A →

EGFR C-Ter

GAPDH

A.

Purified Isoform D protein
produce in Bacteria

B.

Purified Isoform D protein produce in HEK293F cells

METHOD OF MODULATING SENSITIVITY TO TYROSINE KINASE INHIBITOR

CROSS-REFERENCE TO RELATED APPLICATIONS

This application is a National Stage Application, filed under 35 U.S.C. § 371 of International Application No. PCT/SG2021/050500, filed Aug. 25, 2021, which claims the benefit of priority of under 35 U.S.C. § 119 to SG provisional application no. 10202008169Q, filed on 25 Aug. 2020, the contents of each of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Aug. 25, 2021 is named 72760PCT-seql-000001.txt and is 2 KB in size.

FIELD OF THE INVENTION

The present invention relates generally to the field of molecular biology. In particular, the present invention relates to the use of compounds modulating response for compounds used in treating cancer.

BACKGROUND OF THE INVENTION

Squamous cell cancers (SCCs) represent one of the most common lethal cancers worldwide, with a tendency to recur, metastasize, and result in death. Head and neck squamous cell cancers (HNSCCs) are prototypical of this group of cancers. Despite evidence that a significant proportion of squamous cell cancers is dependent on epidermal growth factor receptor (EGFR)-signalling, only moderate success has been achieved with targeting this pathway with monoclonal antibodies and/or tyrosine kinase inhibitors (TKI).

Thus, there is an unmet need to providing methods which augment tumour response to tyrosine kinase inhibitor therapy.

SUMMARY

In one example, the present disclosure refers to a method of increasing sensitivity of an EGFR-related cancer to epidermal growth factor receptor (EGFR) tyrosine kinase inhibitor (TKI) comprising administering a therapeutically effective amount of epidermal growth factor receptor isoform D to a subject in need thereof.

In another example, there is disclosed a method of treating a subject suffering from an EGFR-related cancer, comprising administering to the subject an effective amount of epidermal growth factor receptor isoform D; and administering to the subject an effective amount of a tyrosine kinase inhibitor used to treat the EGFR-related cancer.

BRIEF DESCRIPTION OF THE DRAWINGS

The invention will be better understood with reference to the detailed description when considered in conjunction with the non-limiting examples and the accompanying drawings, in which:

FIG. 11 shows viability of different cell lines when co-treated with extracellular vesicles (EVs) from NCC-HN19, NCC-HN137P and 293T in combination with different tyrosine kinase inhibitors. FIG. 11G shows a heatmap (as a summary) of NCC-HN1, NCC-HN120M and NCC-HN182M cells co-treated with NCC-HN19EV and NCC-HN137EV and eight tyrosine kinase inhibitors. This heatmap shows the $IC_{50}$ values for NCC-HN1, NCC-HN120M and NCC-HN182M cells treated without exosome (TKI only) or with exosome from NCC-HN19 cells (NCC-HN19 EV) or with exosome from NCC-HN137P cells (NC-HN137P EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).

FIG. 12 shows data indicating whether increasing amount of exosomal EGFR isoform D can modulate the sensitivity to tyrosine kinase inhibitor (TKI) treatment.

FIG. 18 shows immunofluorescence assay of NCC-HN1 cells treated with PitStop2 or without (untreated) 8 hours post EV addition is shown. EEA1 use to mark early endosome compartment. This data indicates that inhibition of clathrin-mediated endocytosis prevents the internalisation of EGFR isoform D into the cells.

FIG. 19 shows results indicating that a knock-down of Rab5A in target cells reduces the sensitizing effect conferred by isoform D exosomes (EV).

FIG. 20 shows results indicating that a knock-down of Rab7A in target cells reduces the sensitizing effect conferred by isoform D EV.

FIG. 21 shows data indicating that a knock-down of EEA1 in target cells reduces the sensitizing effect conferred by isoform D exosomes (EV).

FIG. 17-21** shows that the disruption of the endocytic processes in the treated cells will reduce the sensitising effect of isoform D containing EV. This data highlighted the role played by the endocytic process for the sensitising effect of isoform D EV.

FIG. 24 shows data indicating that exosomal EGFR isoform D interacts with EGFR isoform A on target cells, as illustrated by Western blot analysis of an immunoprecipitation assay (IP). FIG. 24A shows results of using EGFR isoform D antibody for precipitation, while

DEFINITIONS

Figure 1:
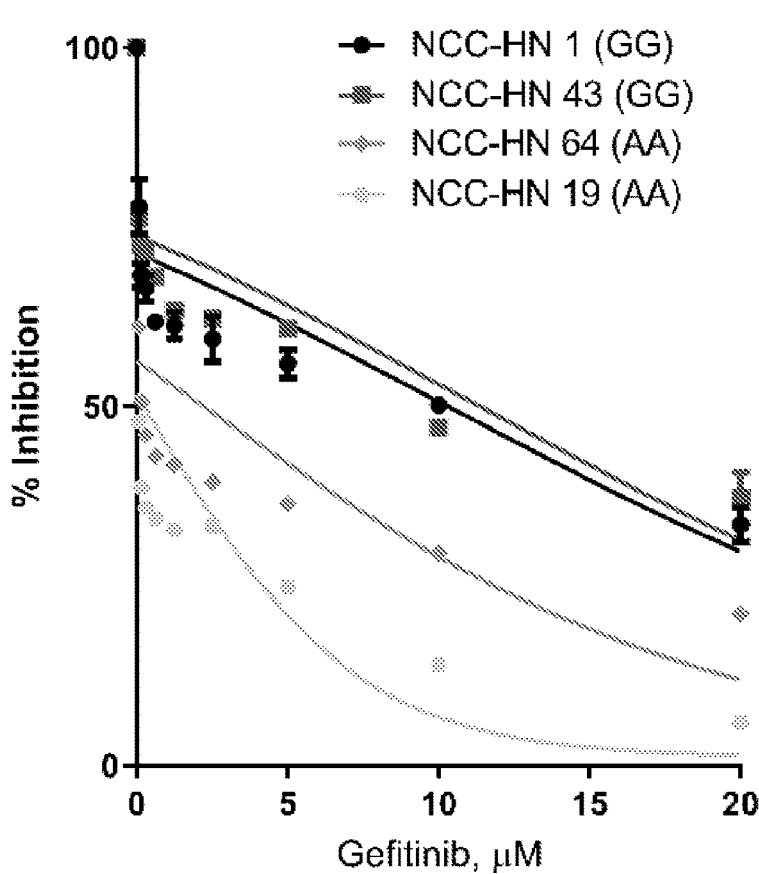
FIG. 1 shows data illustrating (A) a response to gefitinib and (B) relative EGFR isoform D to isoform A mRNA ratios for EGFR Q787Q G/G (WT) and A/A cell lines. This shows that cell lines with the EGFR single nucleotide polymorphism (SNP) Q787Q A/A are sensitive to epidermal growth factor receptor tyrosine kinase inhibitors (EGFR TKIs).
Figure 1:
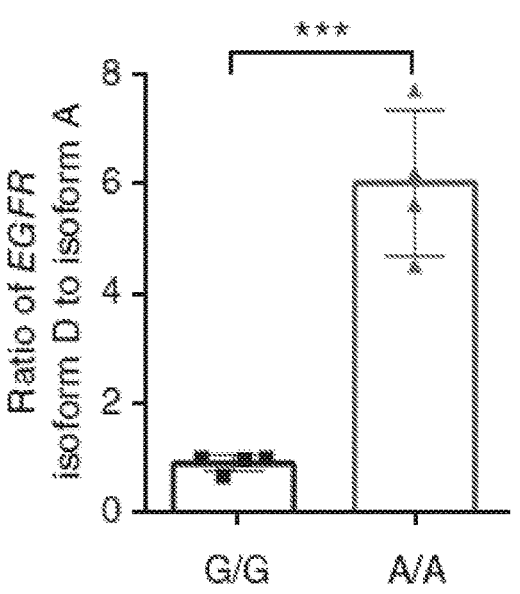

As used herein, the term "EGFR" refers to "epidermal growth factor receptor", a transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). In many cancer types, mutations affecting EGFR expression or activity could result in cancer. Deficient signalling of the EGFR and other receptor tyrosine kinases in humans is associated with diseases such as Alzheimer's, while over-expression is associated with the development of a wide variety of tumours. Interruption of EGFR signalling, either by blocking EGFR binding sites on the extracellular domain of the receptor, or by inhibiting intracellular tyrosine kinase activity, can prevent the growth of EGFR-expressing tumours and improve the patient's condition.

As used herein, the term "EGFR-AS1" refers to a 2.8 kb sequence that corresponds to intron and exon 20 expressed by the EGFR gene.

As used herein, the term "isoform" or "protein isoform" refers to the different forms of a protein encoded from one and the same gene. These proteins may be different in both structure and composition, whereby these differences are regulated by alternative splicing of mRNA, variable promoter usage, or other post-transcriptional modification of a single gene. This alternative splicing has been shown to have a large impact in proteome diversity. The specificity of produced proteins is derived by protein structure/function, development stage and even the cell type. Isoform formation becomes more complicated when a protein has multiple subunits and each subunit has multiple isoforms.

As used herein, the term "tyrosine kinase" refers to an enzyme that can transfer a phosphate group from adenosine triphosphate (ATP) to a target protein in a cell. It functions as an "on" or "off" switch in many cellular functions. Tyrosine kinases are a subclass of protein kinase, of which the tyrosine kinase is named as such because it transfers the phosphate group from ATP to a tyrosine residue within the target protein. There are two known families of tyrosine kinase, namely receptor tyrosine kinase (RTK) and non-receptor or cytoplasmic tyrosine kinase, whereby receptor tyrosine kinases comprise a transmembrane domain and one or more extracellular ligand-binding domains. Cytoplasmic tyrosine kinases do not possess such a transmembrane domain or any extracellular ligand-binding domains.

In view of the above, the term "TKI" refers to tyrosine kinase inhibitors, which are compounds or pharmaceutical drugs that inhibit tyrosine kinases. Tyrosine kinases are enzymes responsible for the activation of many proteins by signal transduction cascades. The proteins are activated by adding a phosphate group to the protein (phosphorylation), a step that TKIs inhibit. TKIs are typically used as anticancer drugs. First generation tyrosine kinase inhibitors work by blocking the activation of downstream signalling induced by EGFR through binding to the ATP-binding sites, and usually comprise reversible inhibitors. Second generation tyrosine kinase inhibitors are more potent drugs and have expanded inhibition against a broad spectrum of mutations resistant to gefitinib/erlotinib; these are mainly, but not limited to, ErbB family blockers; and usually comprise irreversible inhibitors. Third generation tyrosine kinase inhibitors with pyrimidine core structures were created to target the T790M clone with maintained activity against the original exon19del and L858R mutations. Binding at the C797 locus and having selectivity against the T790M mutation, third-generation inhibitors have had responses for patients with T790M resistance after first-generation inhibitors.

As used herein, the term "exosomal" or "exosomes" refers to membrane-bound extracellular vesicles (EVs) that are produced in the endosomal compartment of most eukaryotic cells. The multivesicular body (MVB) is a specialised subset of endosomes that contain membrane-bound intraluminal vesicles (ILVs) that forms as a result of the invagination and budding of the limiting membrane of the endosome into the endosomal lumen. If the MVB fuses with the cell surface (the plasma membrane), these ILVs are released as exosomes. Exosomes can contain different cargoes, such as, but not limited to, proteins, lipids, and nucleic acids. These cargoes are specifically sorted and packaged into exosomes. The contents packaged into exosomes are cell type-specific, and also influenced by cellular conditions. For example, exosomal microRNAs (exomiRs) and proteins are sorted and packaged in exosomes.

In multicellular organisms, exosomes and other extracellular vesicles (EVs) are present in tissues and can also be found in biological fluids including blood, urine, and cerebrospinal fluid. They are also released in vitro by cultured cells into their growth medium. Since the size of exosomes is limited by that of the parent MVB, exosomes are generally thought to be smaller than most other extracellular vesicles, from about 30 to 150 nanometres (nm) in diameter: around the same size as many lipoproteins but much smaller than cells. In the context of the present disclosure, the terms "exosome" and "extracellular vesicles" are used interchangeably.

As used herein, the term "SNP" refers to "single nucleotide polymorphism", which is a DNA sequence variation that occurs when a single nucleotide (A, T, C, or G) in the genome sequence is altered or differs between members of a biological species or paired chromosomes in a human. Thus, as used herein, a SNP is any polymorphism characterized by a different single nucleotide at a particular physical position in at least one allele. Each individual in a given population has many single nucleotide polymorphisms that together create a unique DNA pattern for that individual.

As used herein, the term "alternative splicing" refers to a regulated process during gene expression that results in a single gene coding for multiple proteins. In this process, particular exons (that is, parts of the genetic code that become part of the mature RNA) of a gene may be included within or excluded from the final, processed messenger RNA (mRNA) produced from that gene. The excluded sequences are termed introns, from intragenic region, that is a region inside a gene. The term intron and exon refers to both the DNA sequence within a gene and the corresponding sequence in RNA transcripts Consequently, the proteins translated from alternatively spliced mRNAs will contain differences in their amino acid sequence and, often, in their biological functions.

As used herein, the term "polymorphism" refers to the existence of two or more distinctly different forms (morphs) within, for example an animal species. In genetics, a (genetic) polymorphism is used to describe essentially interindividual, functionally silent differences in DNA sequence that make each human genome unique. In other words, a genetic polymorphism is the occurrence, in the same population, of multiple discrete allelic states, of which at least two have high frequency. Conventionally, the high frequency is defined as being of 1% or more of the population in question. One example of a genetic polymorphism is a single nucleotide polymorphism (SNP), which is a variation in a single nucleotide that occurs at a specific position in the genome, where each variation is present to some appreciable degree within a population (for example, more than 1% of said population).

DETAILED DESCRIPTION

In head and neck squamous cell cancers, cohort-based sequencing studies have failed to demonstrate activating mutations in exon 18 to 21 of epidermal growth factor receptor (EGFR). In addition, these studies have also failed to identify or demonstrate known predictors of response such as EGFR amplification, while a subset of these tumours will respond to tyrosine kinase inhibitor therapy. This shows that these tumours remain EGFR-driven through non-genomic mechanisms.

Disclosed herein is a biomarker suite identified from genomic and RNA alterations, which culminate in modulating the effects of epidermal growth factor receptor (EGFR)

inhibition. This information was obtained by studying patients with exceptional response to epidermal growth factor receptor (EGFR) tyrosine kinase inhibitors (TKIs). This data indicates that in a minority of patients, an epidermal growth factor receptor single nucleotide polymorphism (SNP) results in a specific long non-coding RNA (lncRNA), EGFR-AS1, which alters epidermal growth factor receptor splicing, thereby sensitising tumours to commonly used epidermal growth factor receptor tyrosine kinase inhibitors. Without being bound by theory, this effect is thought to be mediated through modulating intrinsic cellular levels of epidermal growth factor receptor (EGFR) isoform D. Experimental data shows that the modulation of intrinsic cellular levels of epidermal growth factor receptor isoform D was sufficient to sensitise tumour cells to these drugs in vitro/ex vivo (in patient-derived cells in culture, patient-derived xenograft models, and the like), and have been observed in vivo (in clinical cases).

Also disclosed herein is the use of EGFR isoform D, for example exosomal EGFR isoform D, as a co-treatment or co-therapy to augment or modulate the effect of epidermal growth factor receptor-tyrosine kinase inhibitor therapy in patients with wild type EGFR (which is an EGFR gene without any mutations).

In one example, there is disclosed the external application of isoform D. In another example, such an external application can be in form of, but is not limited to, a co-drug, a co-therapy and/or as an additional therapeutic agent for epidermal growth factor receptor-tyrosine kinase inhibitor therapy.

In one example, EGFR isoform D is secreted in exosomes. In another example, these EGFR isoform D-containing exosomes are administered to a person in need thereof. In yet another example, EGFR isoform D-containing exosomes are to be administered to a person in need thereof.

Exosomal EGFR isoform D can also be applied to patient-derived cells in culture, whereby such external application of EGFR isoform D has been shown to increase the cells' sensitivity to tyrosine kinase inhibitor therapy or tyrosine kinase inhibitors.

This external or extrinsic application of EGFR isoform D uses the endocytic pathway to promote tyrosine kinase inhibitors sensitivity in wild type EGFR.

Figure 9:
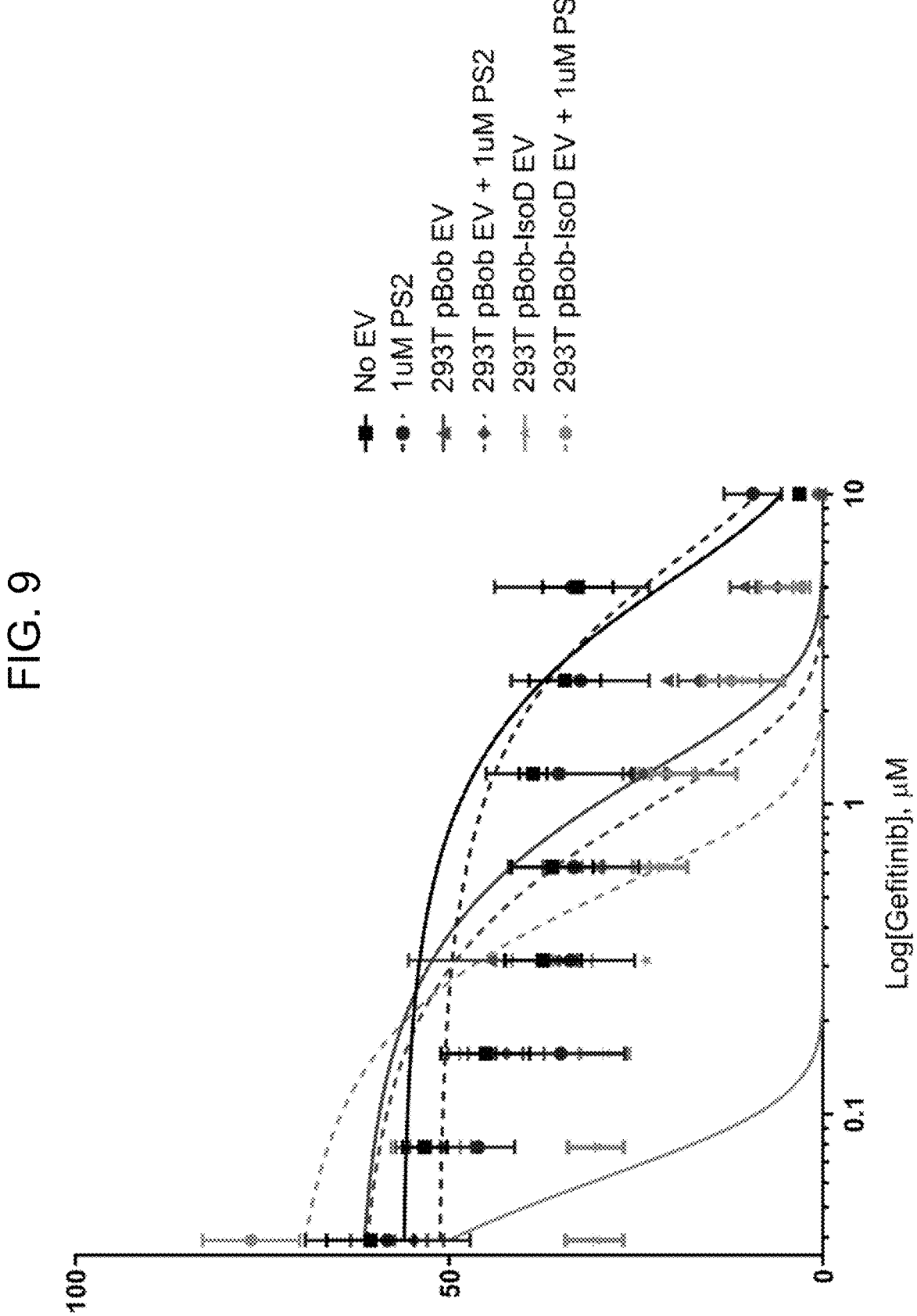
FIG. 9 shows the results of NCC-HN1 cells treated with no exosome (No EV), PitStop2 alone (1 µM PS2), exosome with vector expression (293T pBob EV), exosome with EGFR isoform D expression (293T pBob-IsoD EV), exosome with vector expression and PitStop2 (293T pBob EV+1 µM PS2), exosome with isoform D expression and PitStop2 (293T pBob-IsoD EV+1 µM PS2). This data shows the inhibition of clathrin-mediated endocytosis by PitStop2 reduces the sensitising effect of isoform D containing EVs.

During EGFR signalling, receptor homeostasis and down-regulation are governed through endocytic processes. Furthermore, there are reports suggesting that endocytic processes may be essential to EGFR-signalling, especially in the context of EGFR specific mutations. It was therefore sought to test if exosomal EGFR isoform D exerted its phenotype through these endocytic processes to confer its sensitizing effect. To this end, an inhibitor of clathrin-mediated endocytosis, PitStop2, was used. PitStop2 is known to inhibit the majority of EGFR-dependent endocytosis. Results showed that co-treatment of PitStop2 with exosome containing EGFR isoform D reversed the sensitizing effect gained when treating cells with EGFR isoform D alone (FIG. 9). This result illustrates that EGFR isoform D-mediated sensitivity requires EGFR signalling through endocytic processes.

For the majority of patients (>80-90%) who have squamous cell cancers (for example, but not limited to, head and neck, lung, oesophagus, bladder, and cervix), these cancers are dependent on the epidermal growth factor receptor (EGFR) pathway. However, as EGFR is commonly not mutated, epidermal growth factor receptor tyrosine kinase inhibitors (EGFR TKIs) have little to no effect. In such cases where EGFR is present in its wild-type form, exosomal EGFR isoform D can be used or administered as a co-drug to these patients, thereby augmenting the effect of EGFR TKI on these otherwise unresponsive cancers and increasing tumour sensitivity and/or vulnerability to the tyrosine kinase inhibitor class of drugs.

Examples of EGFR-dependent cancers are, but are not limited to, head and neck cancer, squamous cell carcinomas, head and neck squamous cell carcinomas (HNSCC), oral squamous cell carcinoma (OSCC), oesophageal, bladder, cervix, lung, squamous-cell skin cancer (also known as cutaneous squamous-cell carcinoma; cSCC) and non-small cell lung cancer (NSCLC). In one example, the EGFR-related cancer is, but is not limited to, head and neck cancer, oesophagus, bladder, cervix, skin, and lung cancer. In another example, the head and neck cancer is head and neck squamous cell carcinoma (HNSCC) or oral squamous cell carcinoma (OSCC). In yet another example, the lung cancer is non-small cell lung cancer (NSCLC). In a further example, the cancer is skin cancer. In another example, the skin cancer is squamous-cell skin cancer.

It was found that cell lines with an EGFR single nucleotide polymorphism (SNP), specifically Q787Q A/A, are sensitive to epidermal growth factor receptor tyrosine kinase inhibitors (EGFR TKIs). Such cells with mutated EGFR have also been shown to have increased mRNA expression of EGFR isoform D (see FIG. 1).

Figure 2:
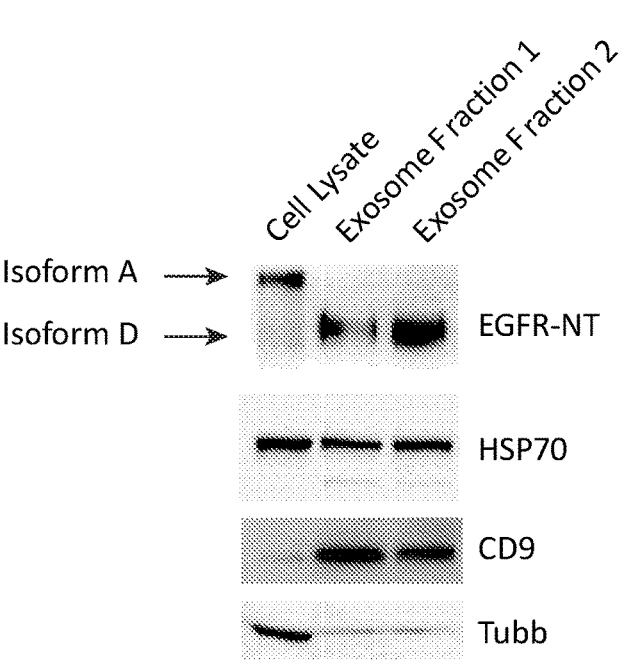
FIG. 2 shows the results of a Western blot analysis of total cell lysate and exosome fractions from NCC-HN19 cells collected at different time points. Tubb is use as a cytosolic marker and CD9 as an exosome marker. This data indicates EGFR isoform D is present in the exosomes/extracellular vesicles (EV).
Figure 3:
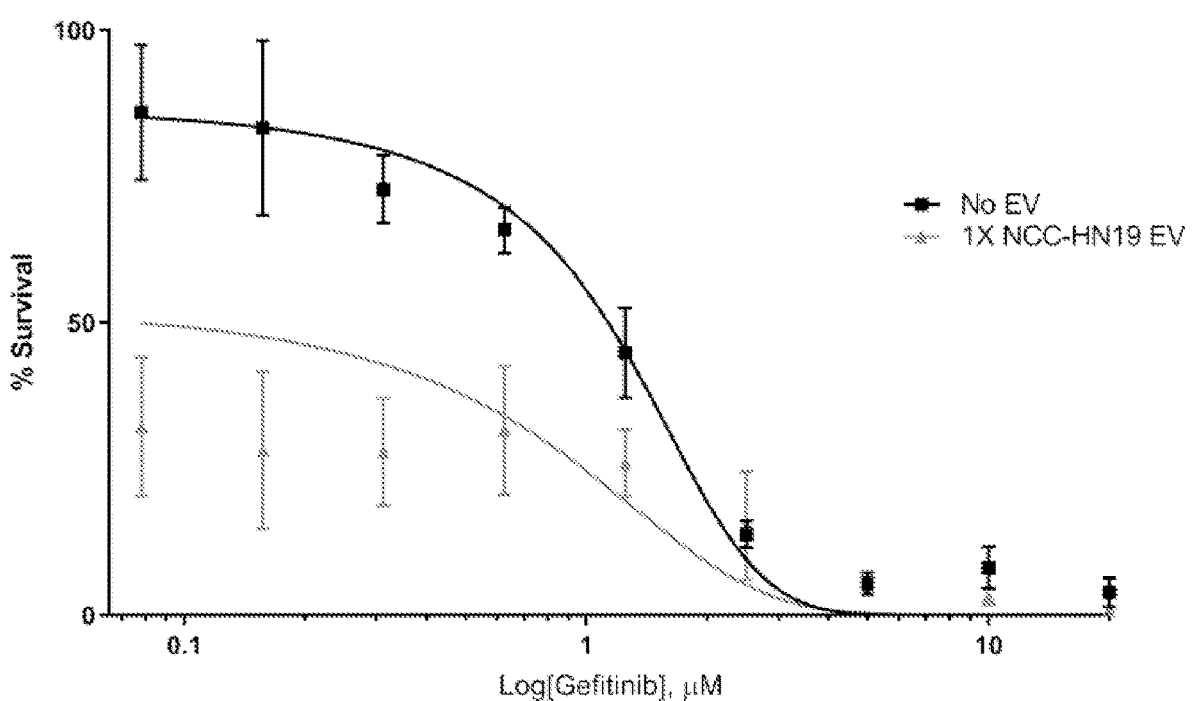
FIG. 3 shows the results of NCC-HN1 cell treated with no exosome/extracellular vesicle (No EV) or with exosome purified from NCC-HN19 cells (10% NCC-HN19 EV). This data shows exosome/extracellular vesicle containing EGFR isoform D can sensitise cancer cells to tyrosine kinase inhibitors (TKIs).
Figure 4:
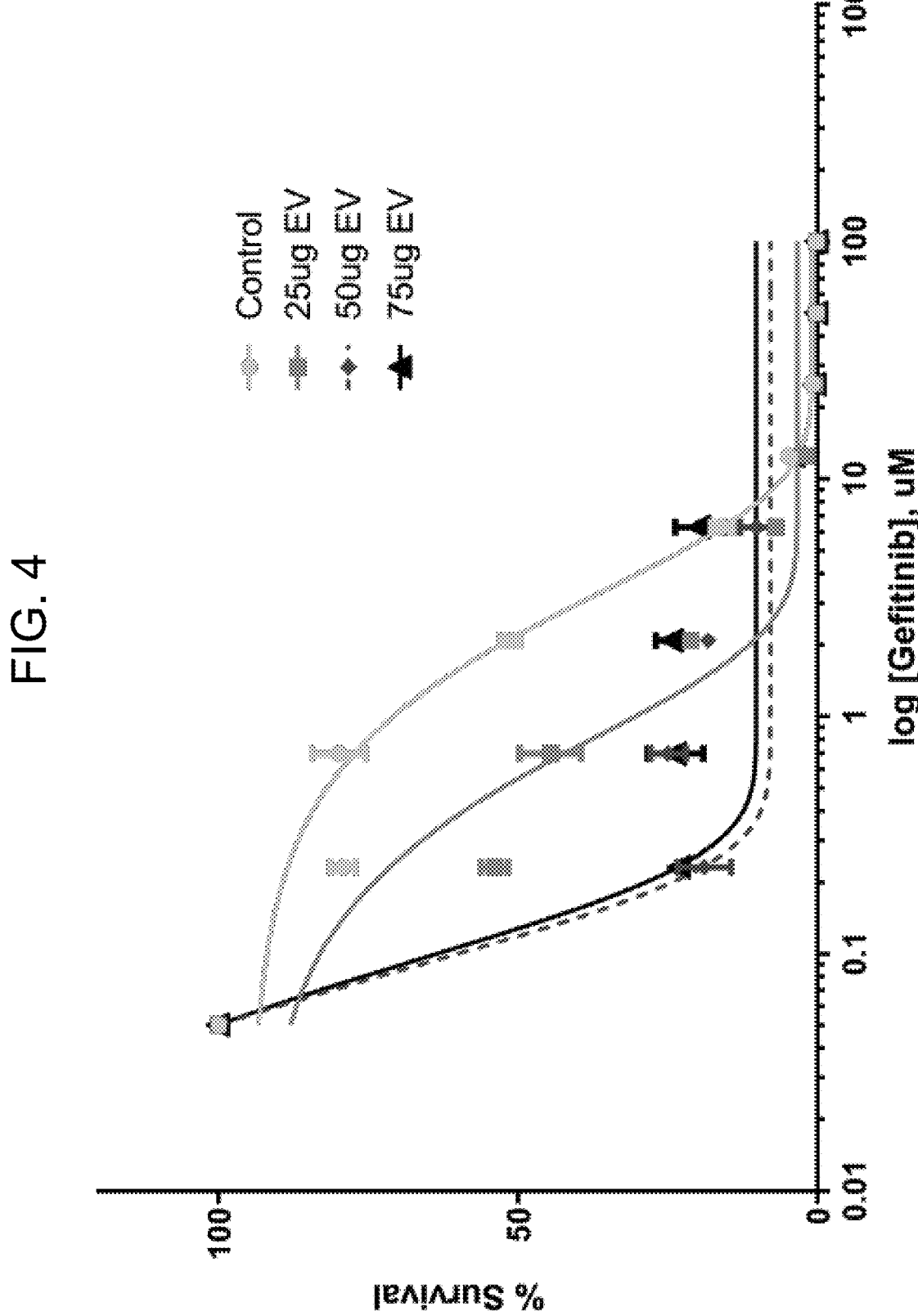
FIG. 4 shows dose dependent sensitisation of NCC-HN1 cells with increasing amount of exosome (EV) containing EGFR isoform D from NCC-HN19 cells. This data demonstrates that the exosomal isoform D-dependent sensitisation is dose-dependent.

In order to investigate the localization of EGFR isoform D, secreted fractions from one of these cell lines, NCC-HN19, were tested. It was found that EGFR isoform D is present in culture supernatant, and, specifically, in the exosome component of the cell (FIG. 2). Previous studies had shown that a ratio of high EGFR isoform D to isoform A expression in the cells resulted in epidermal growth factor receptor tyrosine kinase inhibitor (EGFR TKI) sensitivity, and that EGFR isoform D is secreted into the extracellular compartment. Without being bound by theory, it was thought that this sensitizing effect could be transferred. To this end, exosomes from the culture supernatant of cells (NCC-HN19) containing high levels of EGFR isoform D were isolated using a molecular weight cut-off filter, and subsequently applied to cells (NCC-HN1) that are normally resistant to the epidermal growth factor receptor tyrosine kinase inhibitor gefitinib. These cells were then treated with gefitinib to determine the $IC_{50}$ values, with or without exosome treatment. The results show that cells treated with EGFR isoform D-containing exosomes were more sensitive to gefitinib treatment (FIG. 3). Importantly, there is a dose-dependent effect to this tyrosine kinase inhibitor sensitivity, which increases proportionally with the amount of exosomes applied (FIG. 4).

Figure 5:
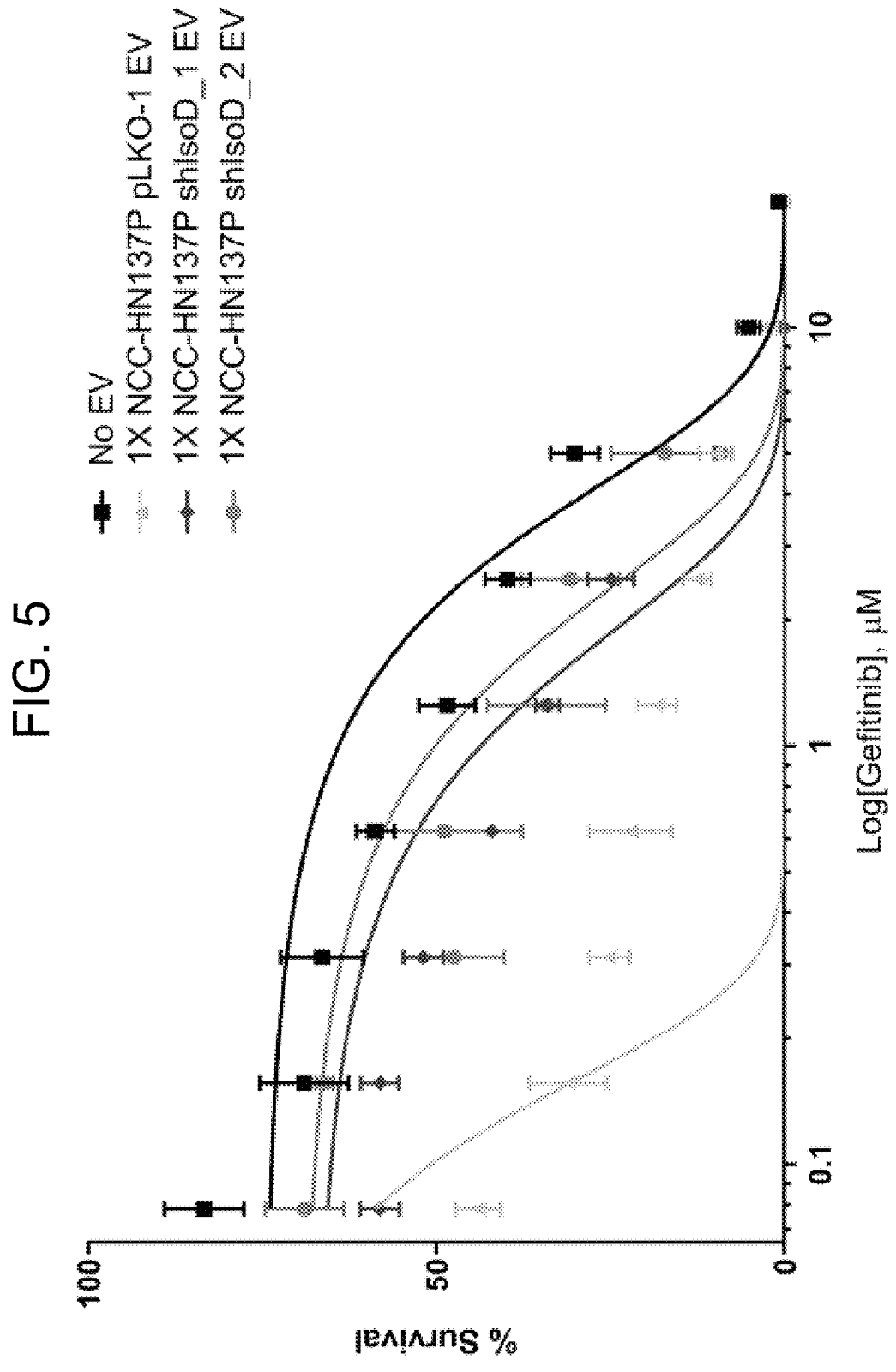
FIG. 5 shows the results of NCC-HN1 cells treated with no exosome (No EV), EGFR isoform D containing exosome (vector control, 10% HN137P pLKO-1 EV) or exosome knockdown with shRNA #1 (10% HN137P shIsoD_1 EV) or shRNA #2 (10% HN137P shIsoD_2 EV) against EGFR isoform D. This data indicates the necessity of EGFR Isoform D in the EV to sensitise cancer cells, as specific depletion of EGFR Isoform D alone reduces the tyrosine kinase inhibitor (TKI) sensitising effect.

Next, it was sought to determine whether exosomal EGFR isoform D on its own is necessary to confer epidermal growth factor receptor tyrosine kinase inhibitor (EGFR TKI) sensitivity. To establish that EGFR isoform D is the essential protein to modulate this sensitivity to gefitinib treatment in target cells, EGFR isoform D expression was knocked down using two different shRNAs (FIG. 5). The data shows that the treatment of target cells using exosomes with a reduction (knock-down) of EGFR isoform D expression, resulted in reduced sensitivity to gefitinib compared to controls (exosomes containing normal levels of EGFR isoform D expression). This indicates that EGFR isoform D is necessary to confer a sensitizing effect to cells which are otherwise not sensitive to tyrosine kinase inhibitor (TKI) treatment.

To determine if EGFR isoform D on its own was sufficient to sensitise cells to tyrosine kinase inhibitor (TKI) treatment, the EGFR isoform D protein was overexpressed in an

Figure 6:
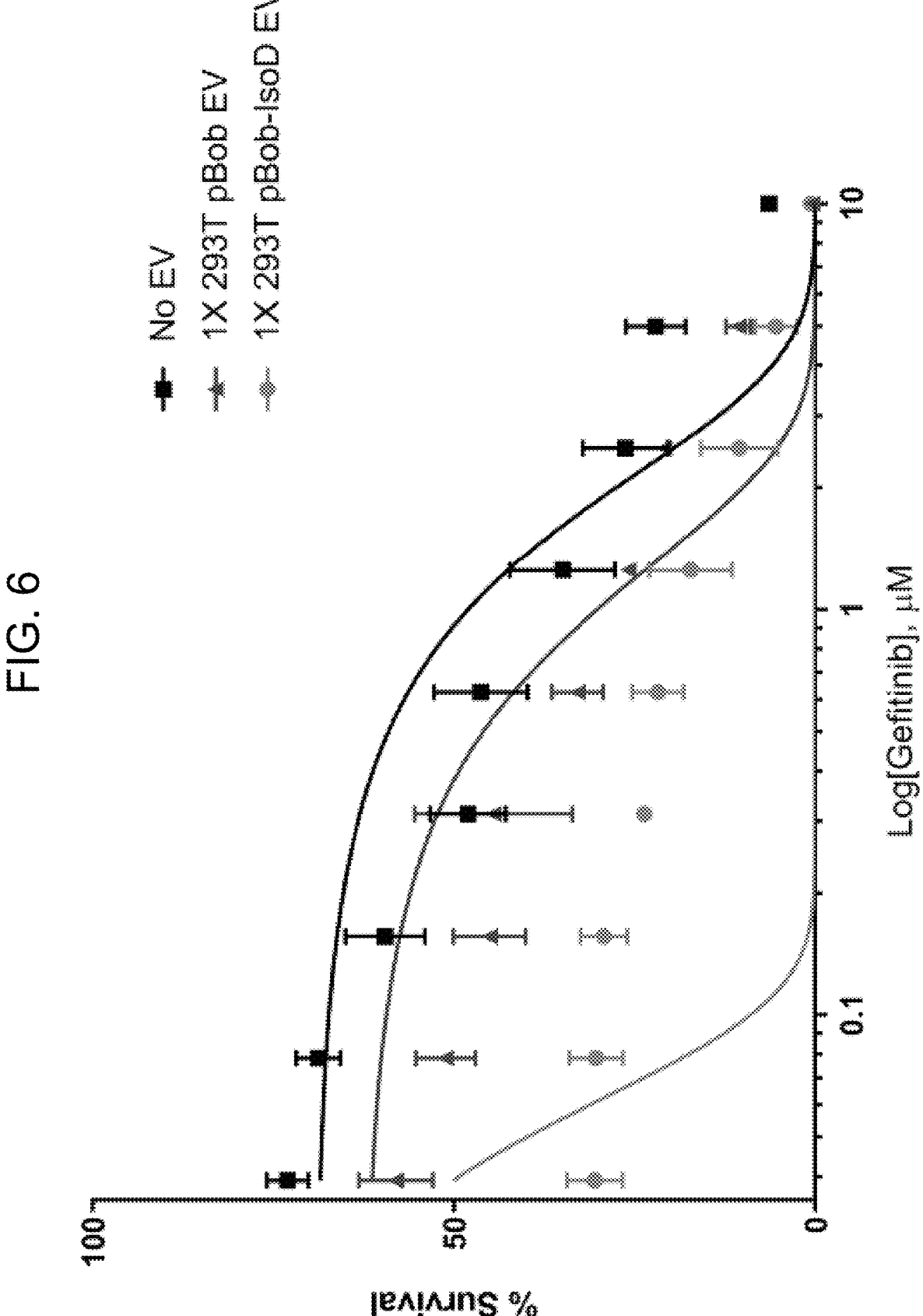
FIG. 6 shows the results of NCC-HN1 cells treated with no exosome (No EV), vector only exosome (10% 293T pBob EV), or exosome over-expressing EGFR isoform D (10% 293T pBob-IsoD EV). This data shows that the ectopic expression of EGFR isoform D alone in the EV is sufficient to sensitise cells to EGFR tyrosine kinase inhibitors (TKIs).

12 embryonic kidney cell line, HEK 293T, which do not contain EGFR isoform D, and is commonly used to derive therapeutic exosomes. The expressed protein/exosomes were then purified and applied to onto target cells (HCC-HN1 cells in this case). It was found that exosomes containing overexpressed EGFR isoform D enhanced sensitivity to subsequent gefitinib treatment (FIG. 6).

Figure 7:
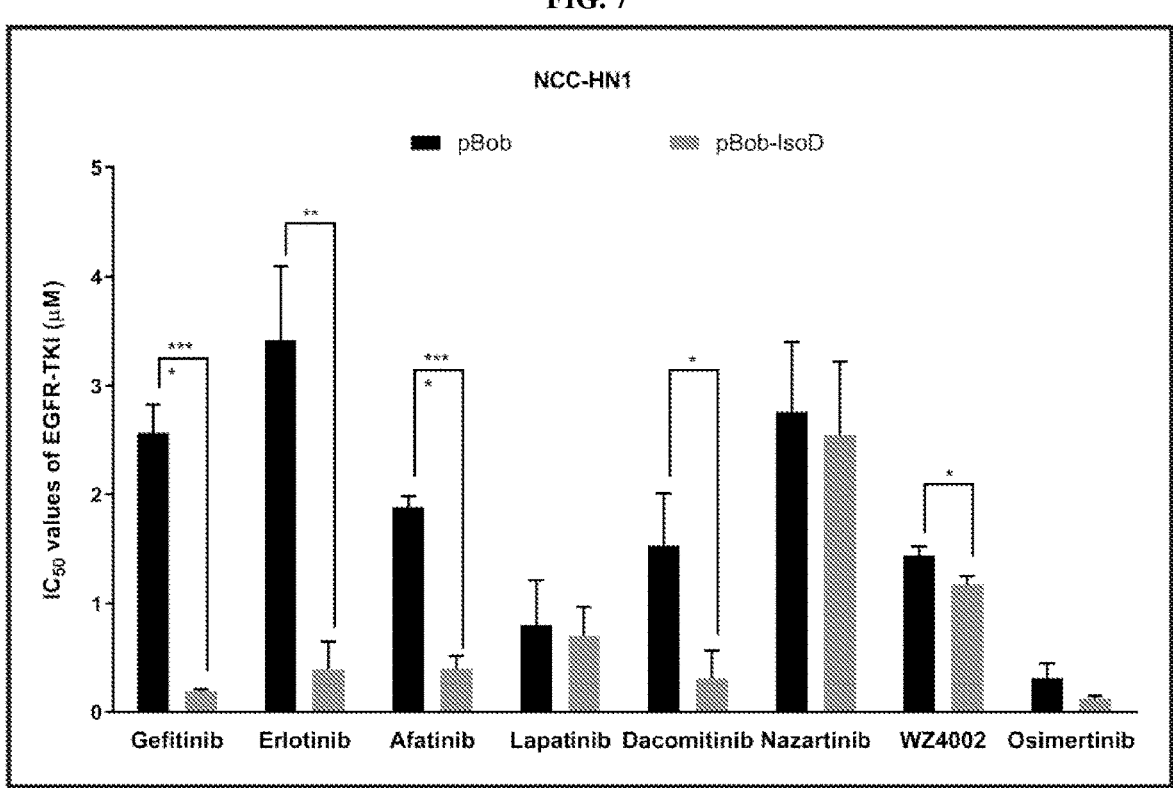
FIG. 7 shows the $IC_{50}$ values obtained for three primary HNSCC cell lines (NCC-HN1, NCC-HN120M and NCC-HN182M) which had been treated with exosome from cells expressing vector control (pBob) or EGFR isoform D (pBob-IsoD) in combination with first generation tyrosine kinase inhibitors (gefitinib and erlotinib), second generation tyrosine kinase inhibitors (afatinib and dacomitinib) and third generation tyrosine kinase inhibitors (osimertinib, lapatinib, nazartinib and WZ4002). This data shows that EV with ectopically expressed EGFR isoform D can sensitise several HNSCC cell lines to both first, second and third generation tyrosine kinase inhibitors (TKIs).
Figure 7:
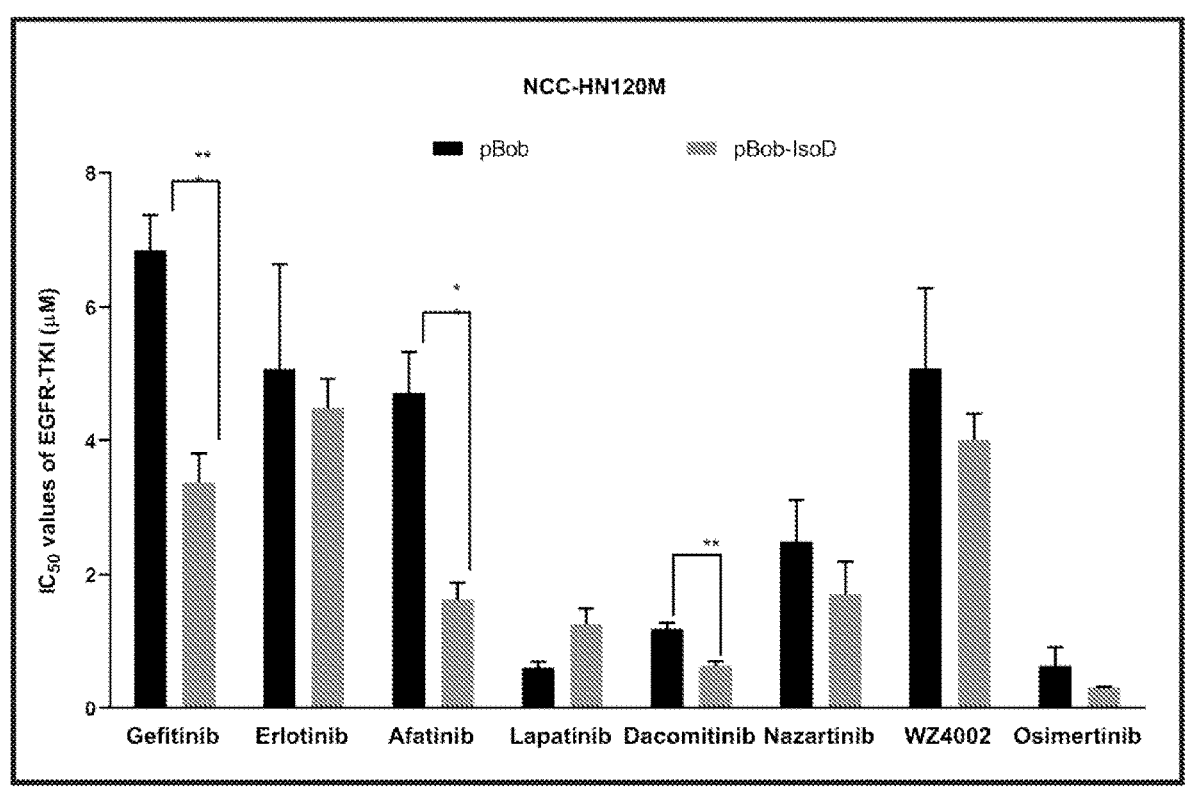
Figure 7:
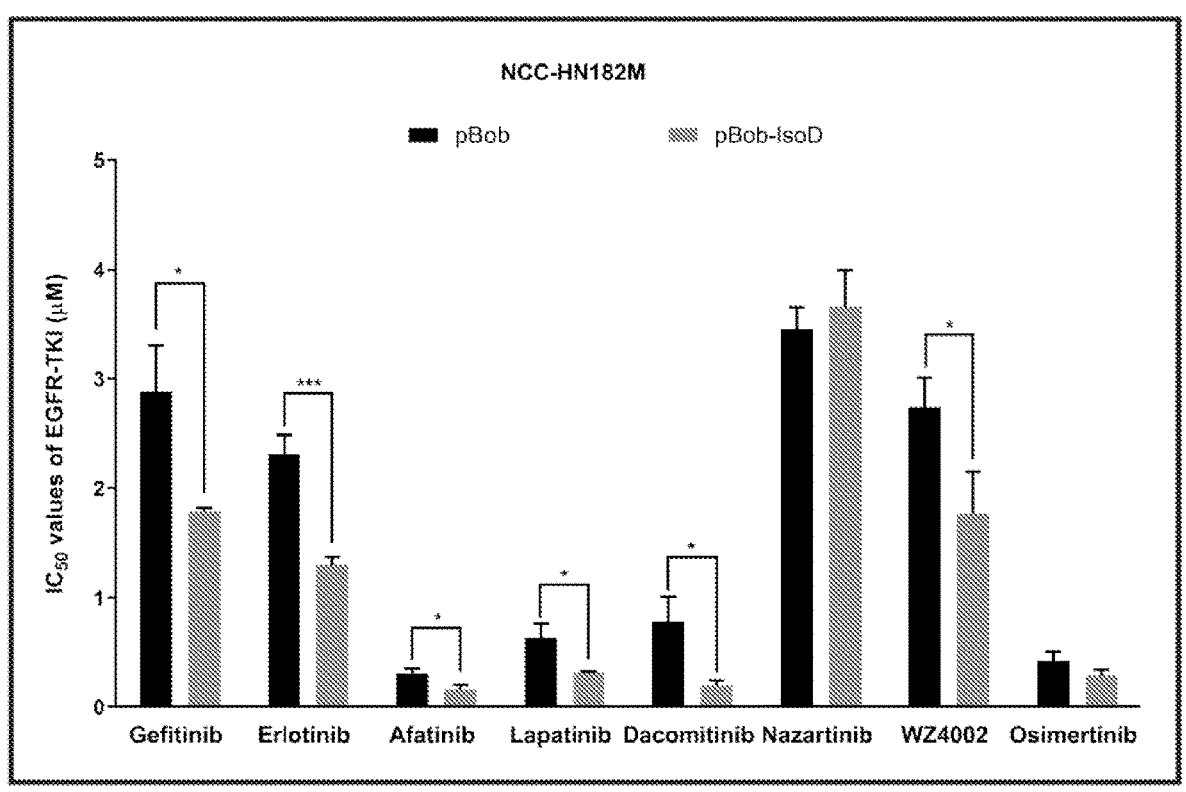

The latter experiment has been repeated by applying 293T-derived exosomal EGFR isoform D on to a number of different patient-derived cell lines and subsequent treatment with different EGFR tyrosine kinase inhibitors (TKIs). Results show that co-treatment of the tyrosine kinase inhibitors (TKIs) with EGFR isoform D-containing exosomes promotes sensitivity to EGFR TKIs (FIG. 7).

Figure 8:
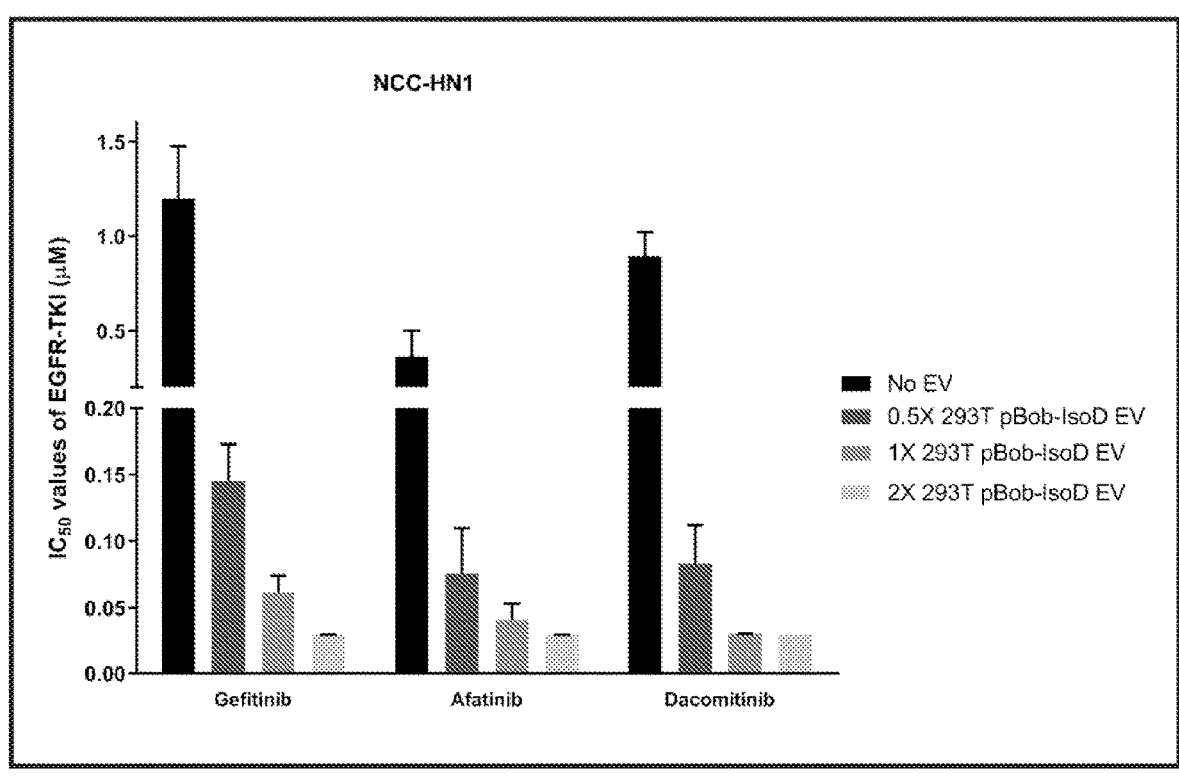
FIG. 8 shows the $IC_{50}$ values obtained for three primary HNSCC cell lines (NCC-HN1, NCC-HN120M and NCC-HN182M) which had been treated with no exosome (No EV) or exosome from cells (293T or NCC-HN1) over-expressing EGFR isoform D (pBob-IsoD) in increasing dosage (0.5×, 1× and 2×) and in combination with gefitinib, afatinib or dacomitinib. This data shows EVs with ectopically expressed EGFR isoform D increases sensitising effect to tyrosine kinase inhibitors (TKIs) in multiple HNSCC cell lines, and this sensitisation is dose-dependent.
Figure 8:
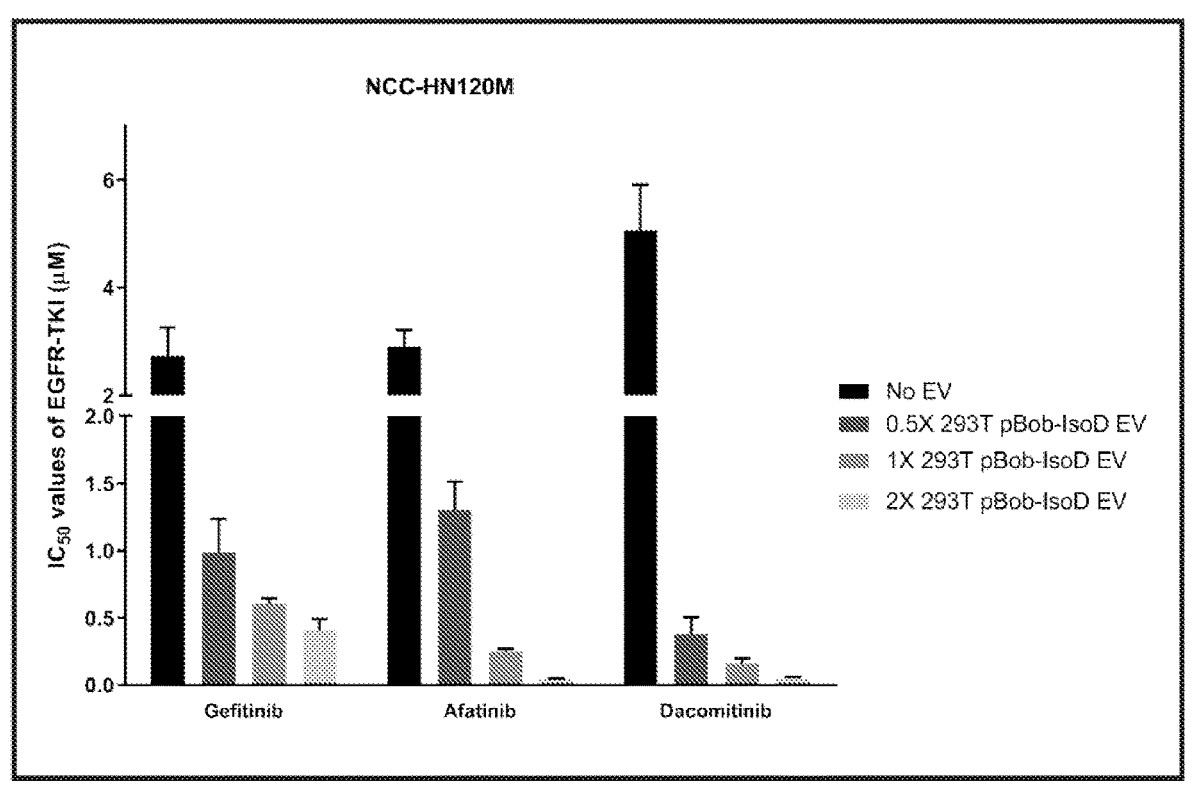
Figure 8:
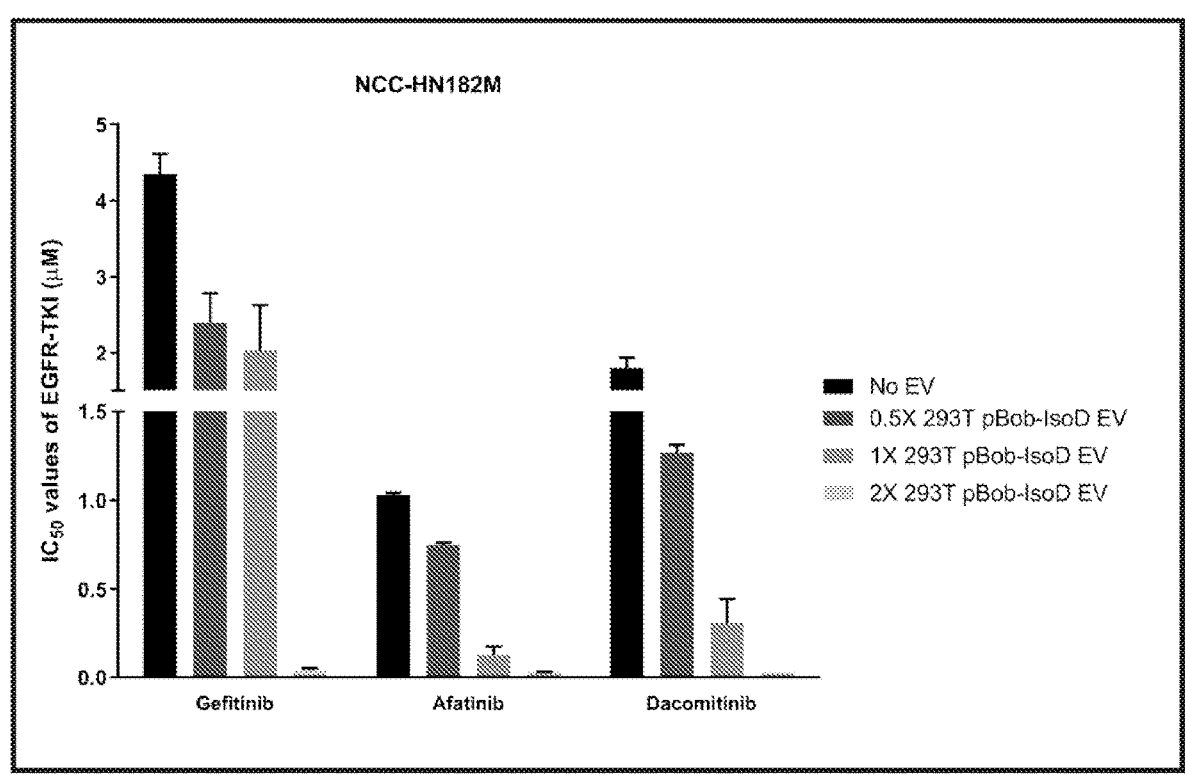
Figure 8:
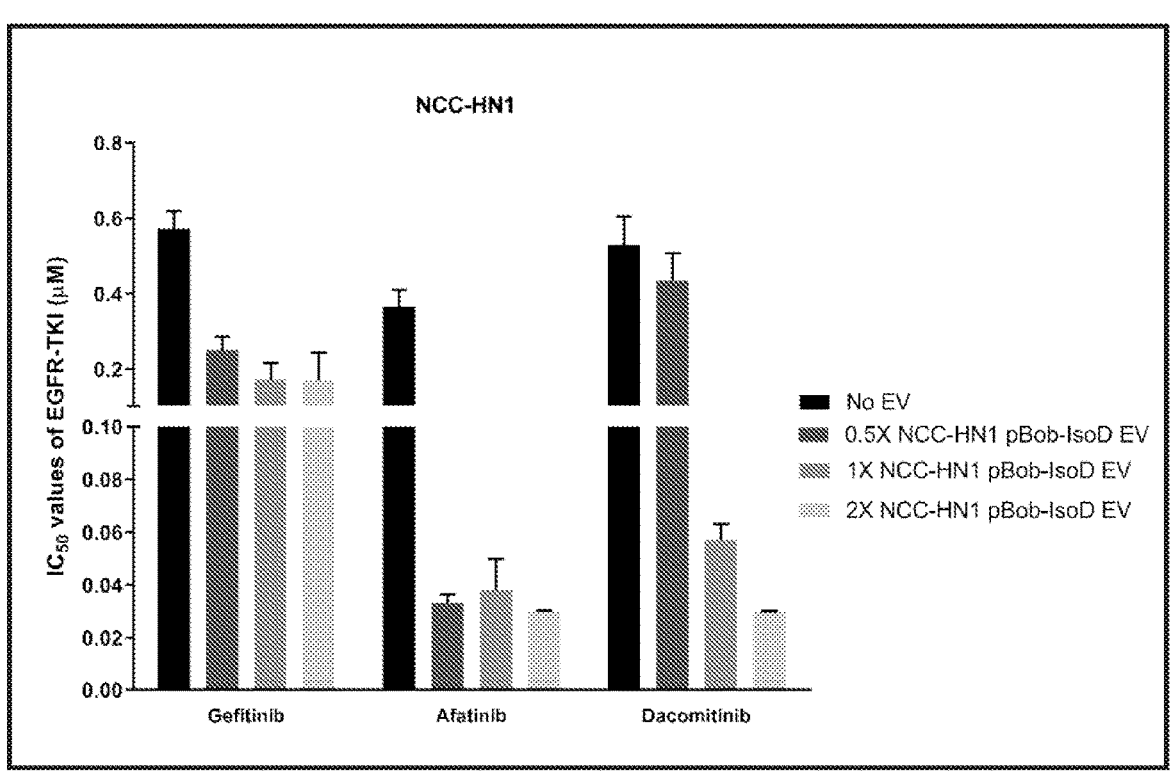
Figure 8:
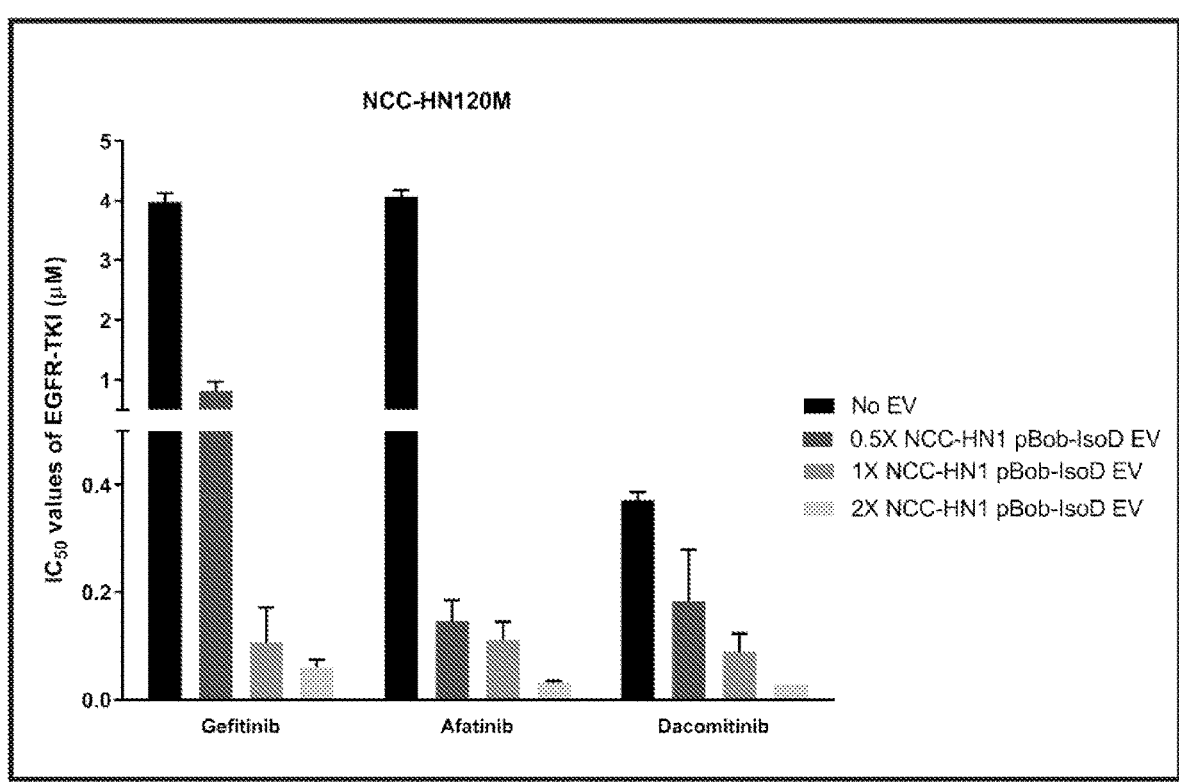
Figure 8:
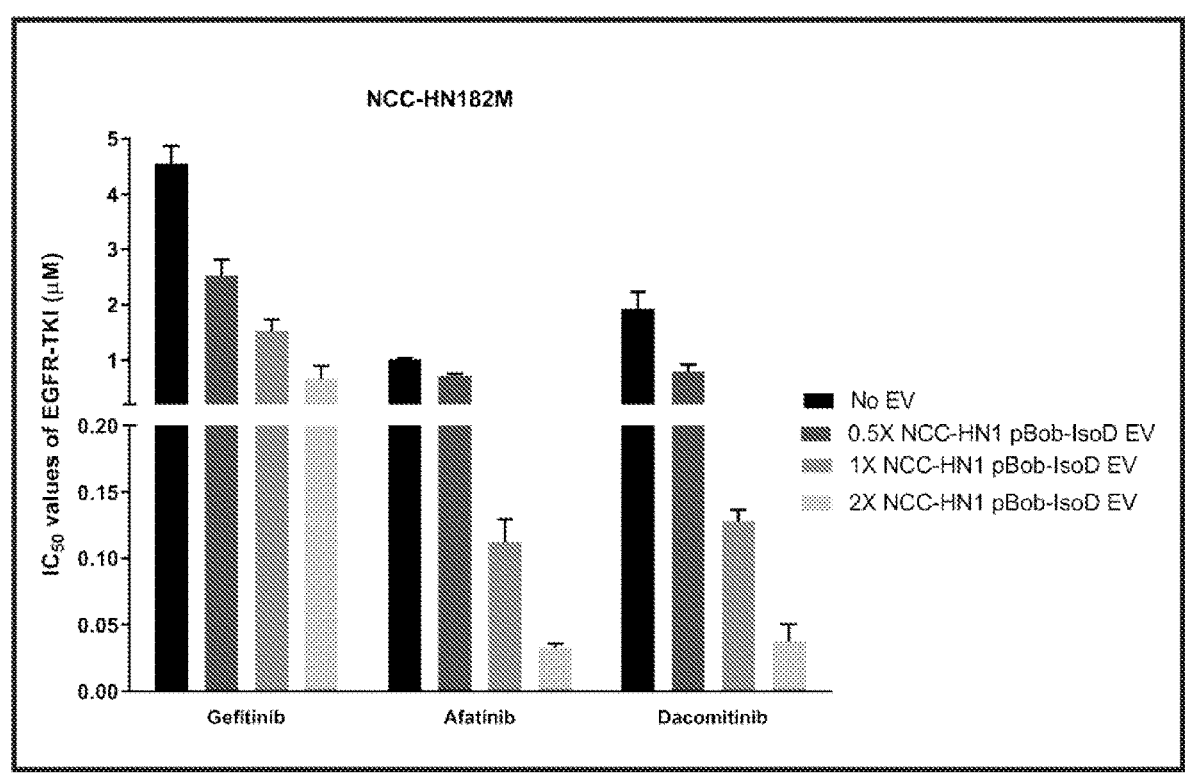
Figure 10:
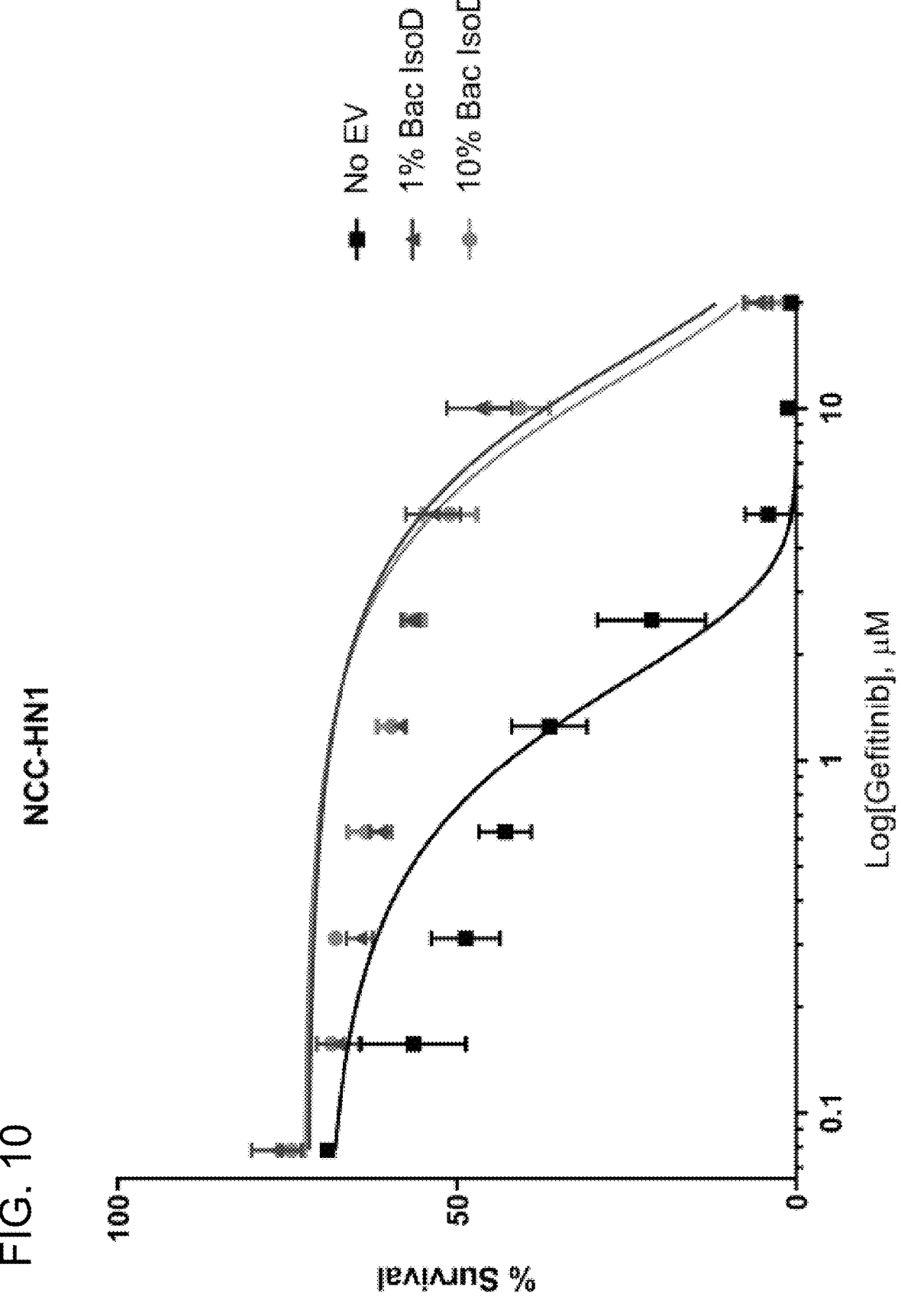
FIG. 10 shows the percentage survival of NCC-HN1 treated with gefitinib in the absence (No EV) or presence of 1% (1% v/v Bac IsoD) or 10% (10% v/v Bac IsoD) bacterially produced EGFR isoform D. This data shows that recombinant EGFR isoform D protein alone is unable to increase the sensitisation of cancer cells to TKI.

Using increasing quantities of the overexpressed EGFR isoform D-containing exosomes from 293T cells was shown to have a dose dependent effect on promoting sensitivity to EGFR TKIs (FIG. 8). It was further shown that the application of purified, non-exosomal EGFR isoform D had little to no effect on response to tyrosine kinase inhibitor in any of the systems mentioned above (FIG. 10). It is shown that a bacterial system expressed version of EGFR isoform D (which lacks exosomal packaging) did not have the same effect on the cells as administration of exosomal EGFR isoform D. To investigate the function of isolated EGFR isoform D protein, EGFR isoform D protein was overexpressed in a bacterial system and subsequently purified. NCC-HN1 cells were then co-treated with purified EGFR isoform D protein and gefitinib. Data shows that EGFR isoform D, when produced in bacteria and without packaging into exosome, failed to sensitise cells to gefitinib treatment. This data is shown in FIG. 10. Also, it was thought that the expressed EGFR isoform D protein is membrane bound, thus further underlining the need for the exosomal form of the protein.

Figure 13:
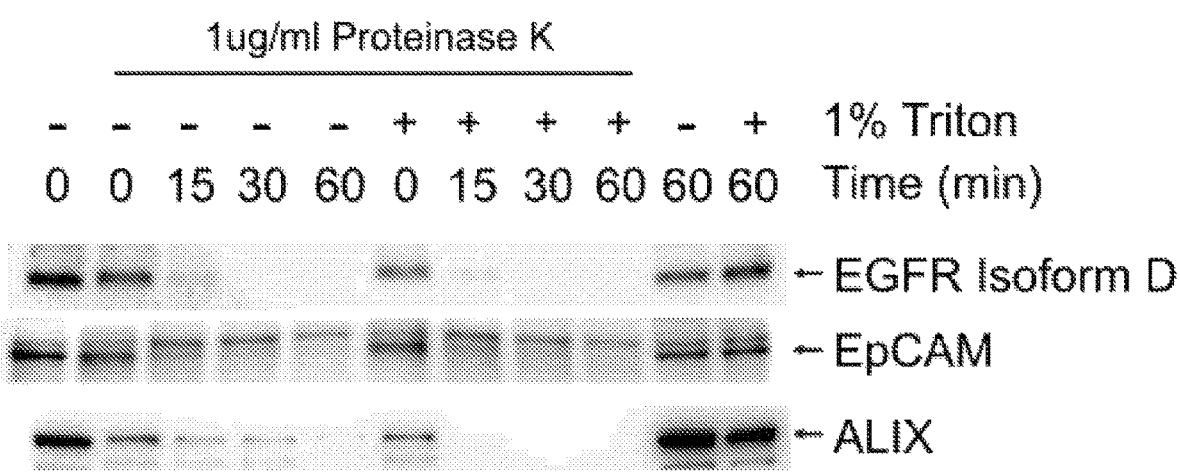
FIG. 13 shows results of a Western blot analysis of isolated exosomes upon proteinase K digestion. Isolated exosomes from NCC-HN19 were subjected to proteinase K digestion for 0, 15, 30, 60 minutes (min) in the absence (−) or presence (+) of 1% Triton-X 100. Samples were analysed for the presence of EGFR isoform D, EpCAM and ALIX. Equal amount of total protein was loaded into each lane. This data shows that EGFR isoform D is located on the surface of the EV particles in a similar manner to EpCAM.

To determine the localization of EGFR isoform D in the exosome, the biochemical property of the lipid membrane of the exosome in preventing macromolecules diffusion into the exosome lumen was utilised. Proteinase K was applied to purified exosomes for a limited duration (0 to 60 minutes), in the absence or presence of lipid disrupting detergent, 1% Triton-X 100. The resulting presence or absence of EGFR isoform D is correlated to exosomal surface bound protein, EpCAM, or exosomal luminal protein, ALIX. As can be seen from the western blot analysis (see FIG. 13), EGFR isoform D digestion profile correlates closely to EpCAM level, indicating that EGFR isoform D is located on the surface of the exosome.

Thus, in one example, the epidermal growth factor receptor isoform D is exosomal epidermal growth factor receptor isoform D, also referred to herein as "EGFR IsoD" or variations thereof. In yet another example, the epidermal growth factor receptor isoform D is provided as exosomal formulations (e.g., nanoparticles). In another example, the epidermal growth factor receptor isoform D is provided as one or more of the following: exosomal formulations, liposomal formulations, nanocarriers and nanoparticles.

The data shown herein indicates that exosomal EGFR isoform D can be provided as a co-treatment agent in gefitinib therapy for head and neck squamous cell carcinomas (HNSCC) to improve the efficiency of a gefitinib treatment regime.

Also disclosed herein is the use of epidermal growth factor receptor isoform D as disclosed herein in the manufacture of a medicament for use in combination therapy for treating an EGFR-related cancer, wherein said medicament is to be administered in combination with a tyrosine kinase inhibitor. In such examples, the tyrosine kinase inhibitor is to be, or is, administered separately, before, after, or in combination with, the epidermal growth factor receptor isoform D.

Figure 11A:
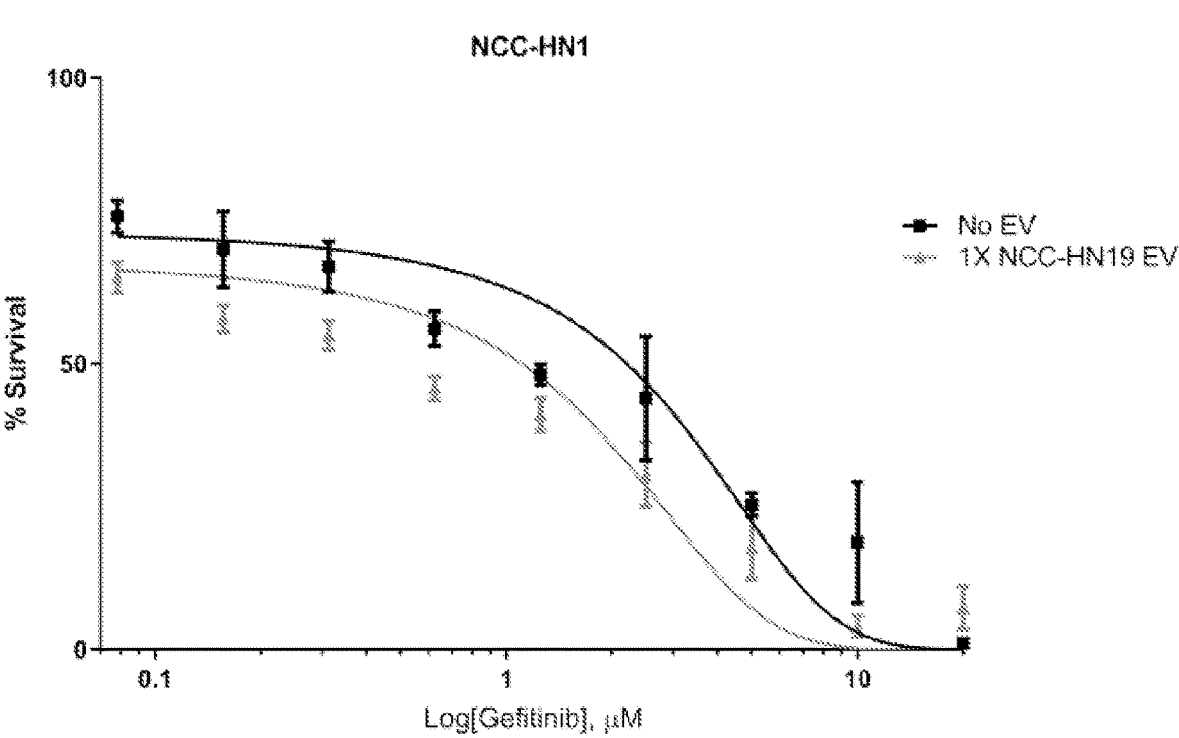
FIG. 11A shows the results of NCC-HN1 cells co-treated with NCC-HN19EV and eight tyrosine kinase inhibitors (TKIs). Graphs show the percentage of survival of NCC-HN1 cells treated without exosome (No EV) or with exosome from NCC-HN19 cells (1×NCC-HN19EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11A:
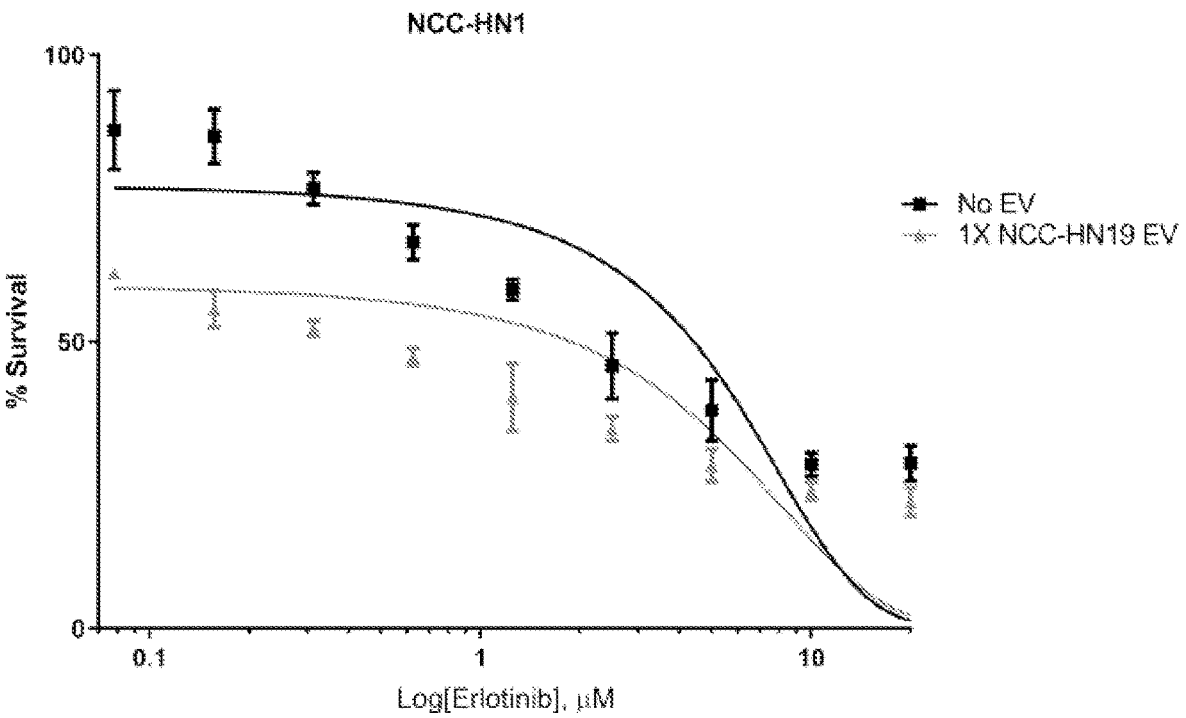
Figure 11A:
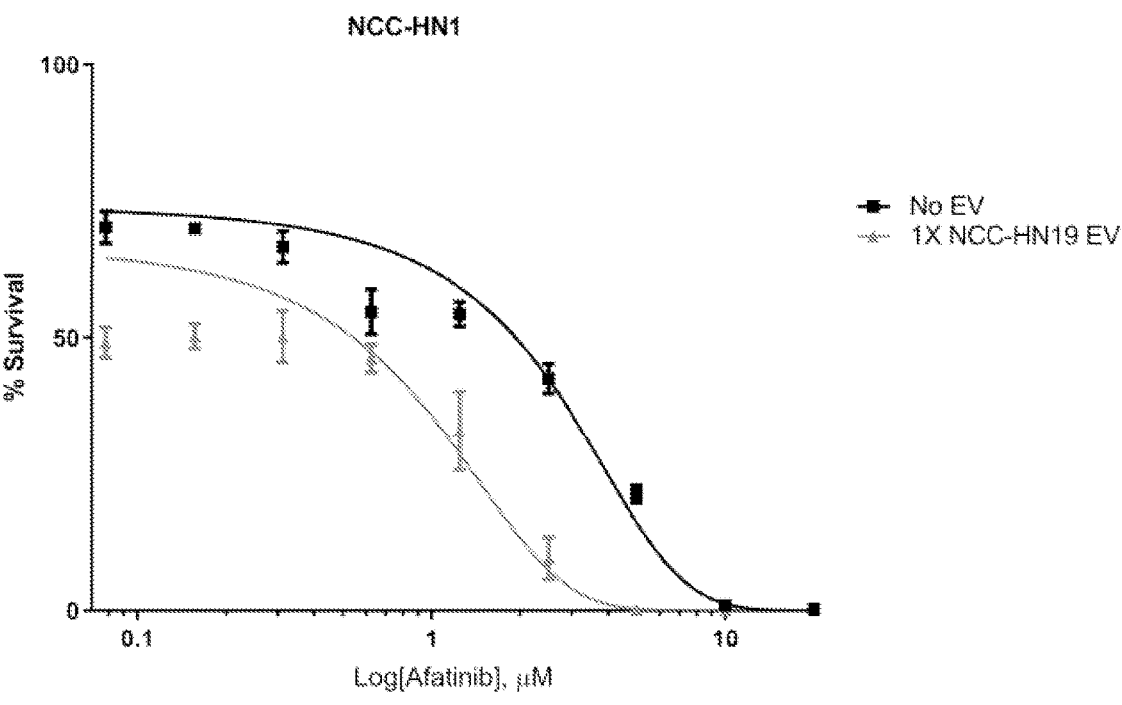
Figure 11A:
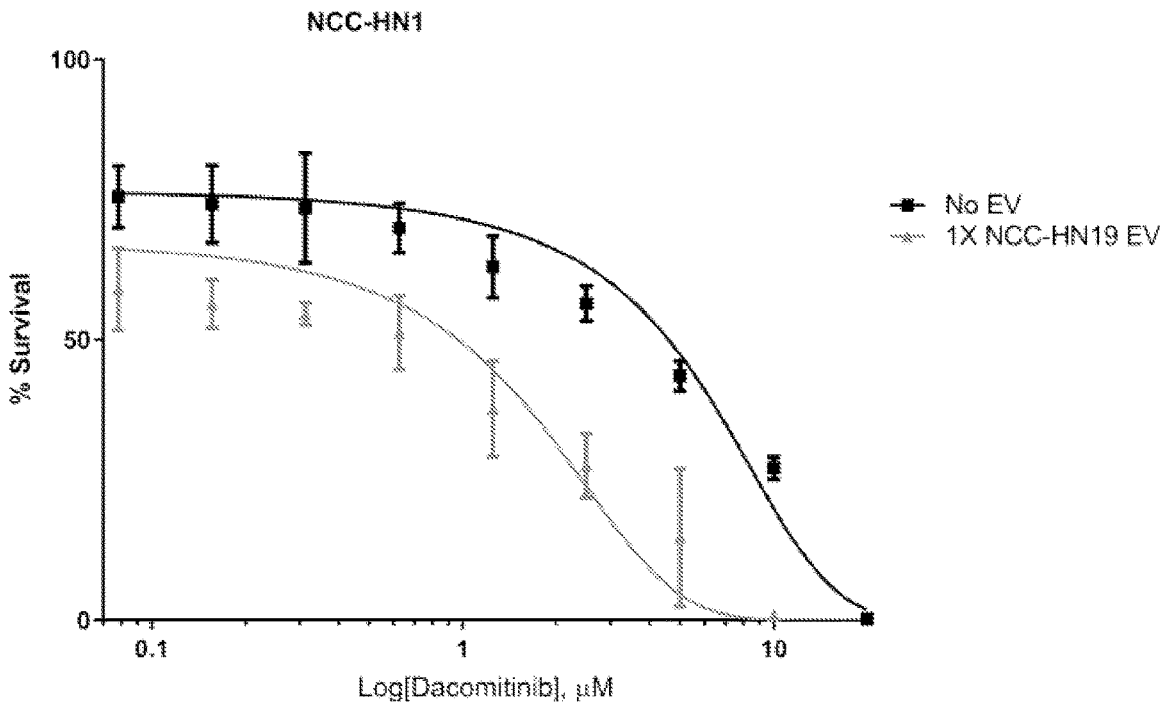
Figure 11A:
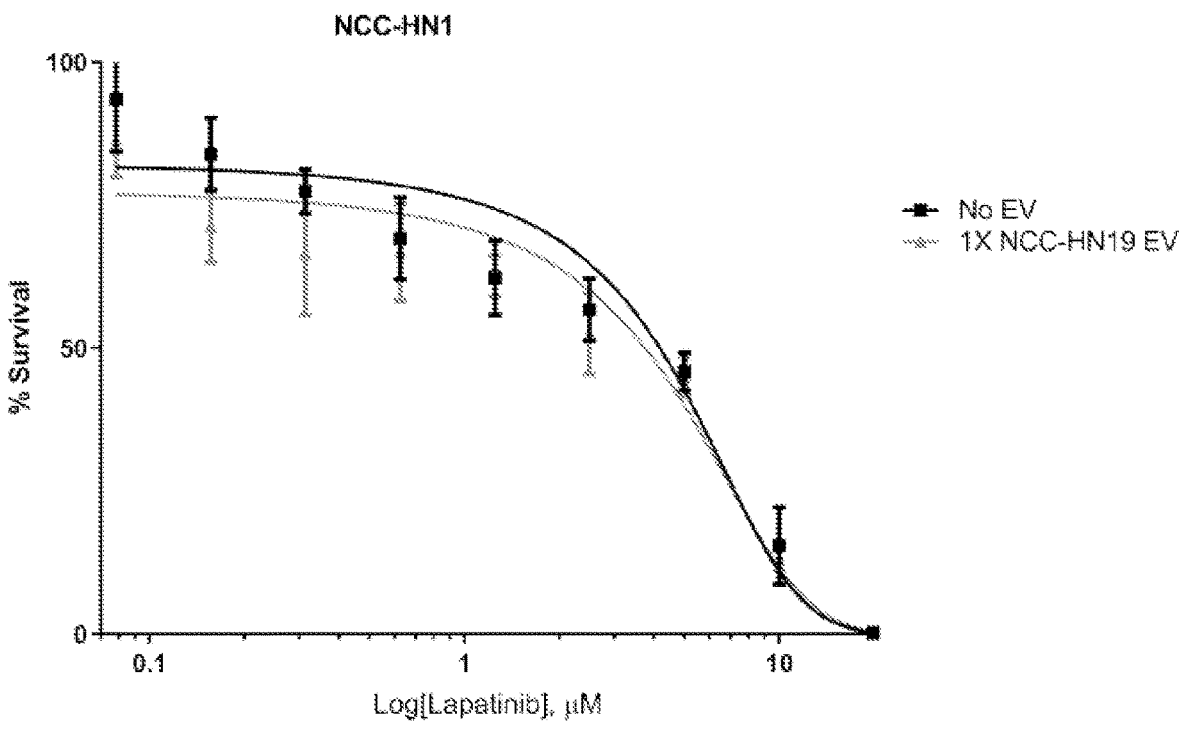
Figure 11A:
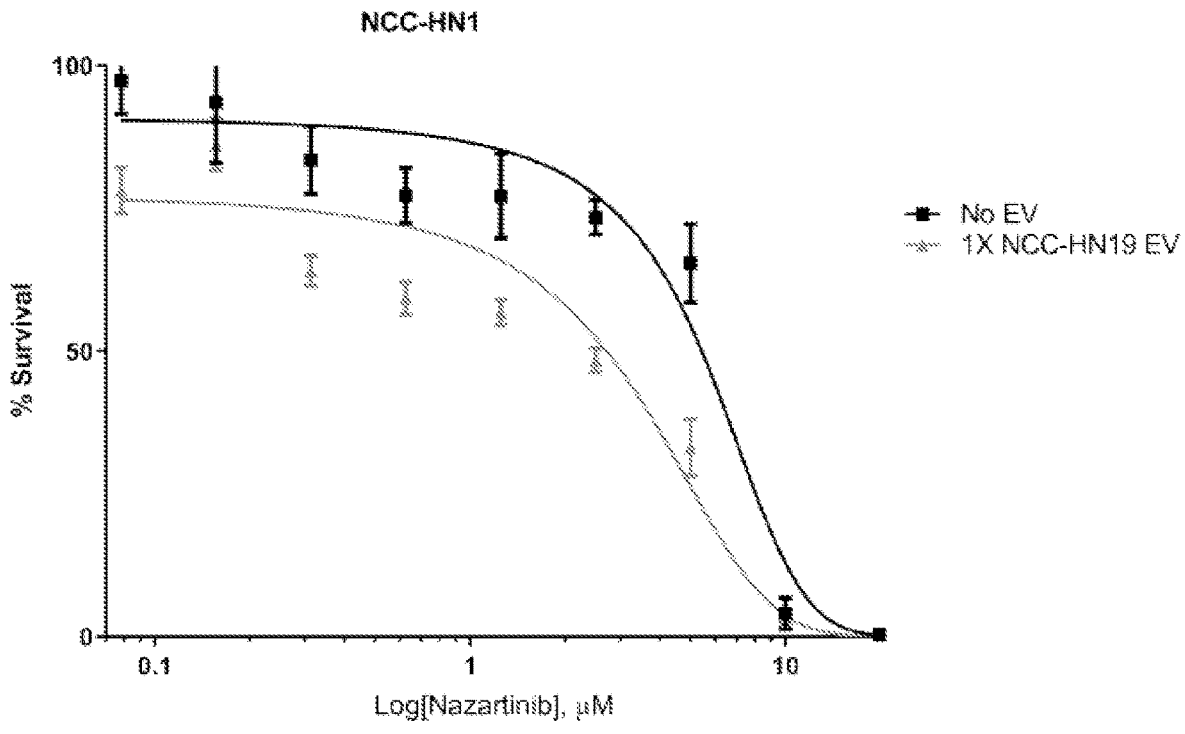
Figure 11A:
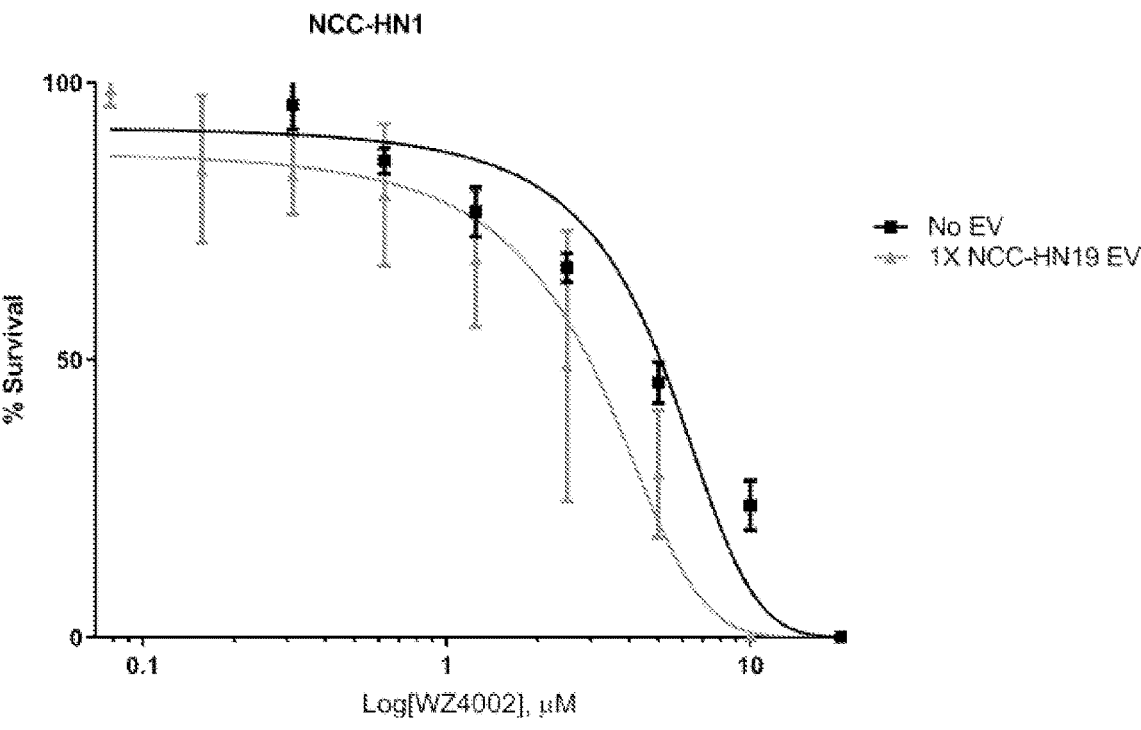
Figure 11A:
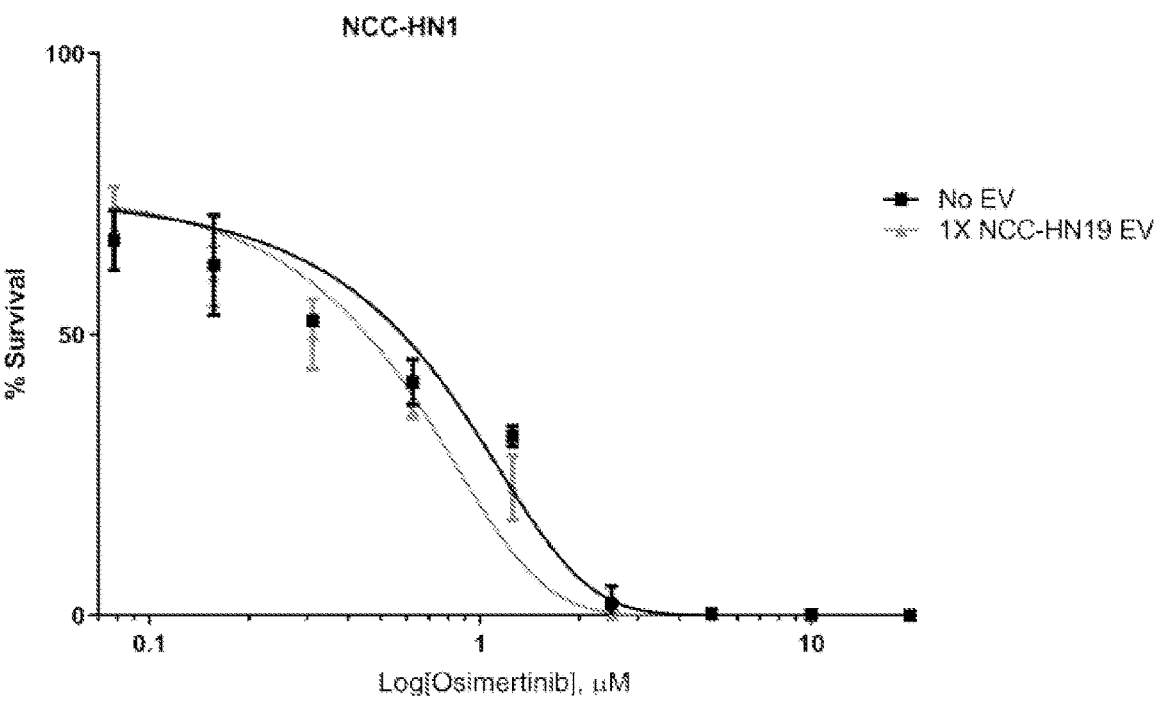
Figure 11B:
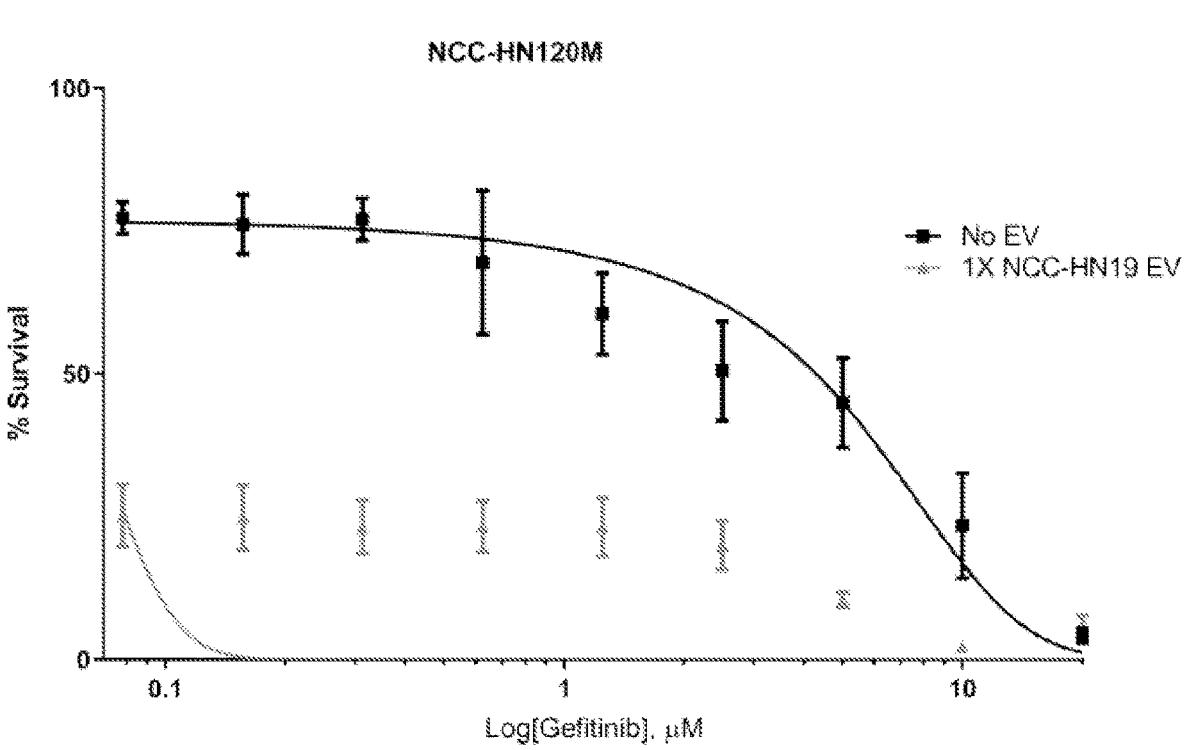
FIG. 11B shows the results of NCC-HN120M cells co-treated with NCC-HN19EV and eight tyrosine kinase inhibitors. Graphs show the percentage of survival of NCC-HN120M cells treated without exosome (No EV) or with exosome from NCC-HN19 cells (1×NCC-HN19EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11B:
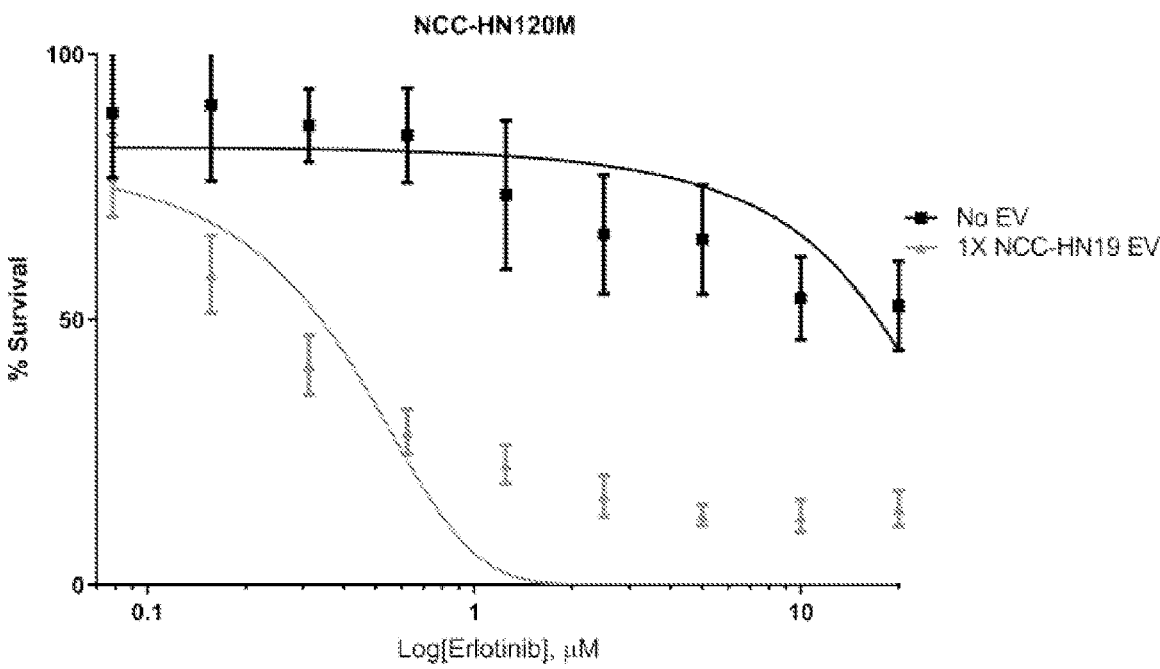
Figure 11B:
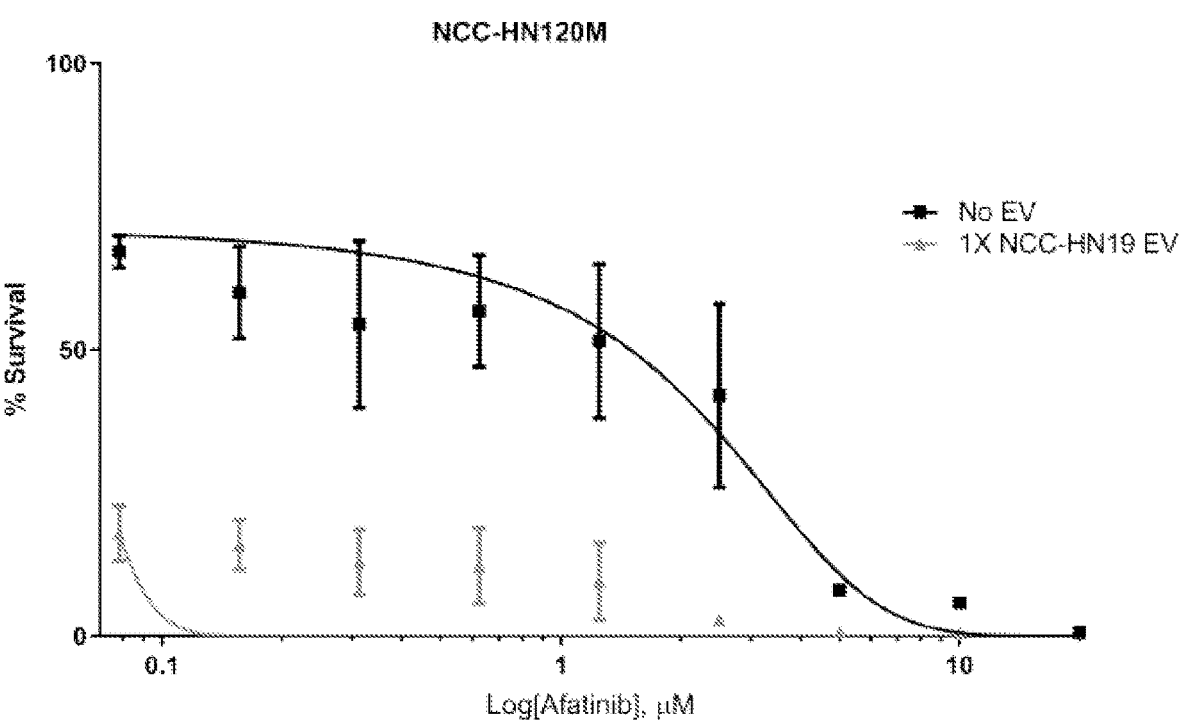
Figure 11B:
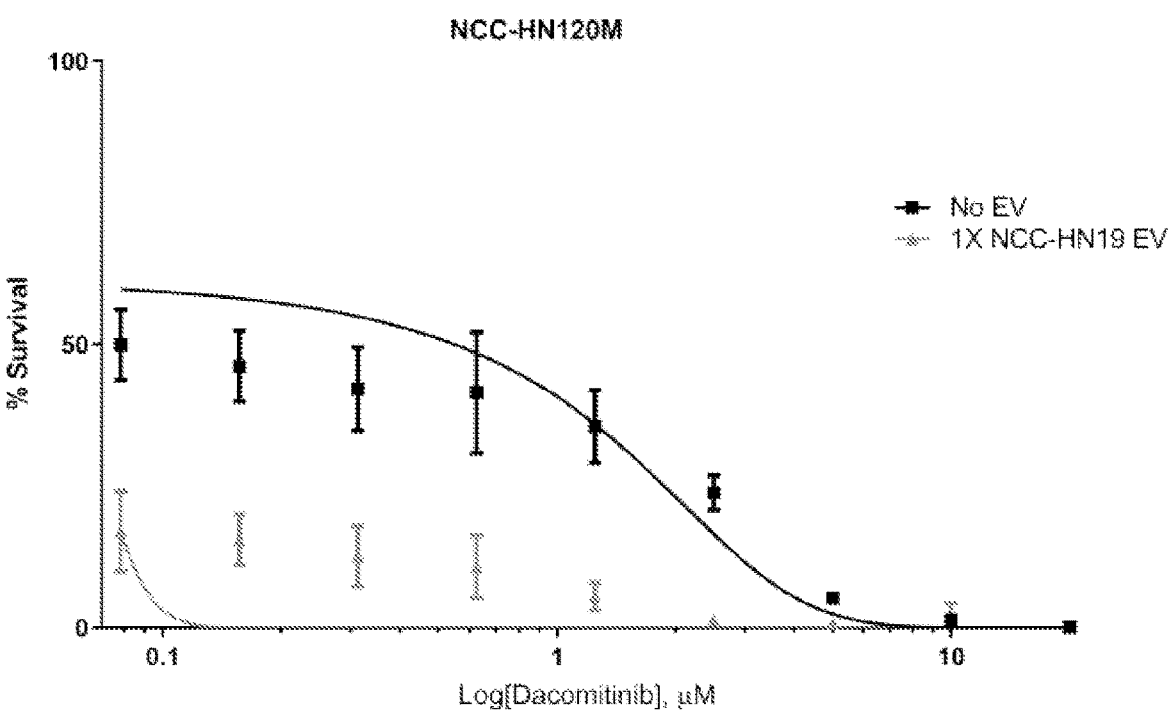
Figure 11B:
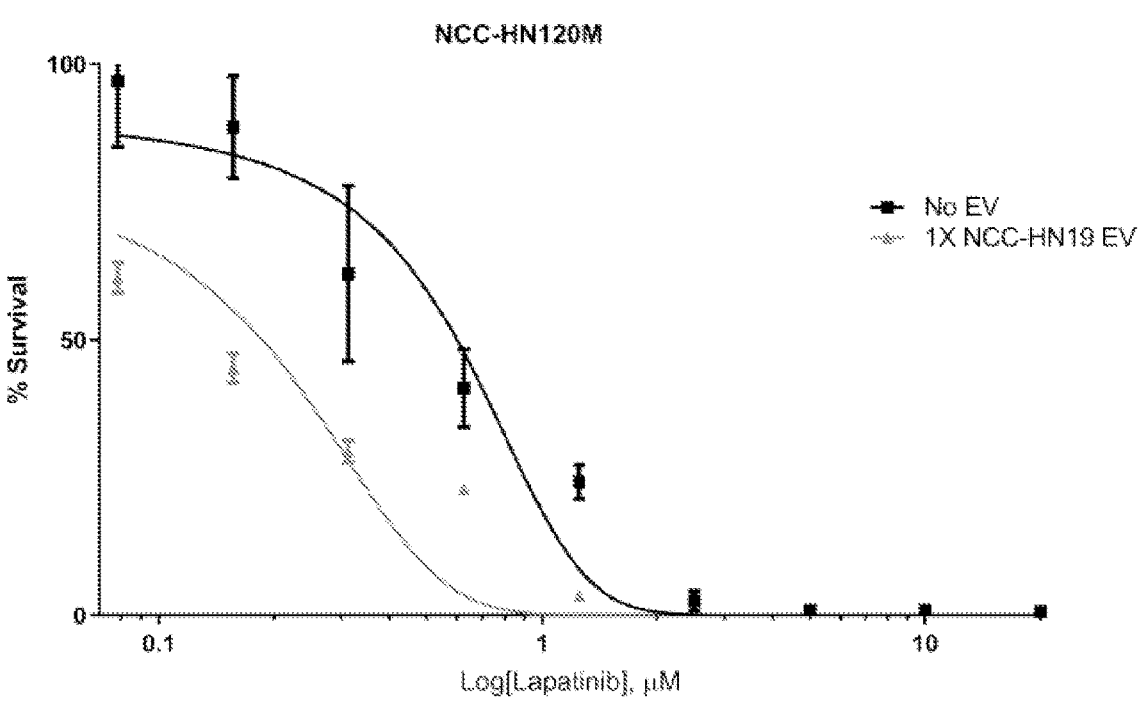
Figure 11B:
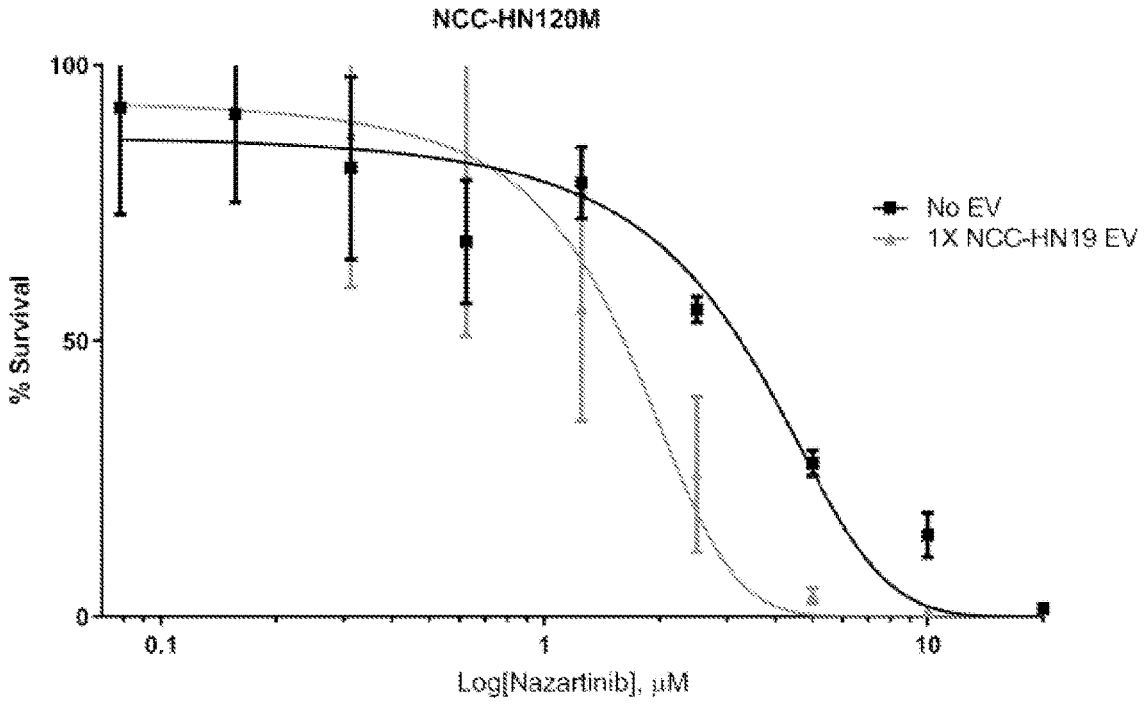
Figure 11B:
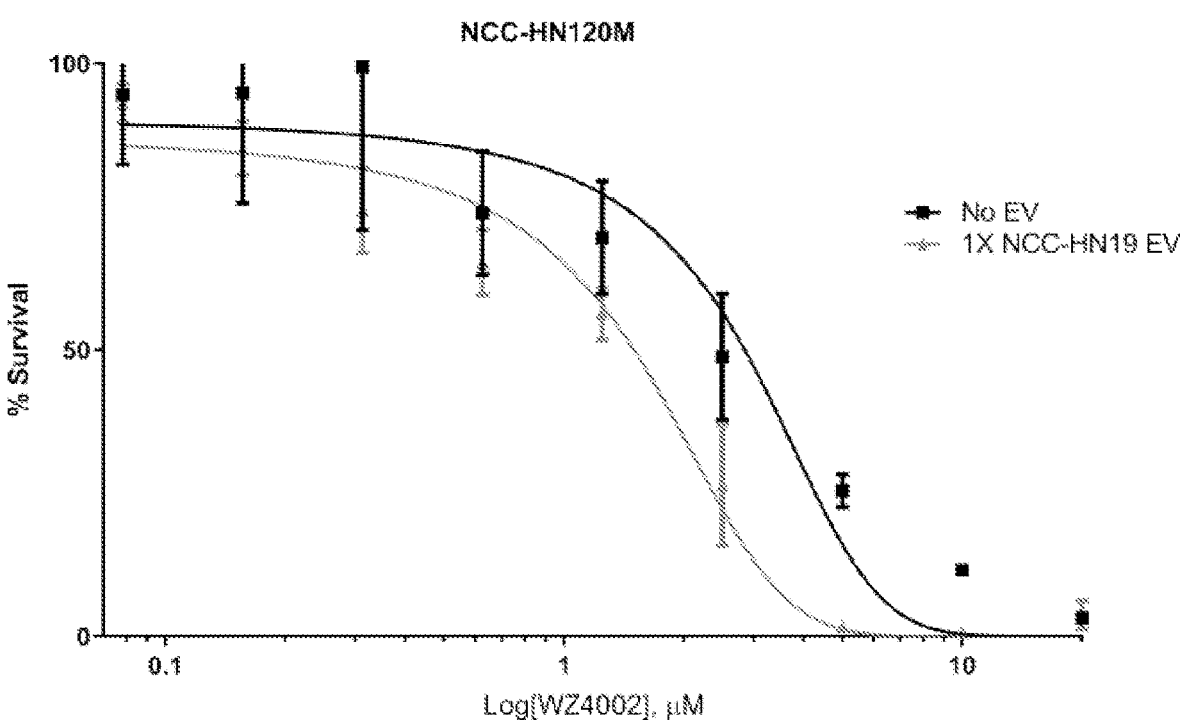
Figure 11B:
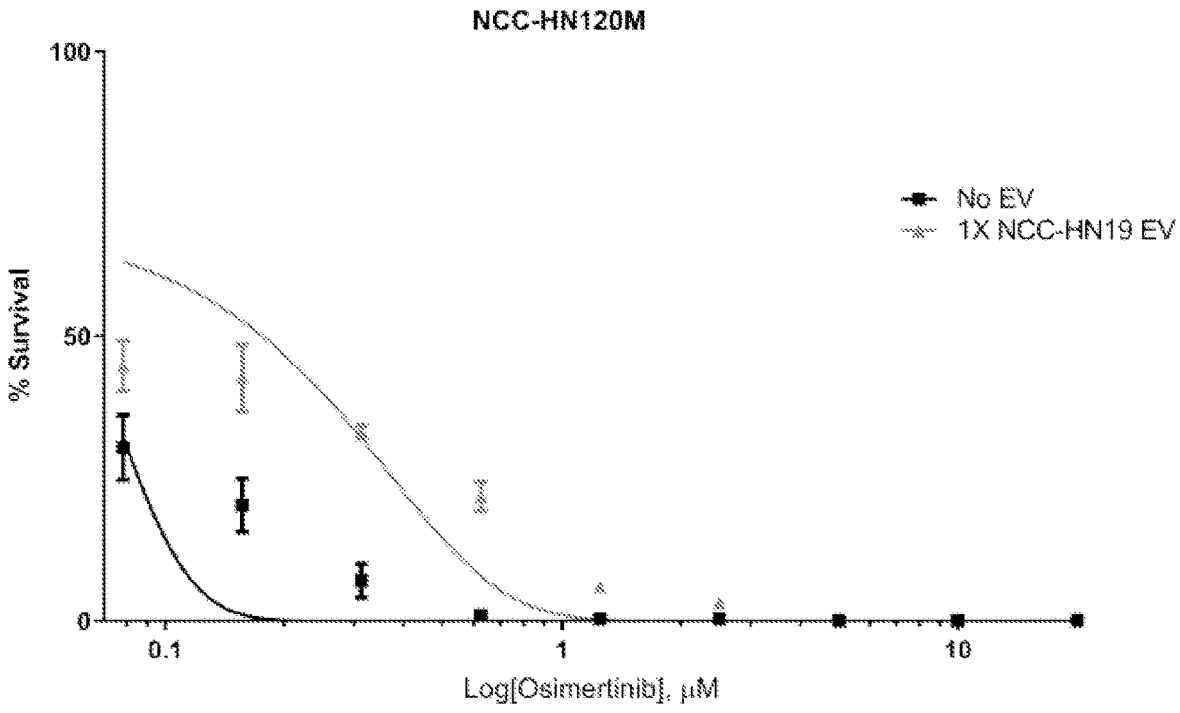
Figure 11C:
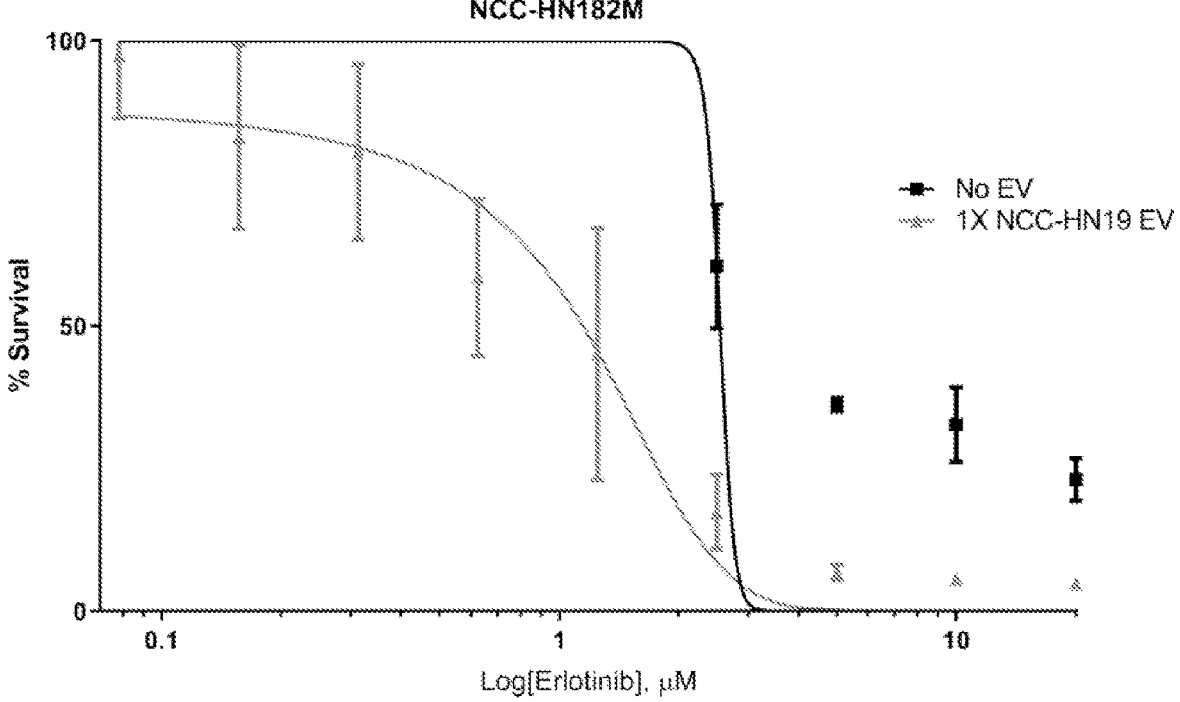
FIG. 11C shows the results of NCC-HN182M cells co-treated with NCC-HN19EV and eight tyrosine kinase inhibitors. Graphs show the percentage of survival of NCC-HN182M cells treated without exosome (No EV) or with exosome from NCC-HN19 cells (1×NCC-HN19EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11C:
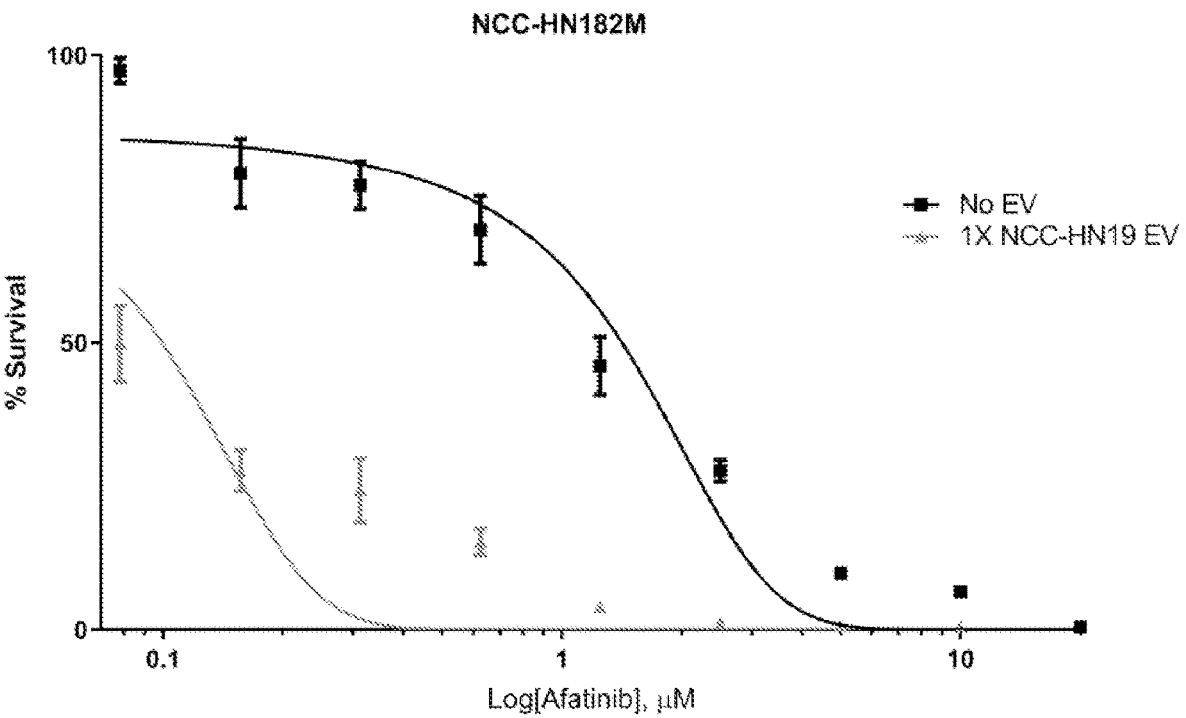
Figure 11C:
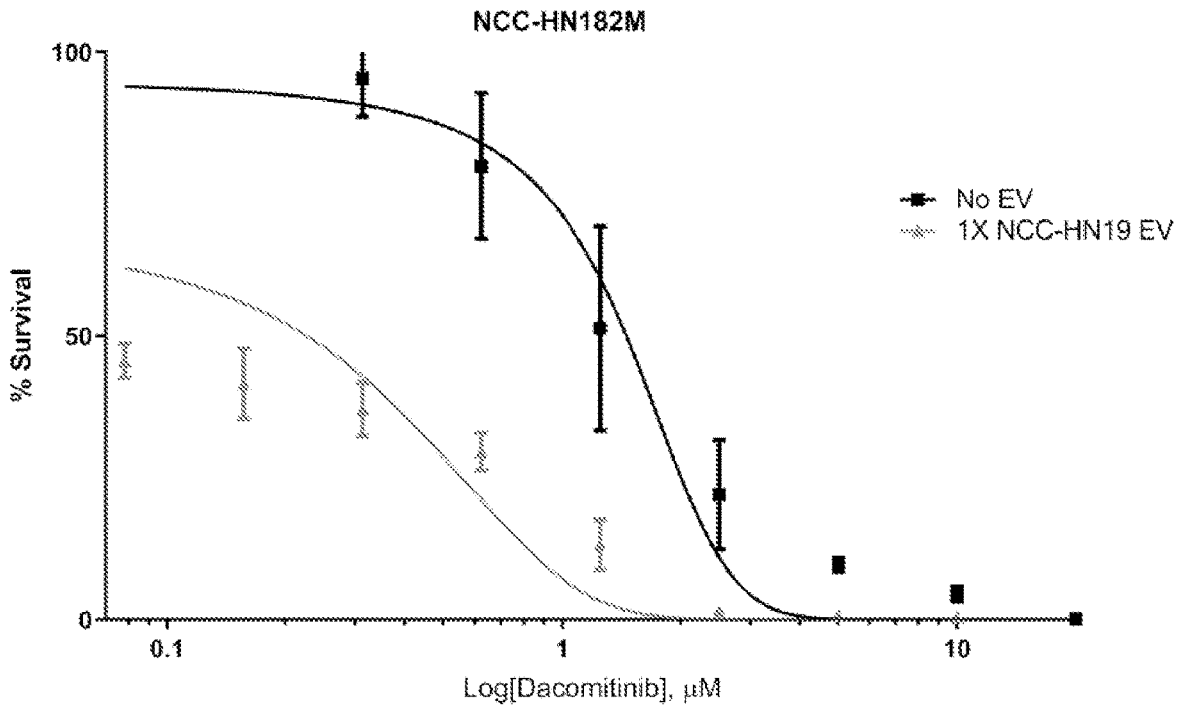
Figure 11C:
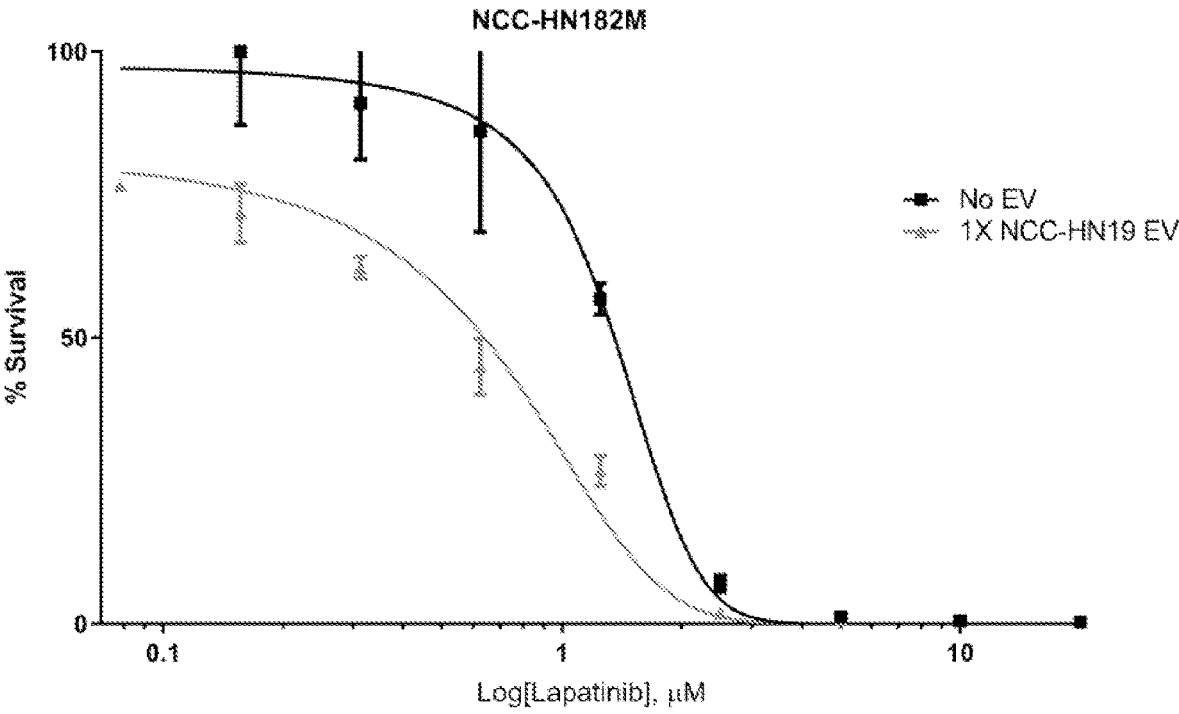
Figure 11C:
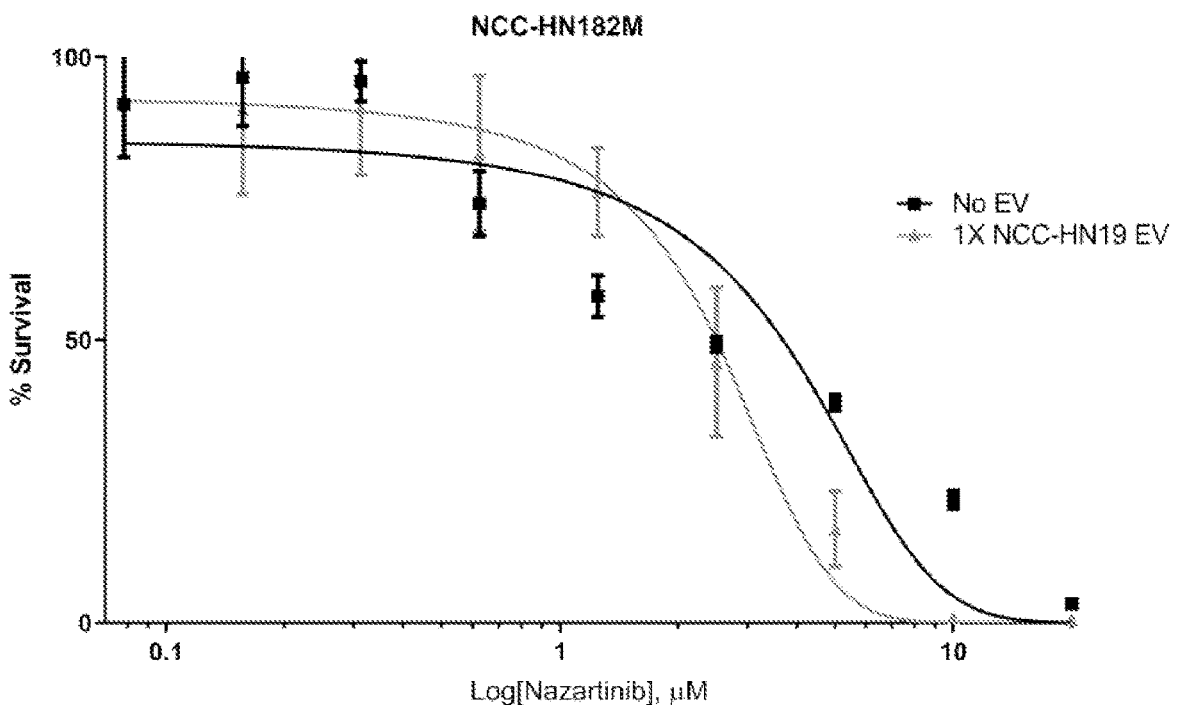
Figure 11C:
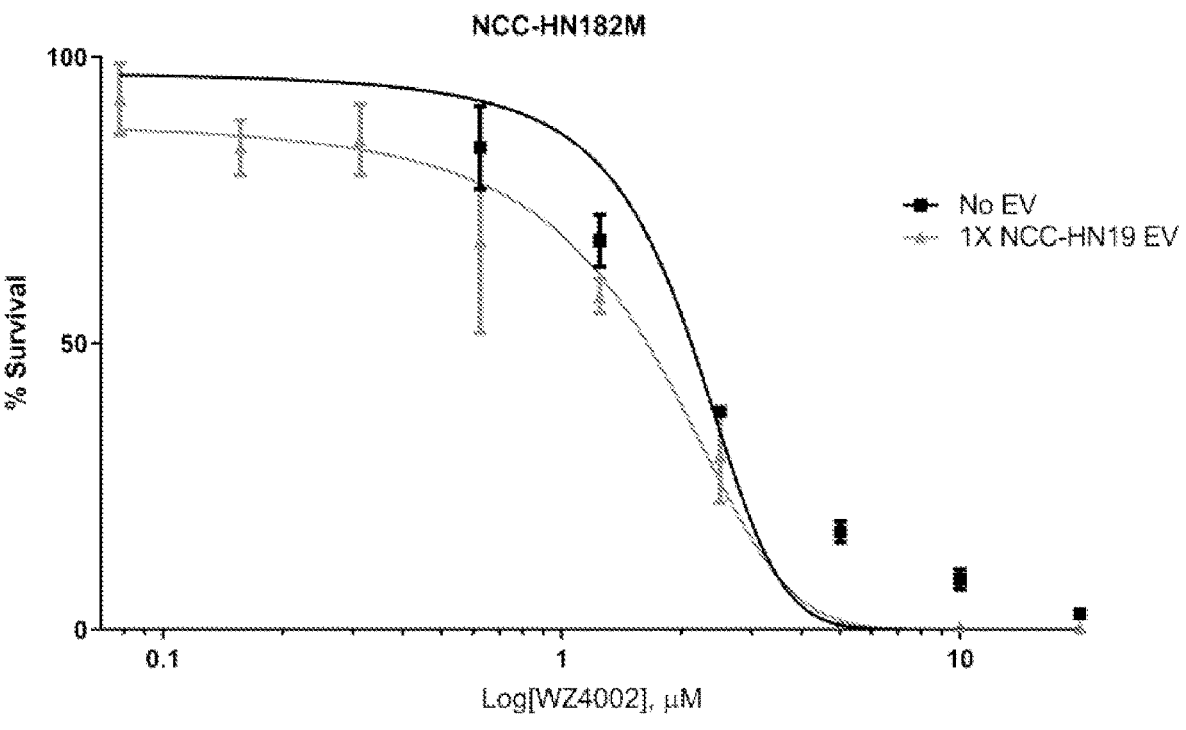
Figure 11C:
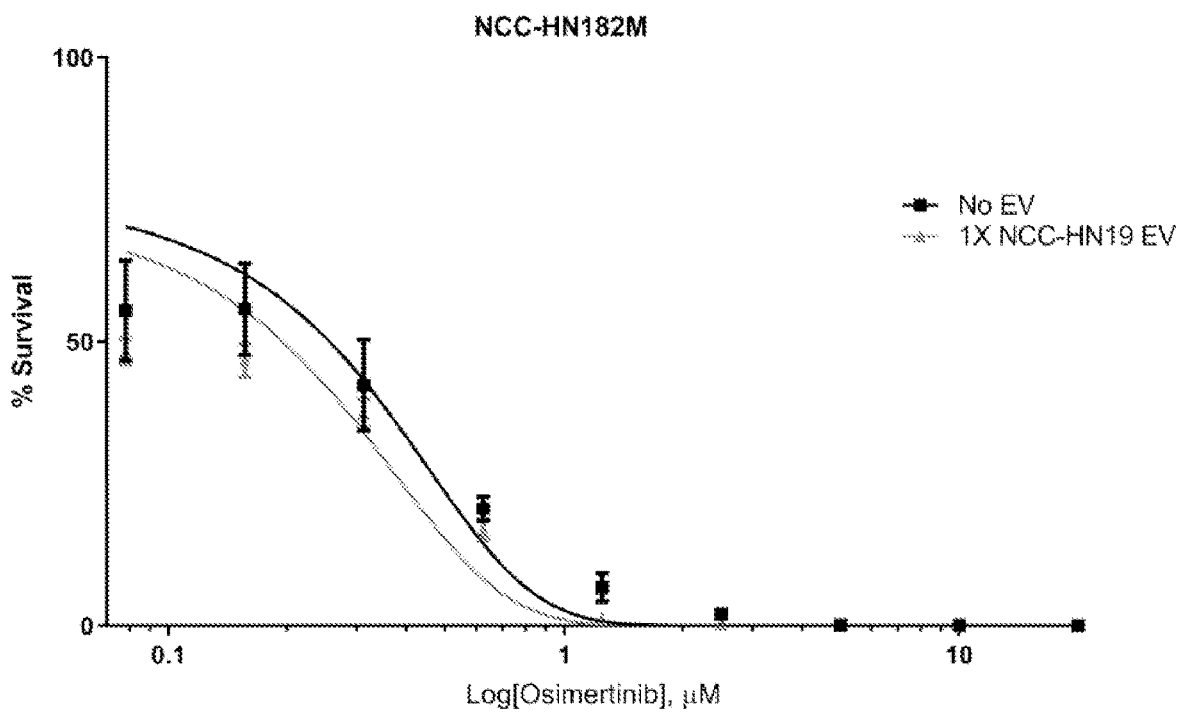
Figure 11D:
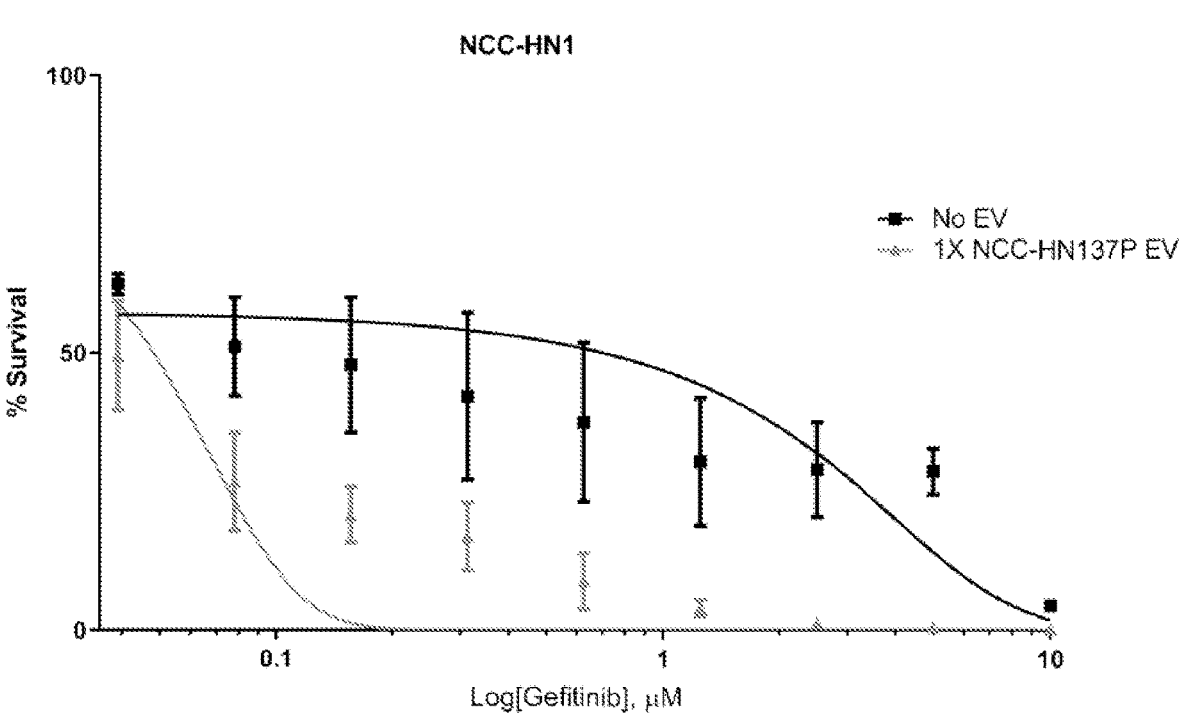
FIG. 11D shows the results of NCC-HN1 cells co-treated with NCC-HN137EV and eight tyrosine kinase inhibitors. Graphs show the percentage of survival of NCC-HN1 cells treated without exosome (no EV) or with exosome from NCC-HN137P cells (1×NCC-HN137P EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11D:
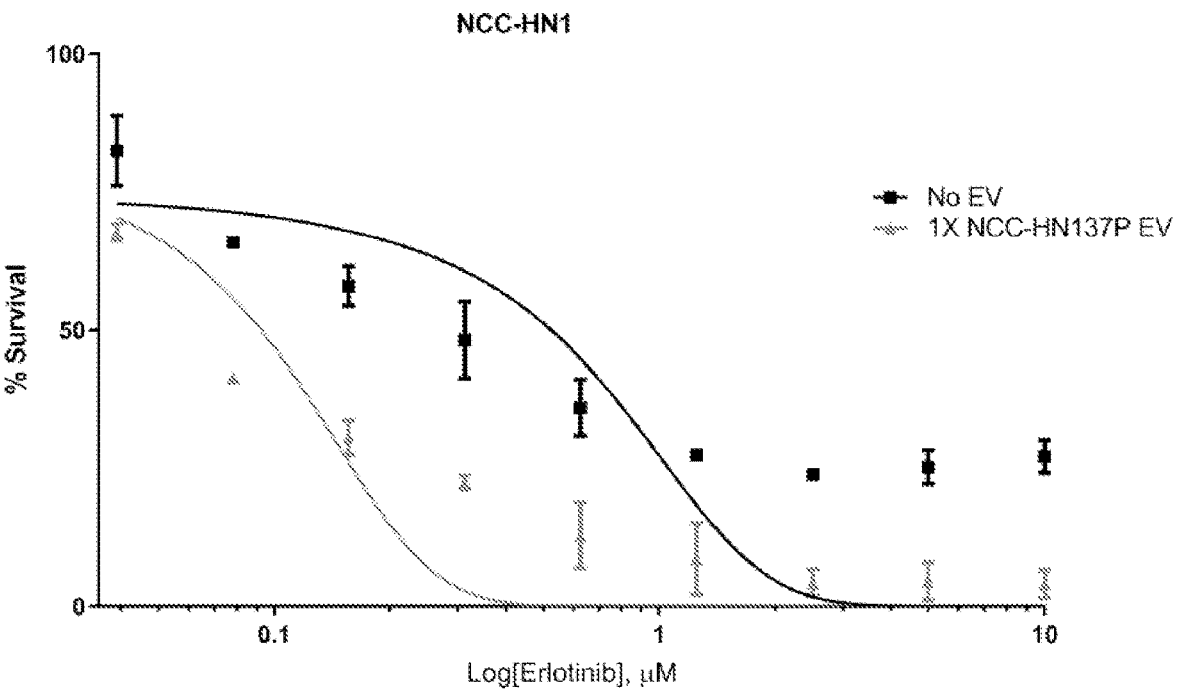
Figure 11D:
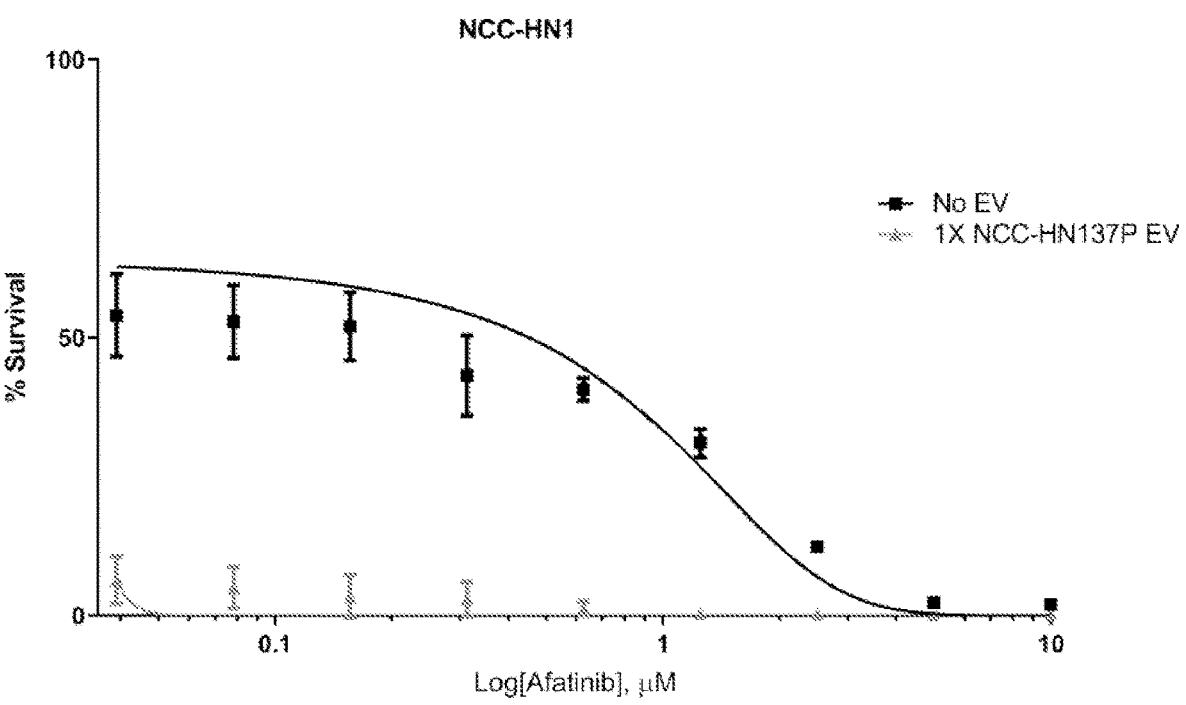
Figure 11D:
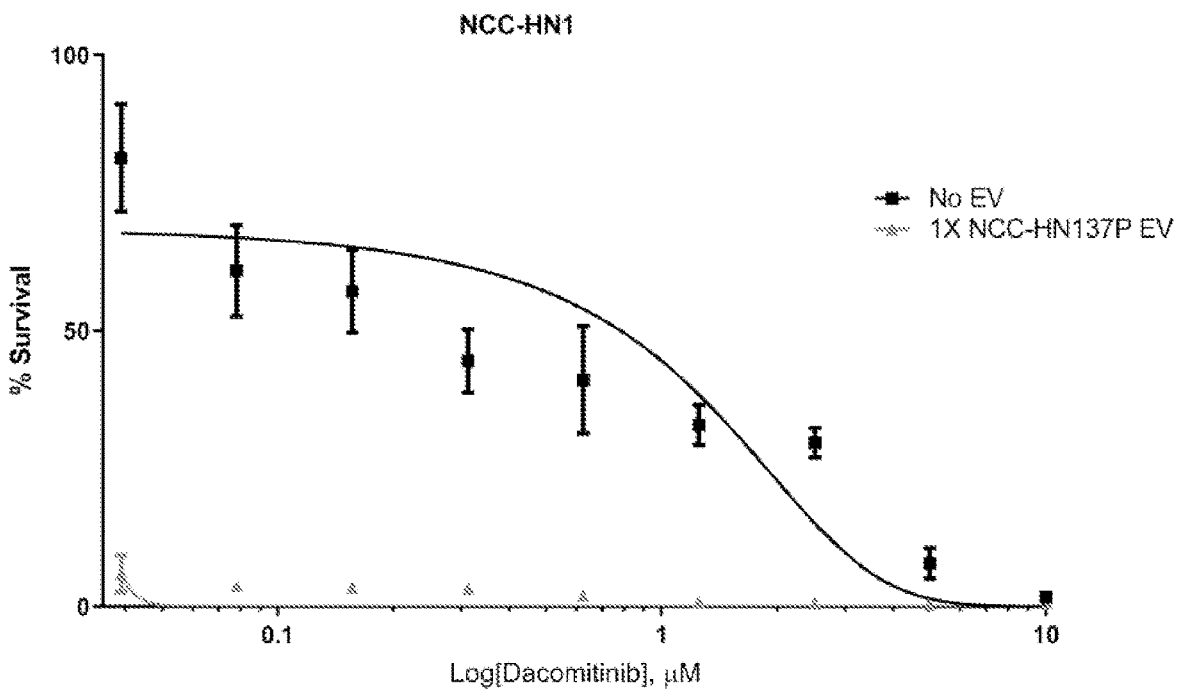
Figure 11D:
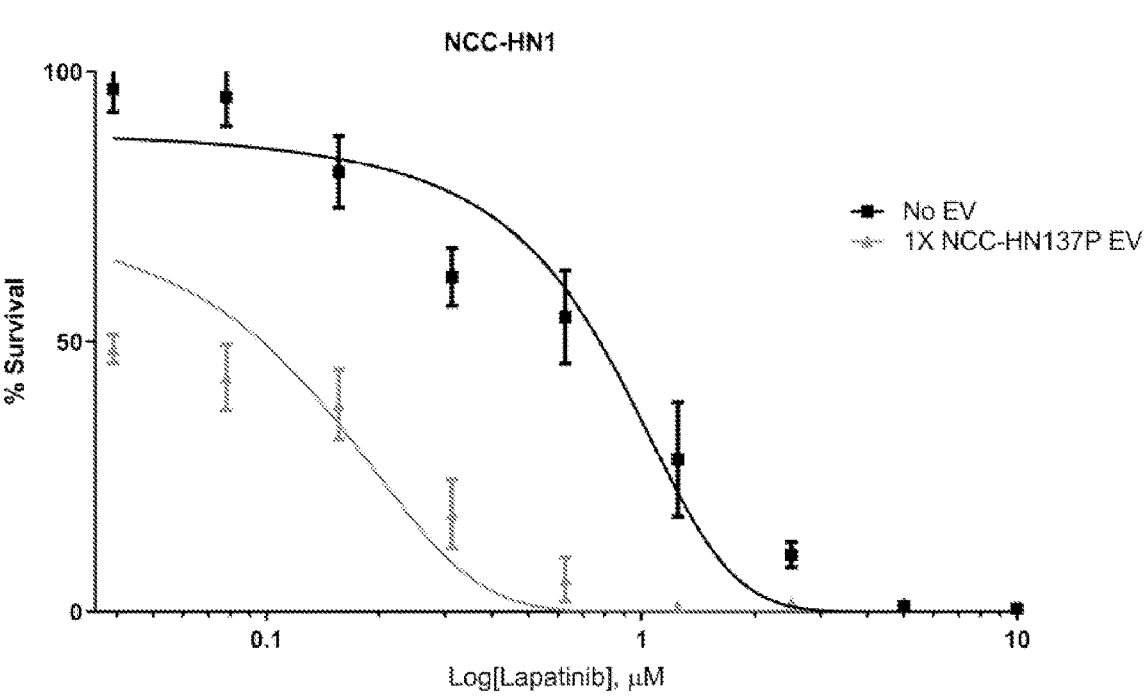
Figure 11D:
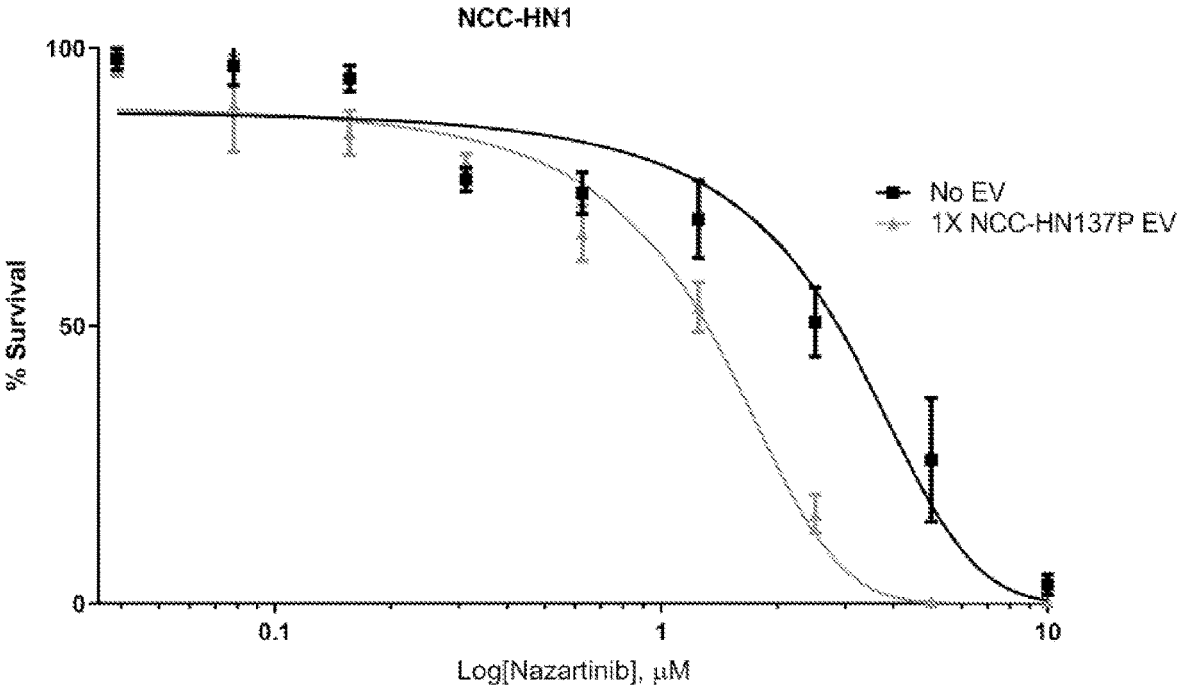
Figure 11D:
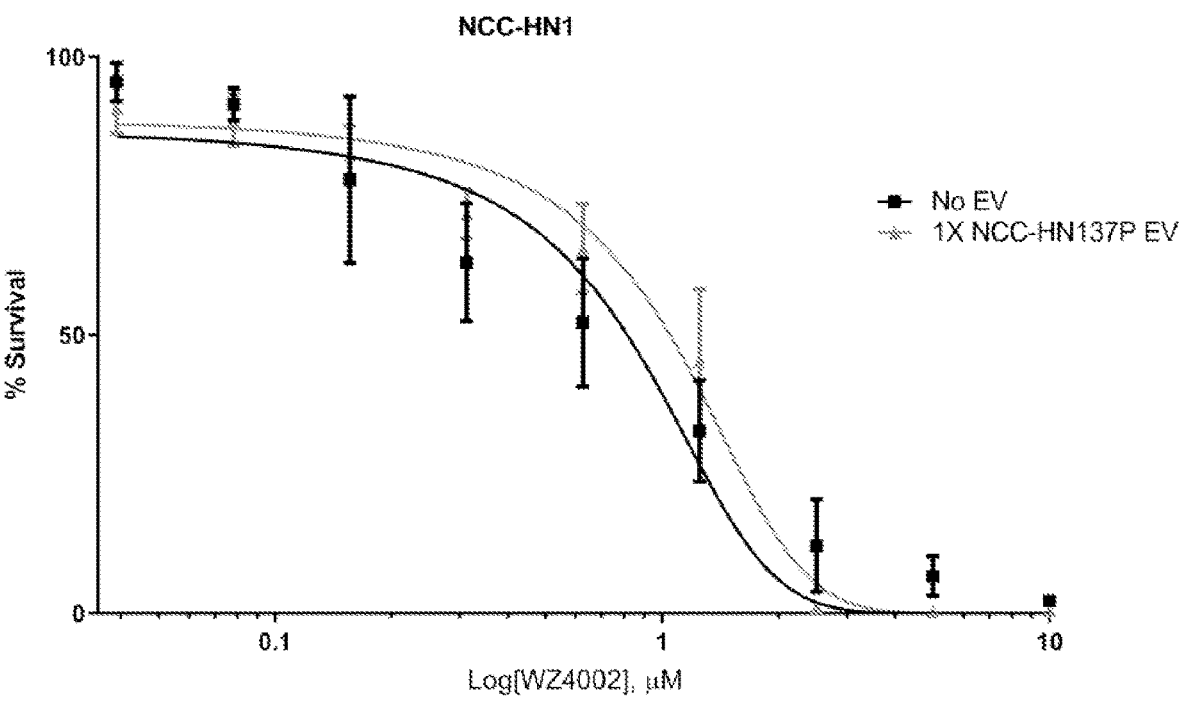
Figure 11D:
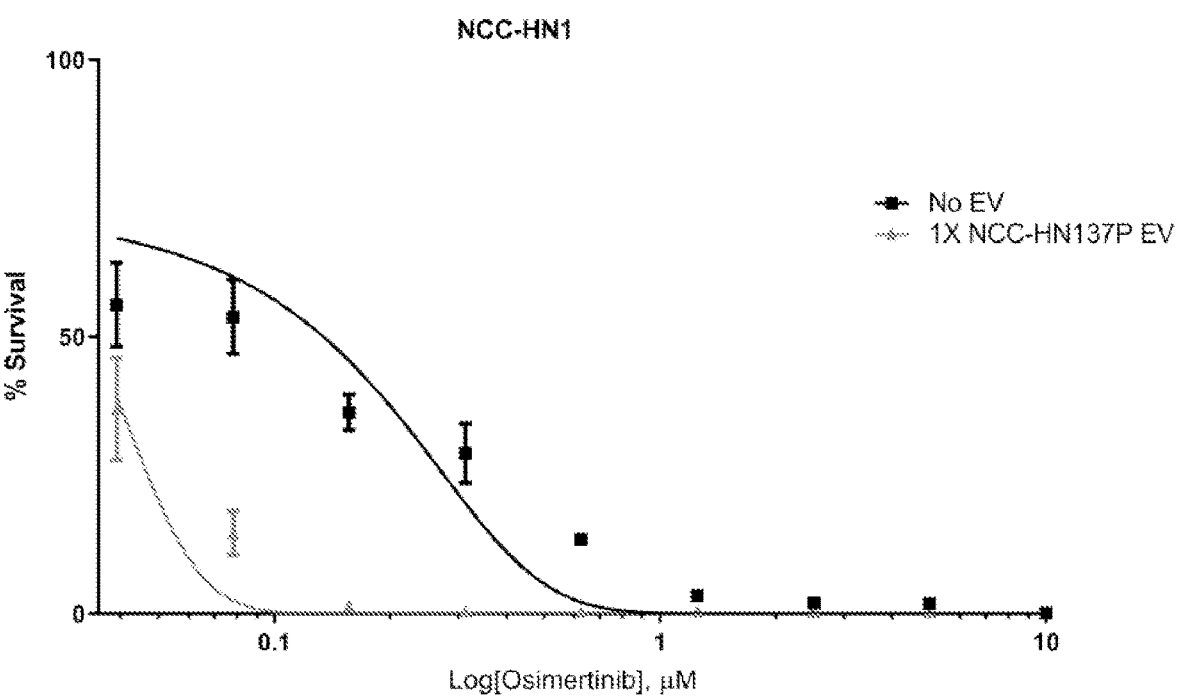
Figure 11E:
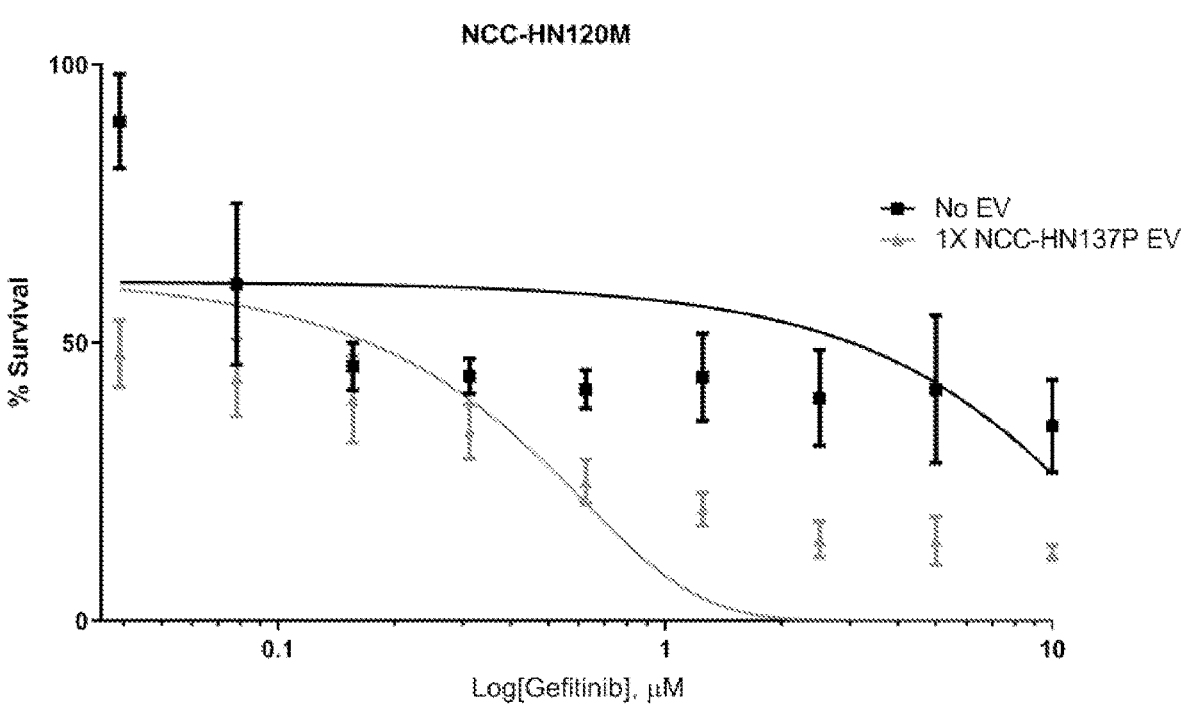
FIG. 11E shows the results of NCC-HN120M cells co-treated with NCC-HN137EV and eight tyrosine kinase inhibitors. Graphs show the percentage of survival of NCC-HN120M cells treated without exosome (no EV) or with exosome from NCC-HN137P cells (1×NCC-HN137P EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11E:
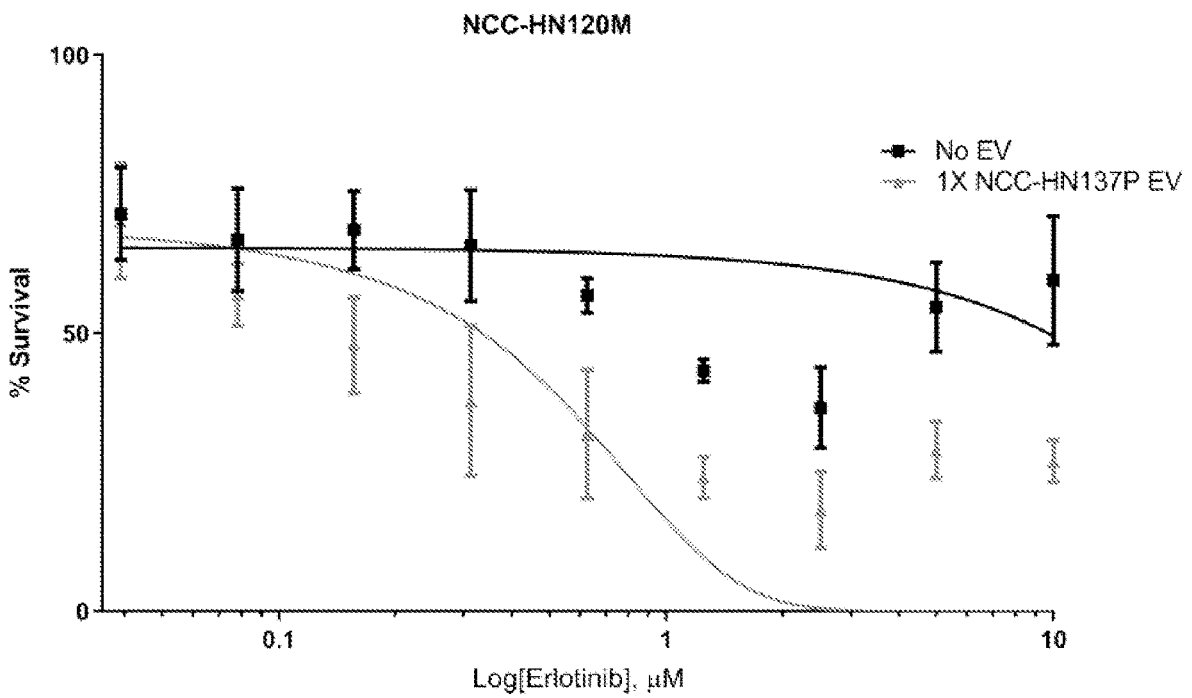
Figure 11E:
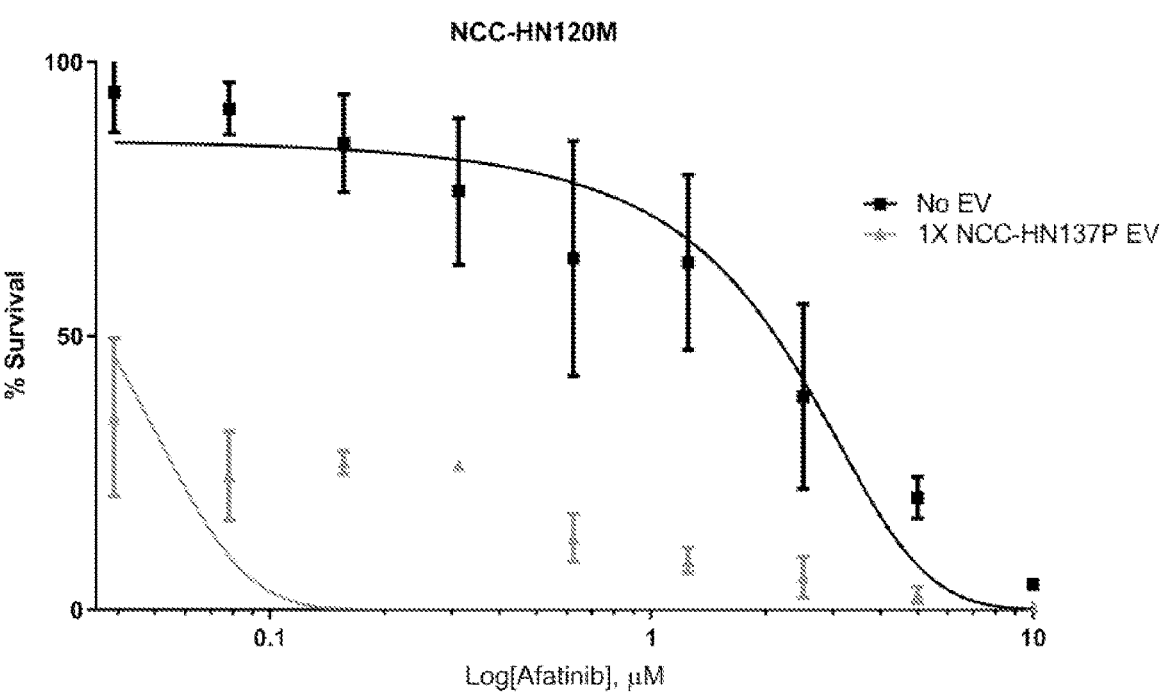
Figure 11E:
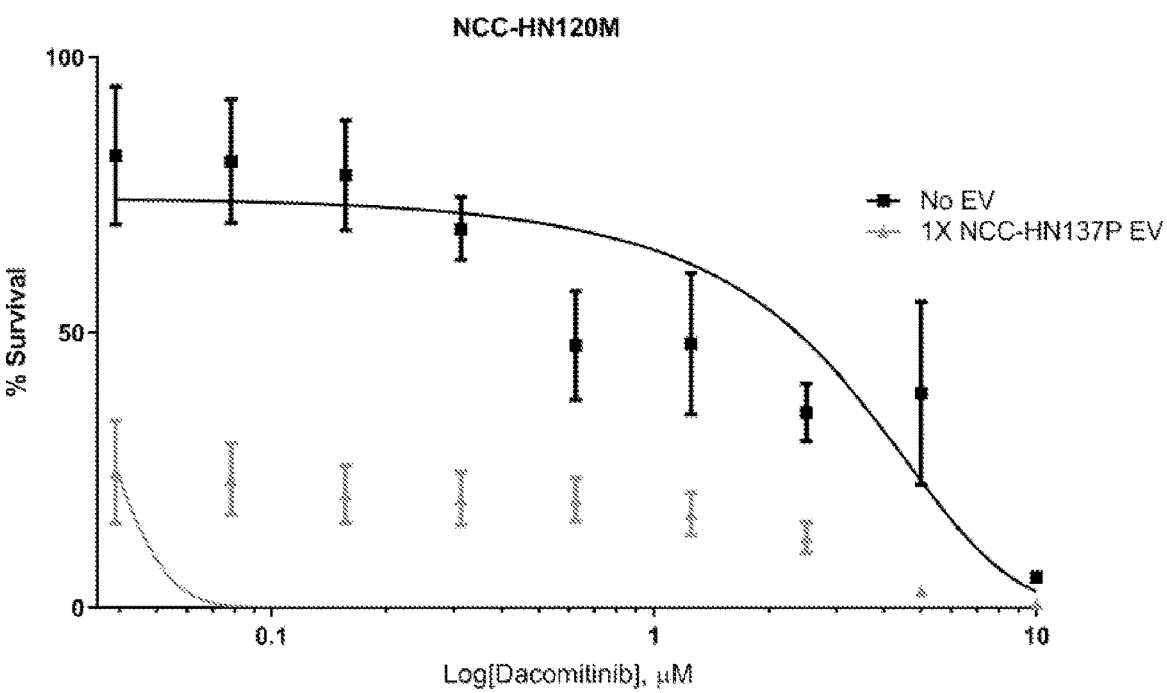
Figure 11E:
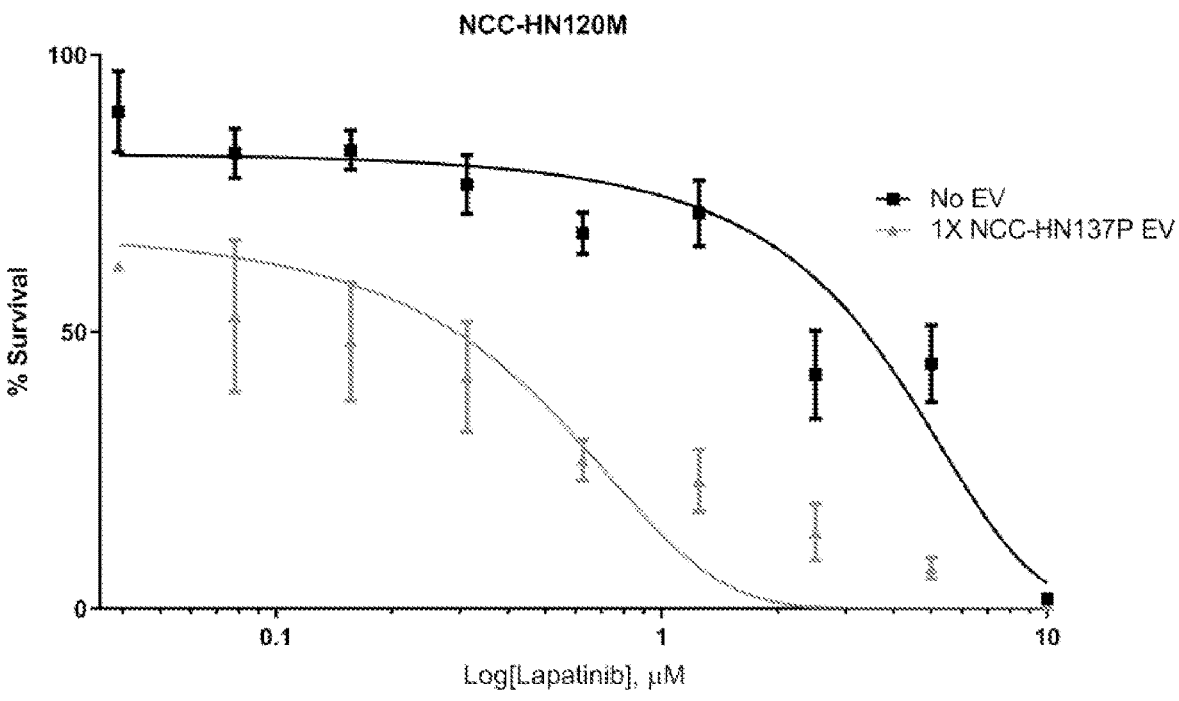
Figure 11E:
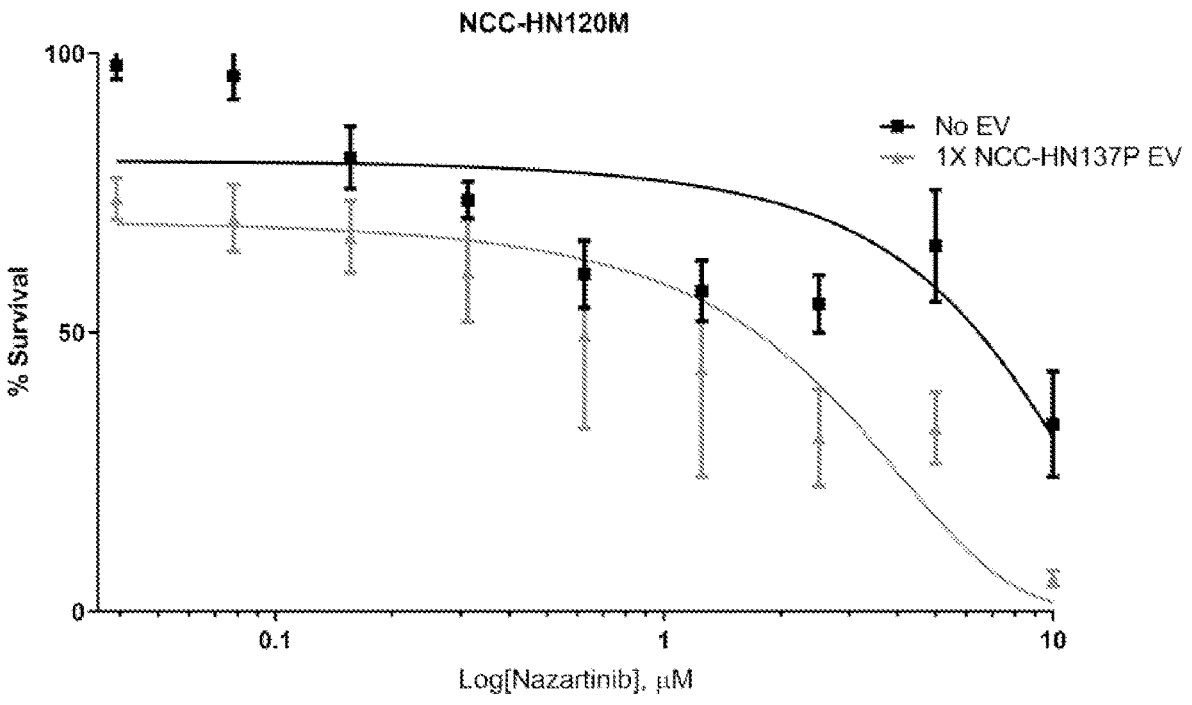
Figure 11E:
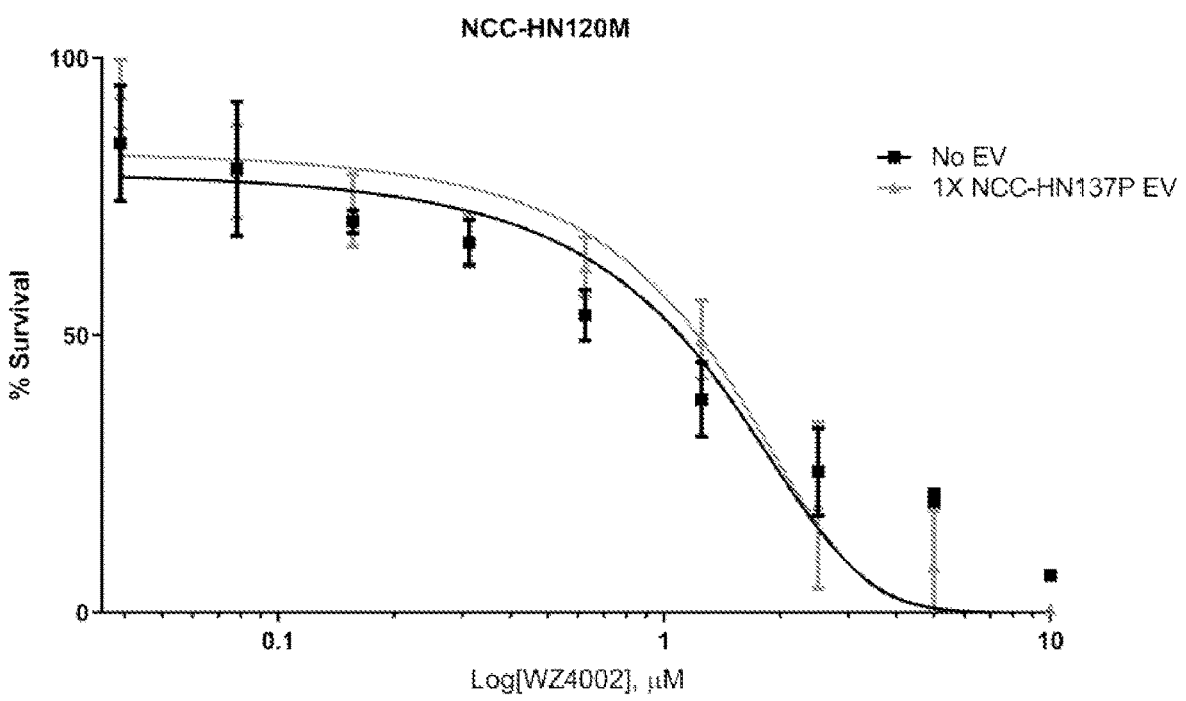
Figure 11E:
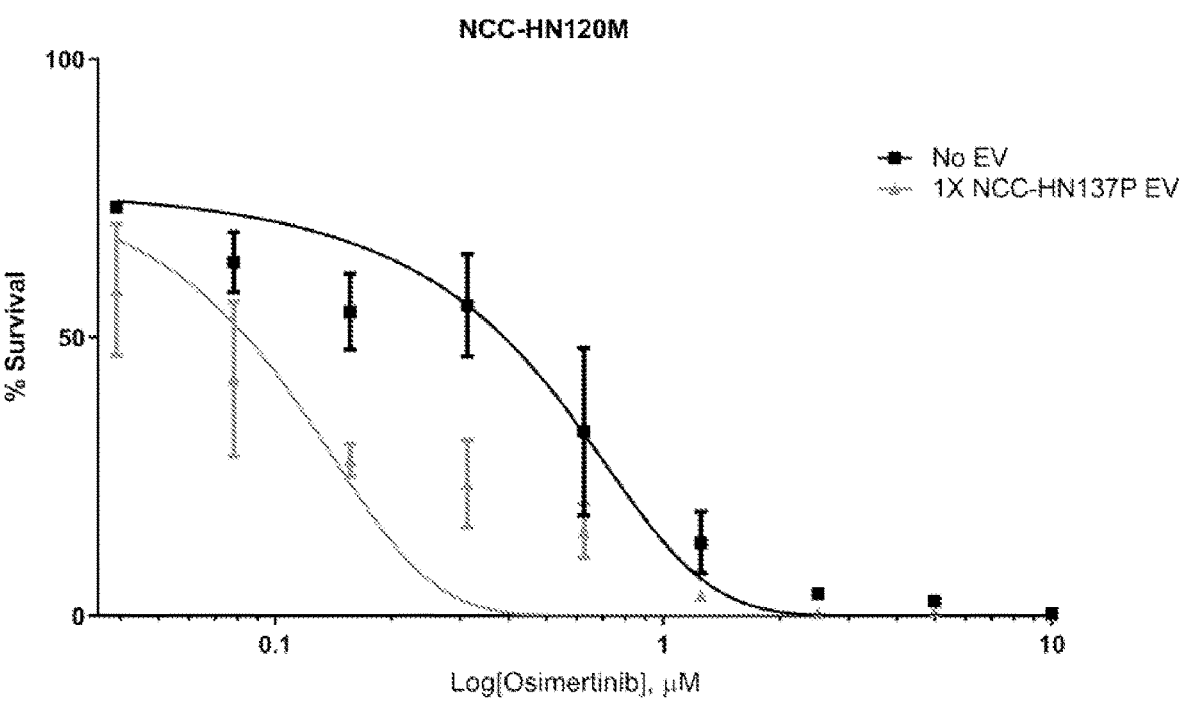
Figure 11F:
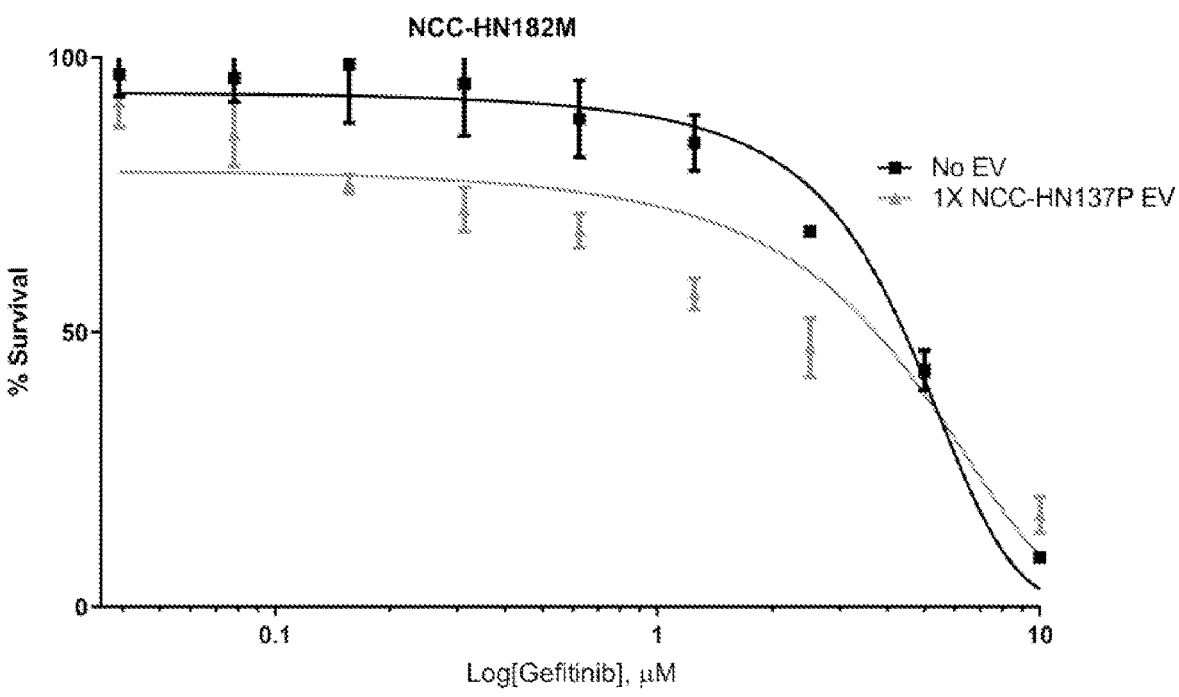
FIG. 11F shows the results of NCC-HN182M cells co-treated with NCC-HN137EV and eight tyrosine kinase inhibitors. Graphs show the percentage of survival of NCC-HN182M cells treated without exosome (no EV) or with exosome from NCC-HN137P cells (1×NCC-HN137P EV) in combination with first generation tyrosine kinase inhibitors (gefitinib or erlotinib), second generation tyrosine kinase inhibitors (afatinib or dacomitinib) and third generation tyrosine kinase inhibitors (lapatinib, nazartinib, WZ4002 or osimertinib).
Figure 11F:
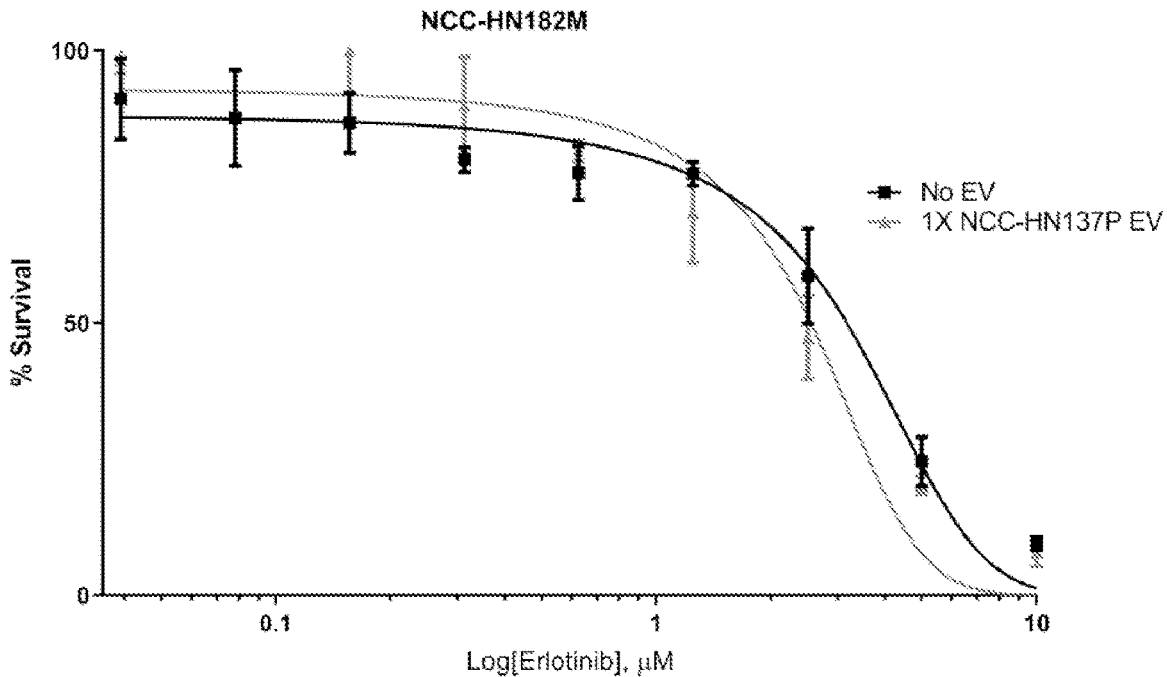
Figure 11F:
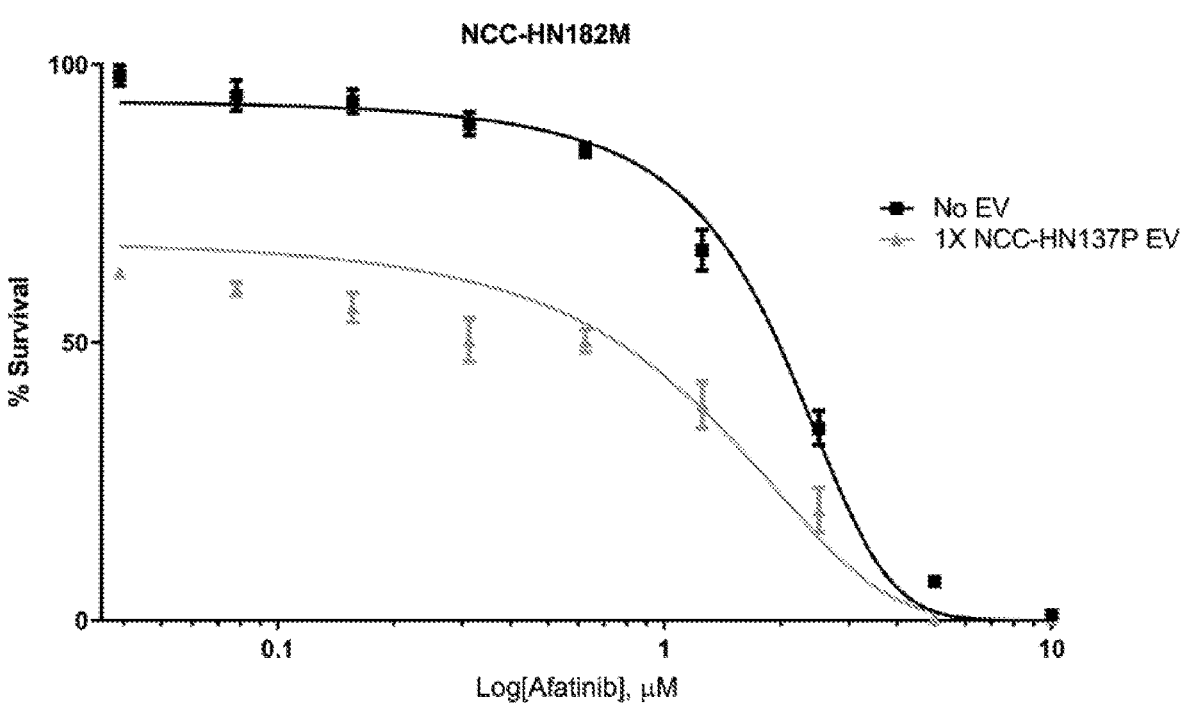
Figure 11F:
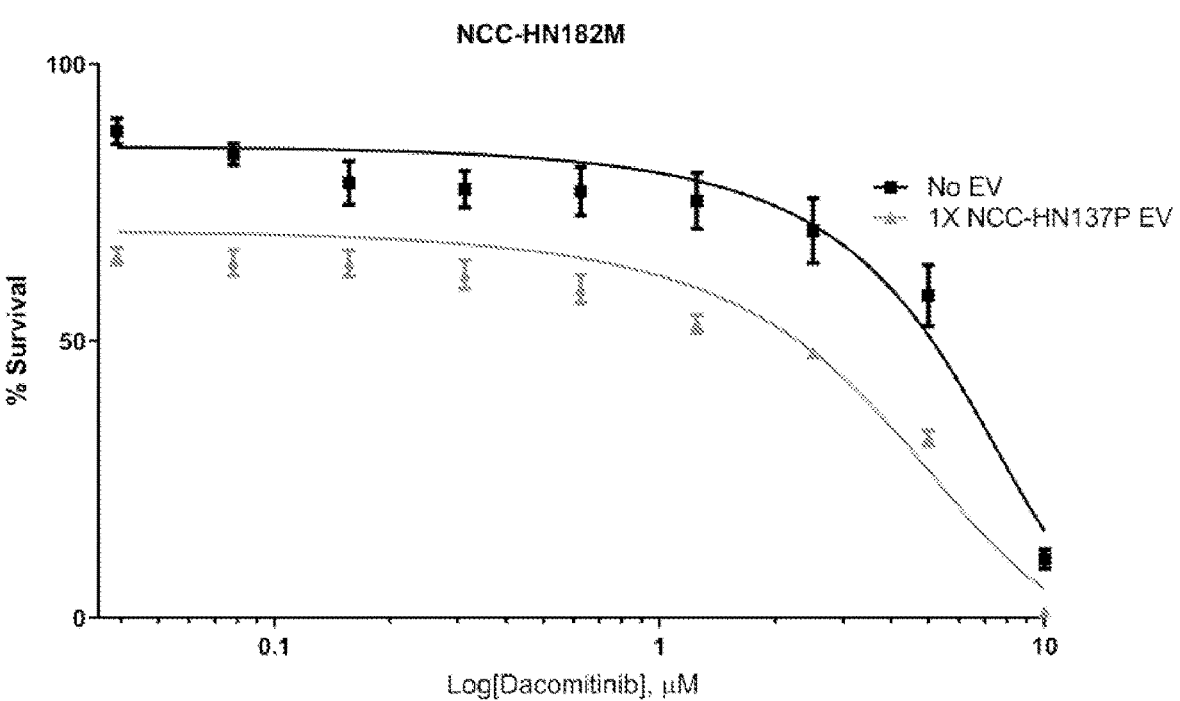
Figure 11F:
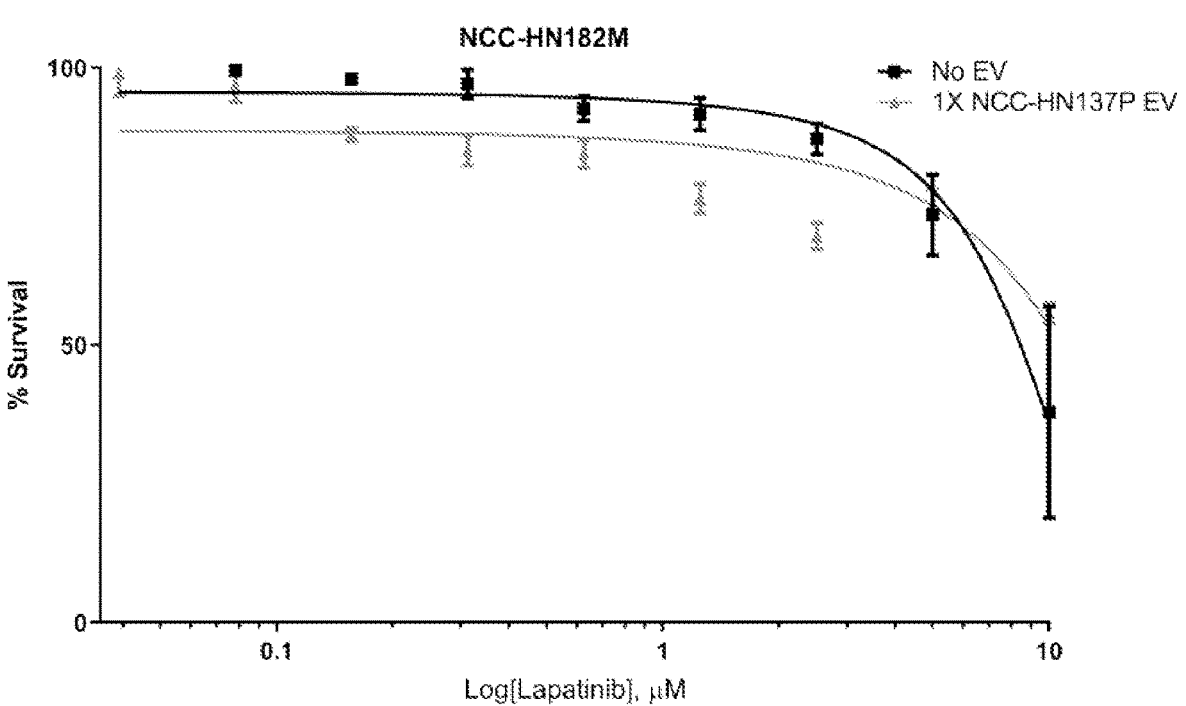
Figure 11F:
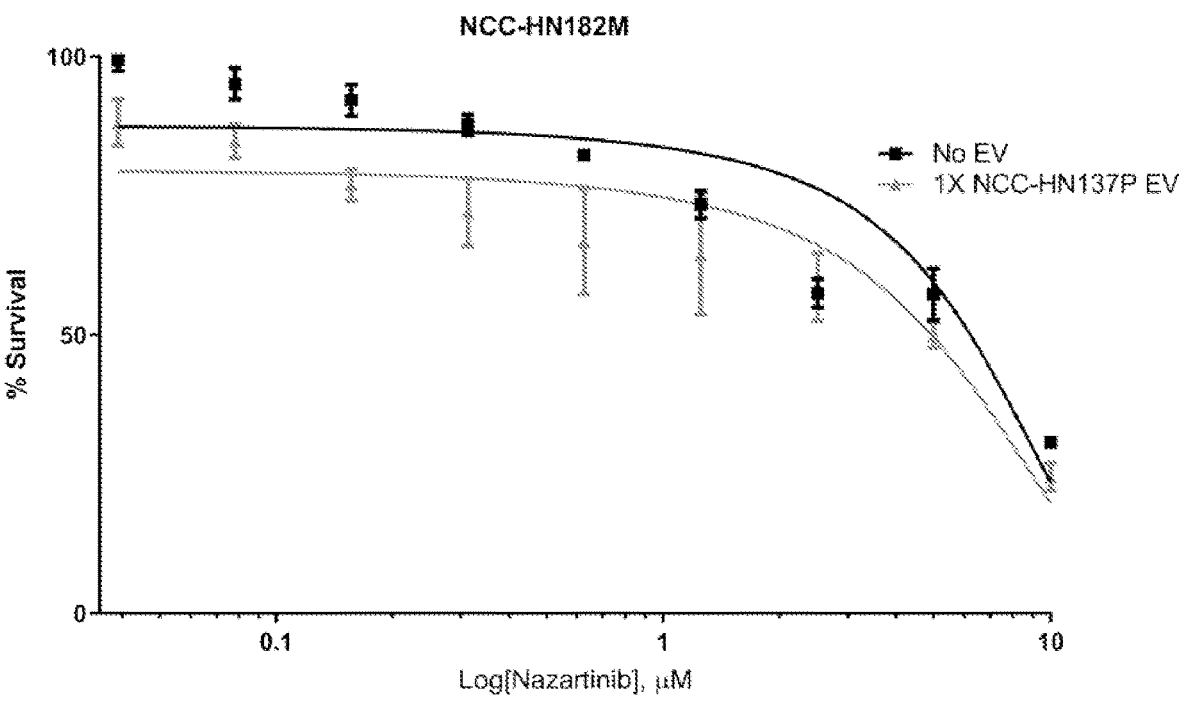
Figure 11F:
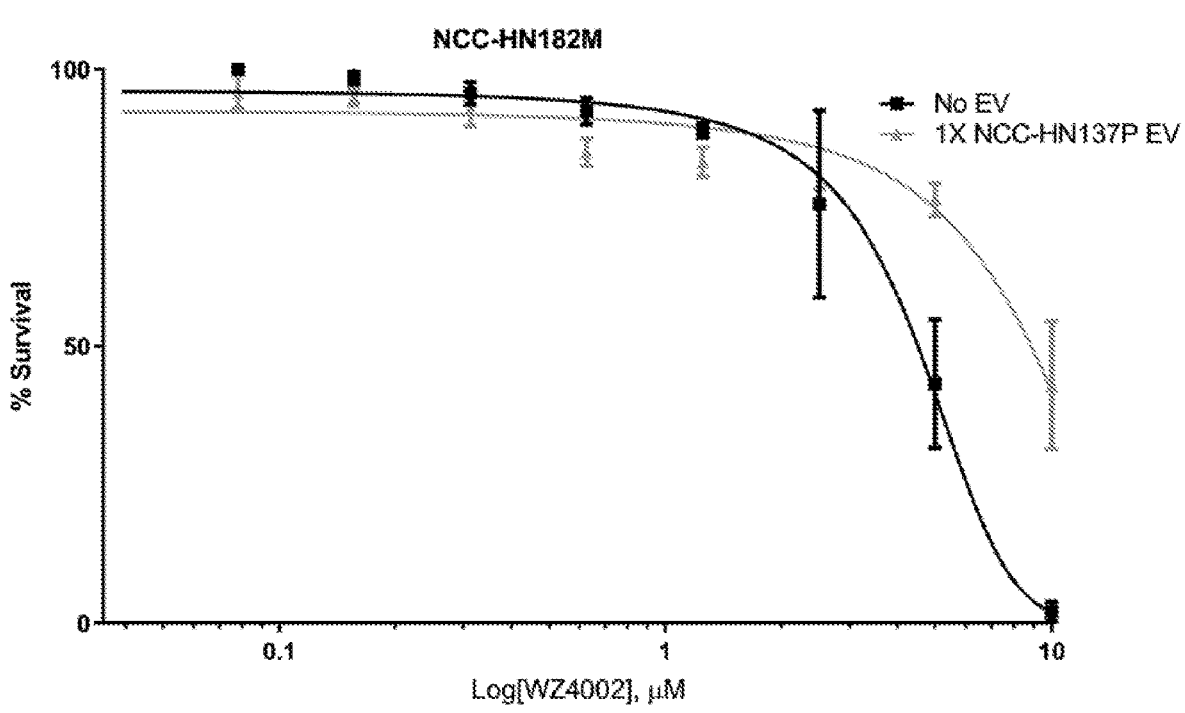
Figure 11F:
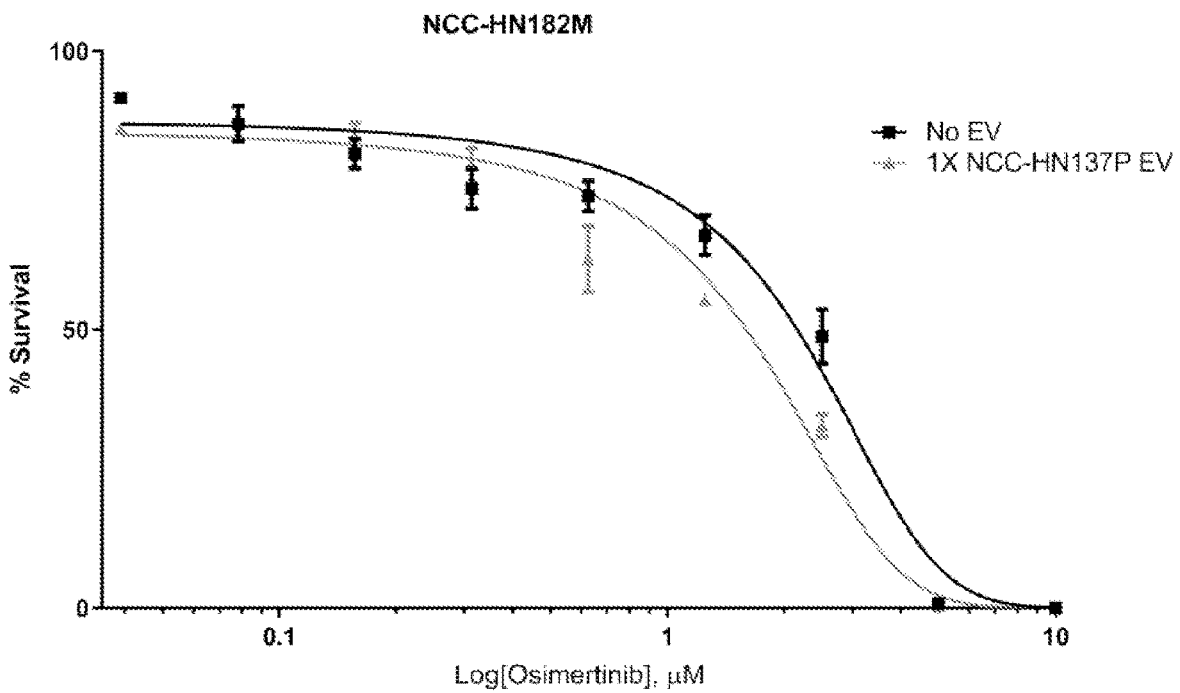
Figure 11H:
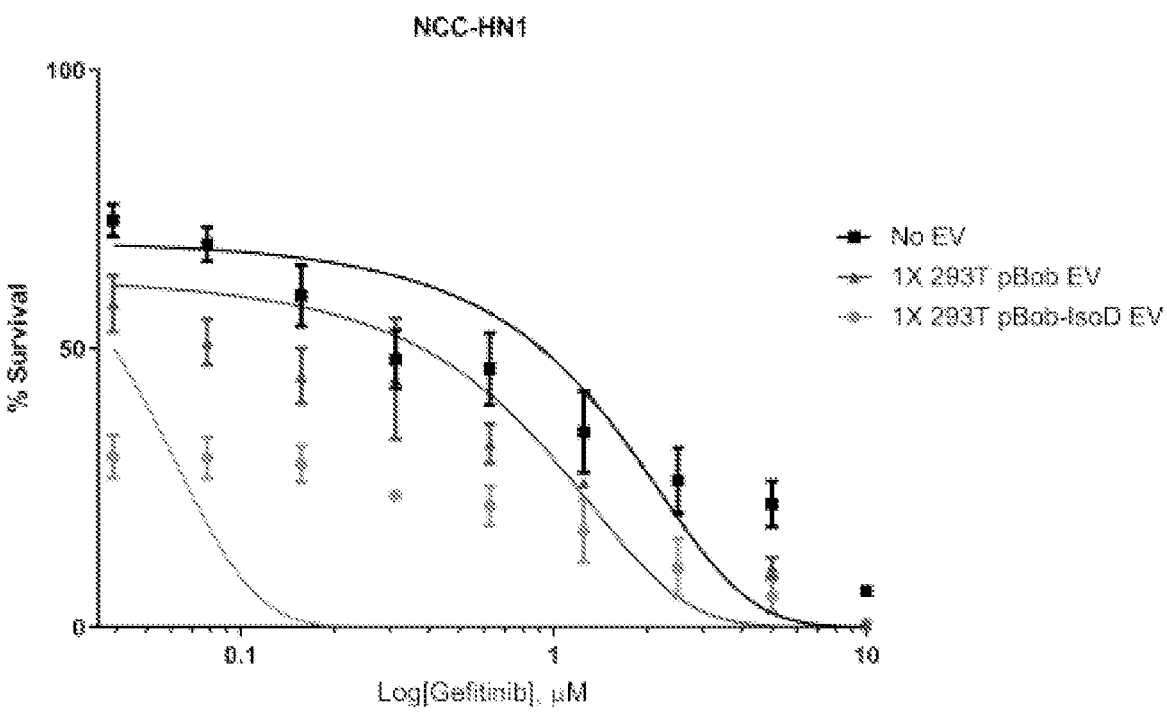
FIG. 11H shows the results of NCC-HN1 and NCC-HN120M cells co-treated with first (gefitinib) or second (afatinib & dacomitinib) generation tyrosine kinase inhibitors and exosome isolated from vector control or Isoform D expressing 293T cells. Graphs show the percentage of survival of NCC-HN1 and NCC-HN120M cells treated without exosome (no EV) or with exosome from 293T control cells (1×293T pBob EV) or exosomes from 293T cells over-expressing Isoform D (1×293T pBob-IsoD EV) in combination with first generation tyrosine kinase inhibitor (gefitinib), and second generation tyrosine kinase inhibitors (afatinib or dacomitinib). This data collectively shows that EVs collected from cells (HN19 and HN137P), that have endogenously high EGFR Isoform D expression, when applied to various TKI-resistant HNSCC cell lines (HN1, HN120M and HN182M), is able to sensitise the latter to first, second and third generation tyrosine kinase inhibitors (TKIs). Similarly, when EVs are collected from non-HNSCC cell line, 293T, with Isoform D being ectopically expressed, these EVs can sensitise the same TKI-resistant HNSCC cell lines to first, second and third generation tyrosine kinase inhibitors (TKIs).
Figure 11H:
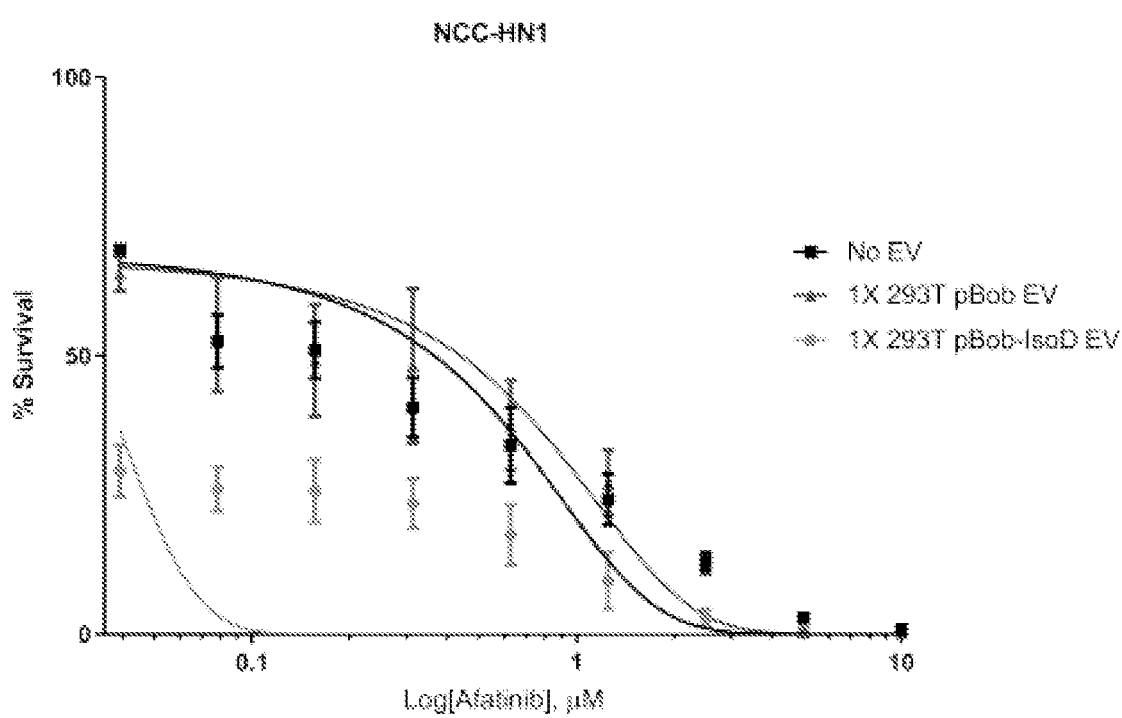
Figure 11H:
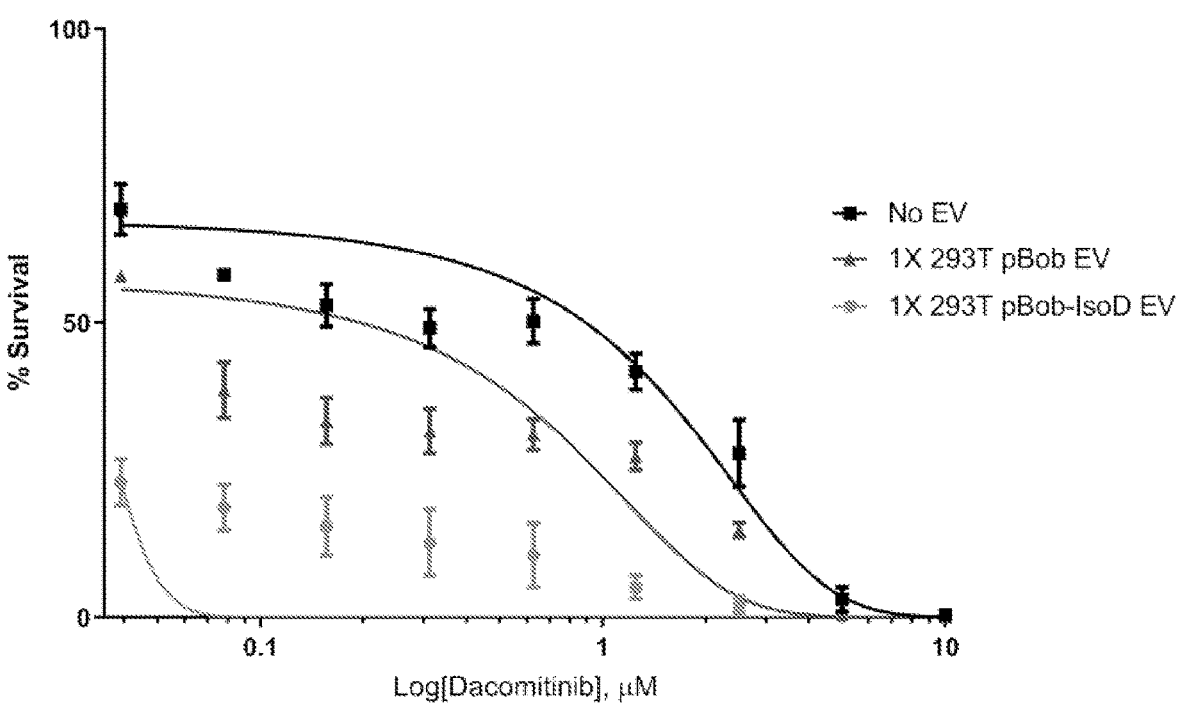
Figure 11H:
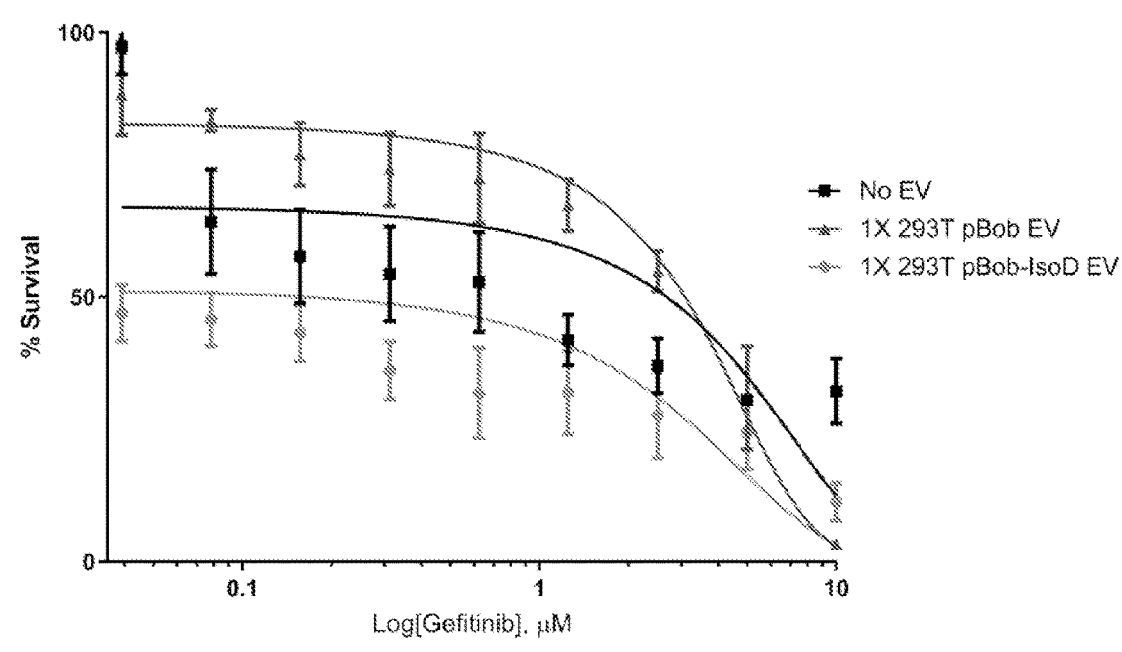
Figure 11H:
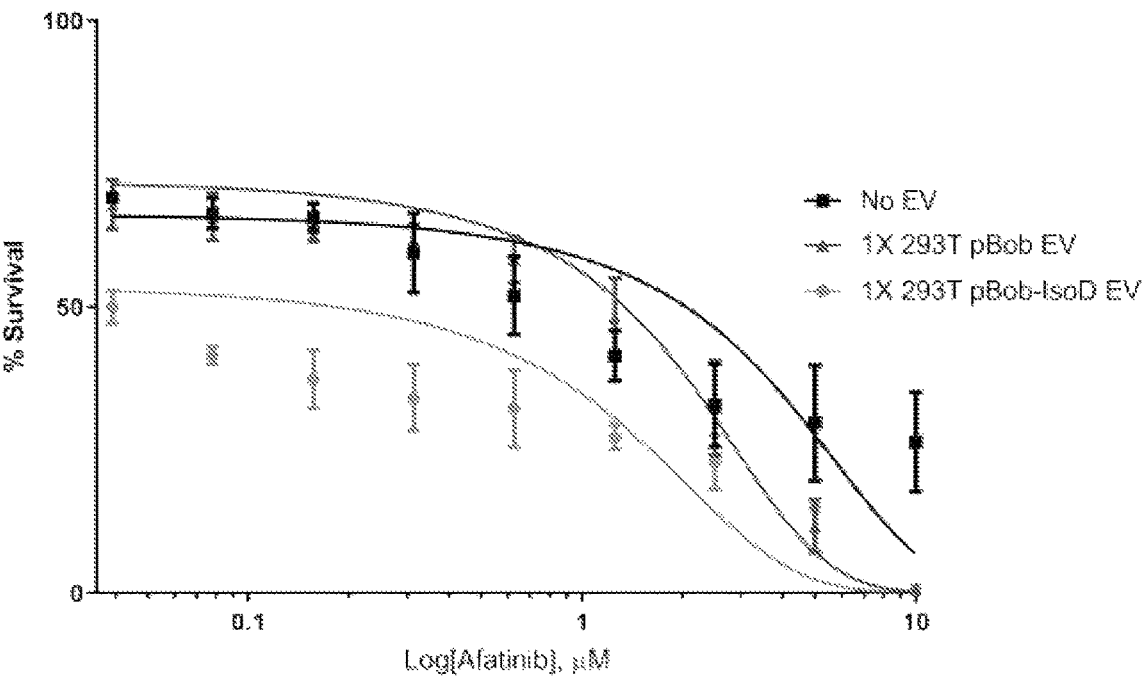
Figure 11H:
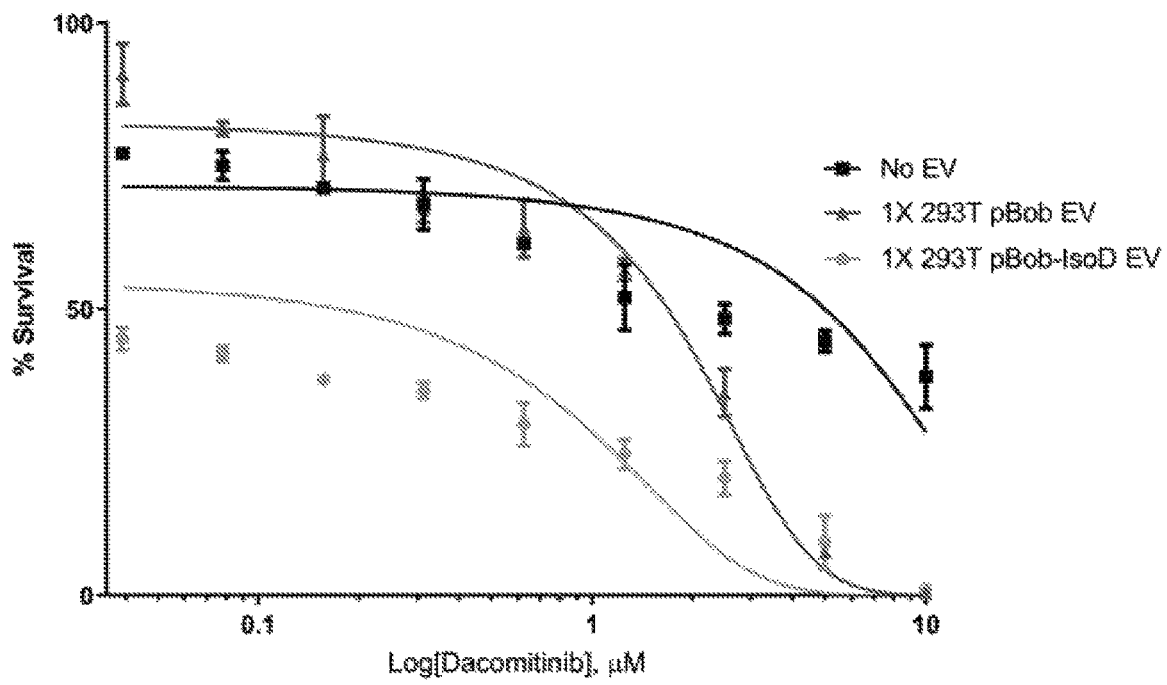
Figure 12A:
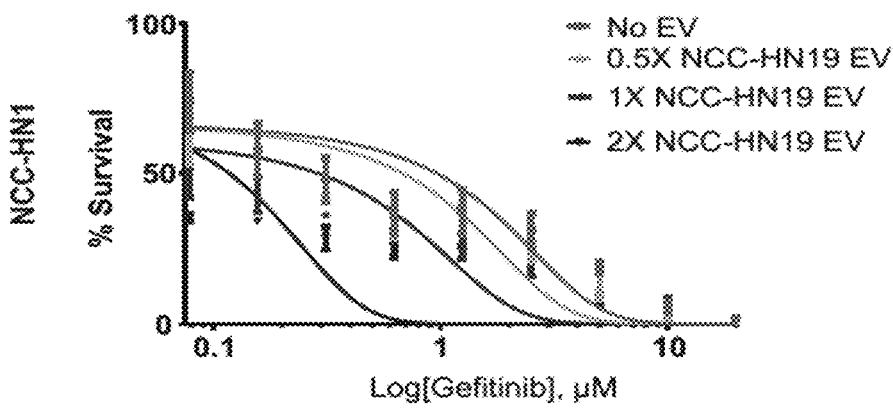
FIG. 12A shows the results of NCC-HN1, NCC-HN120M and NCC-HN182M cells co-treated with EV from NCC-HN19 and gefitinib, afatinib or dacomitinib. Graphs show percentage survival of NCC-HN1, NCC-HN120M and NCC-HN182M cells treated without exosomes (No EV) or with 0.5× (0.5× NCC-HN19 EV), 1× (1×NCC-HN19 EV) or 2× (2×NCC-HN19 EV) relative quantity of exosomes from NCC-HN19 cells in combination with a first generation tyrosine kinase inhibitor (gefitinib) or second generation tyrosine kinase inhibitors (afatinib or dacomitinib).
Figure 12A:
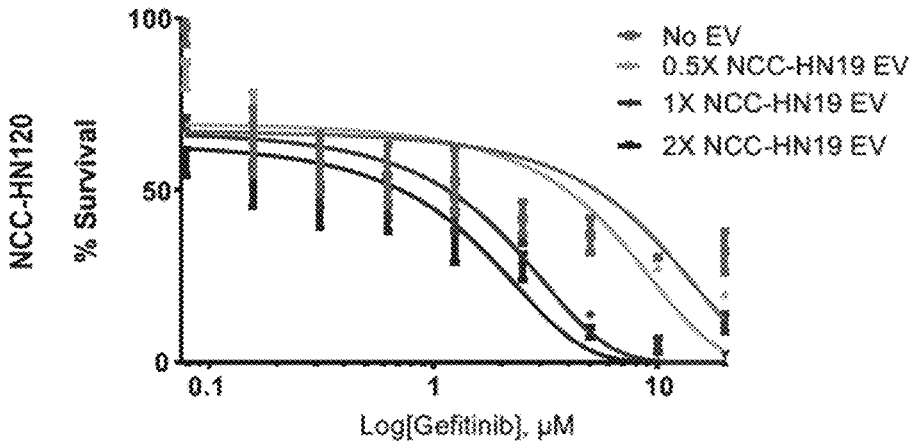
Figure 12A:
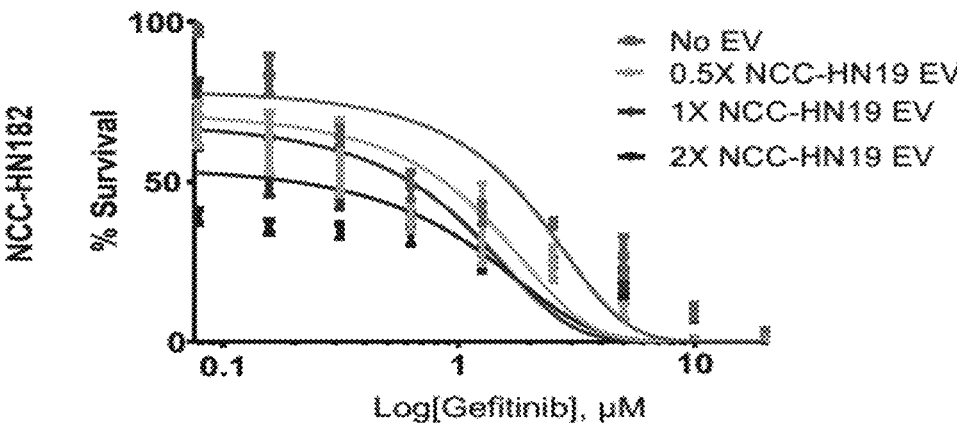
Figure 12A:
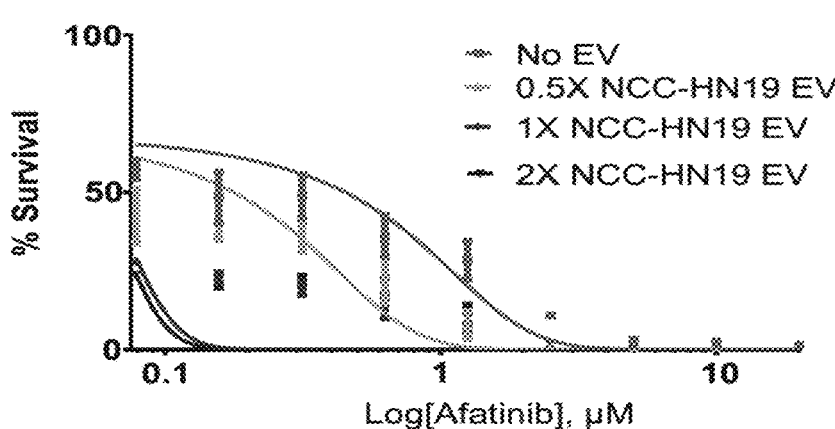
Figure 12A:
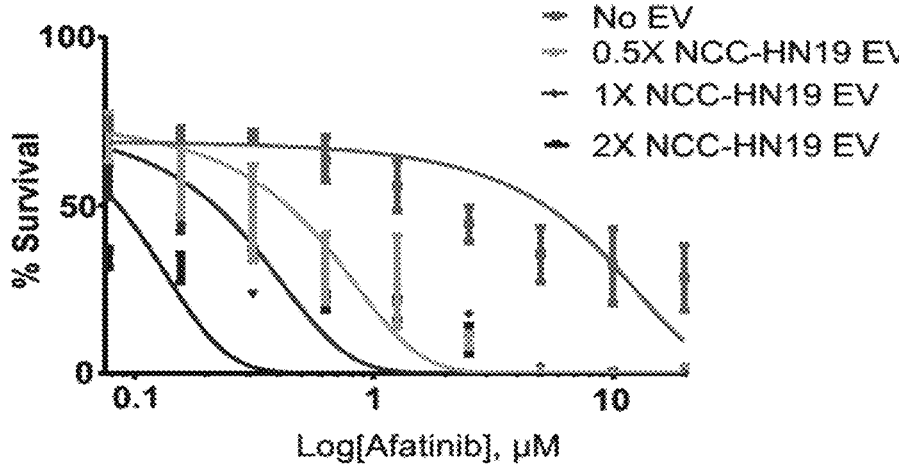
Figure 12A:
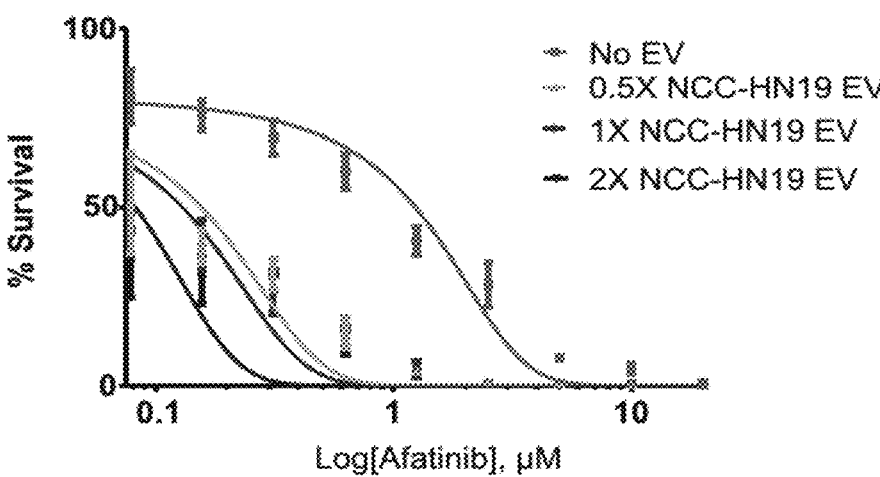
Figure 12A:
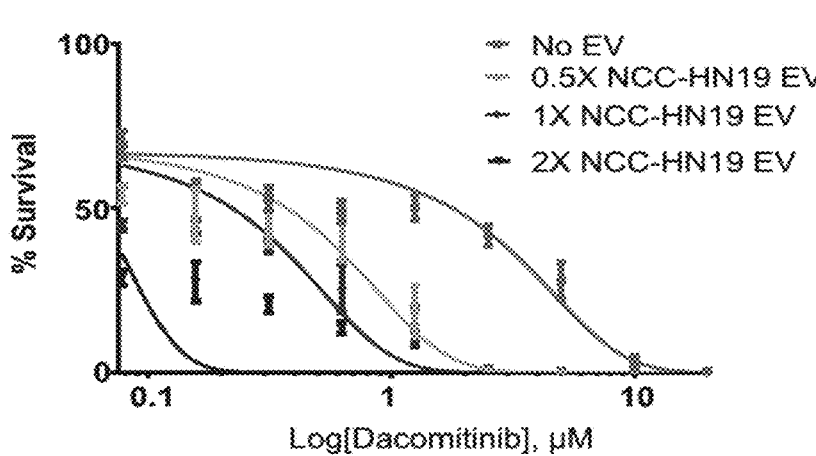
Figure 12A:
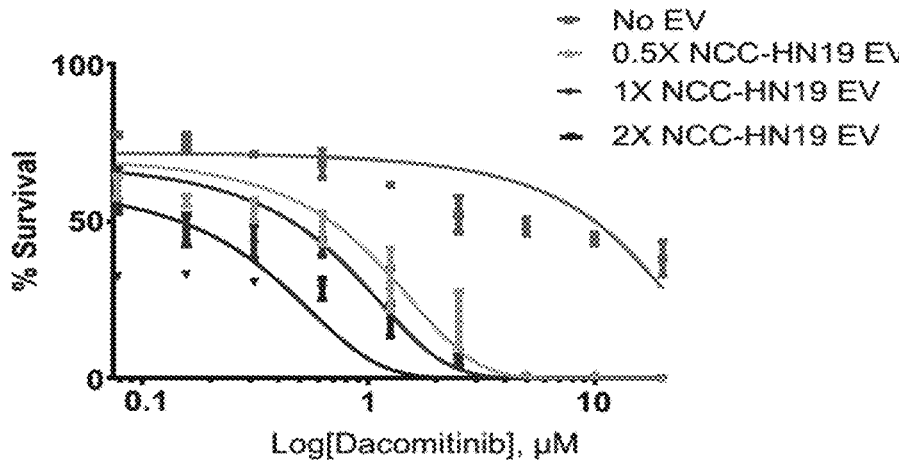
Figure 12A:
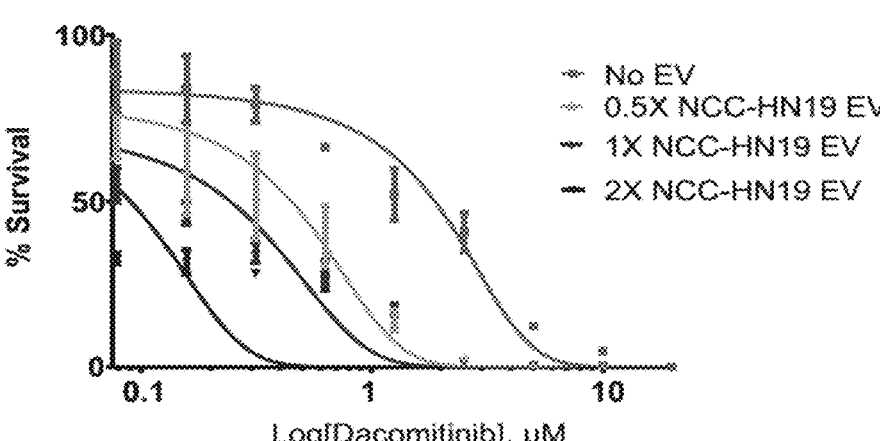
Figure 12B:
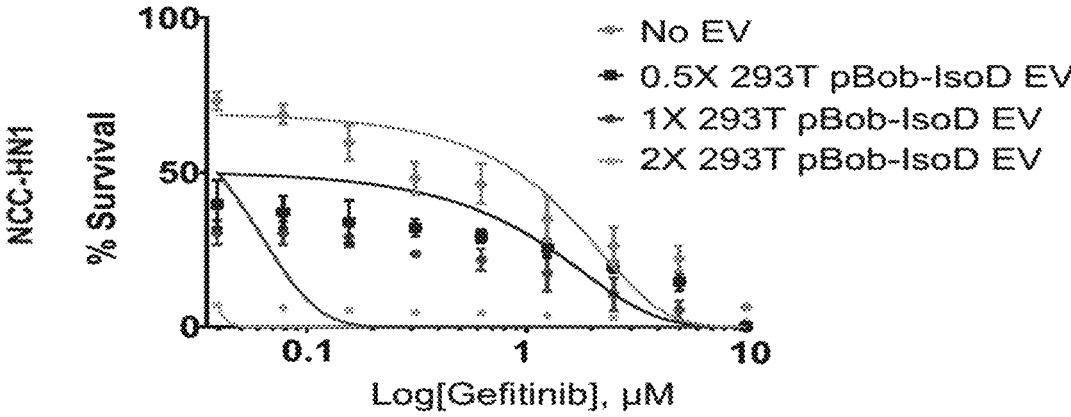
FIG. 12B shows the results of NCC-HN1, NCC-HN120M and NCC-HN182M cells co-treated with EV from 293T with over-expressed EGFR isoform D, and gefitinib, afatinib or dacomitinib. Graphs show percentage survival of NCC-HN1, NCC-HN120M and NCC-HN182M cells treated without exosomes (No EV) or with 0.5× (0.5×293T pBob-IsoD EV), 1× (1×293T pBob-IsoD EV) or 2× (2×293T pBob-IsoD EV) relative quantity of exosomes from Isoform D expressing 293T cells in combination with a first generation tyrosine kinase inhibitor (gefitinib) or second generation tyrosine kinase inhibitors (afatinib or dacomitinib).
Figure 12B:
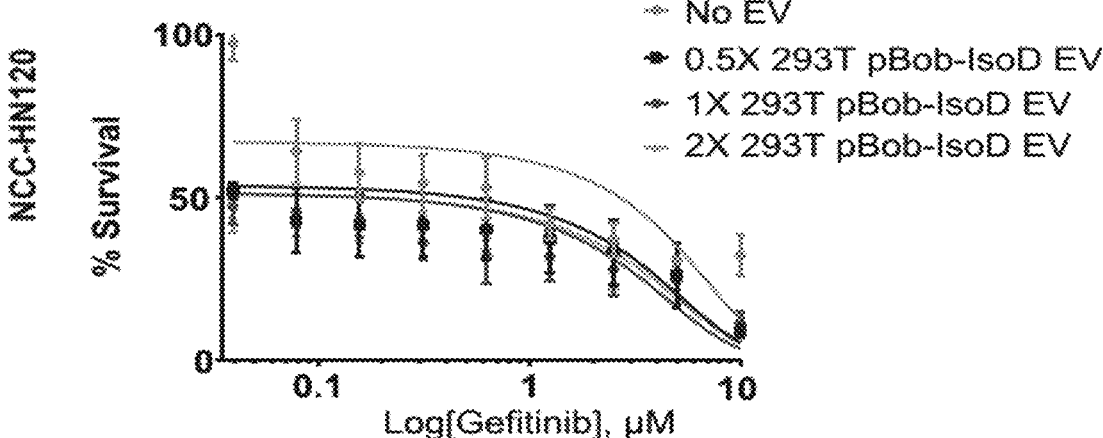
Figure 12B:
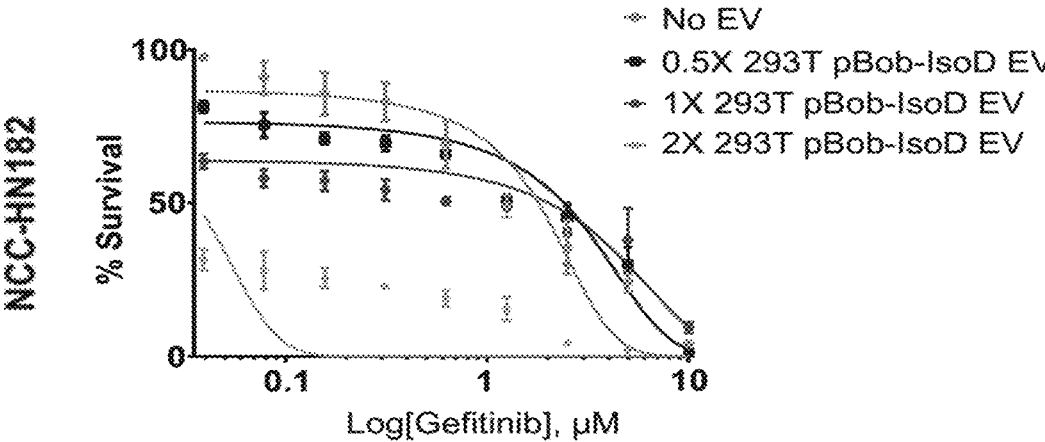
Figure 12B:
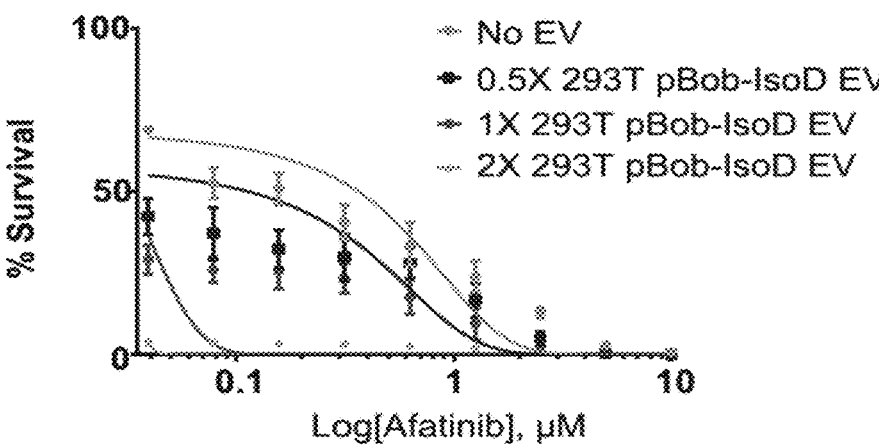
Figure 12B:
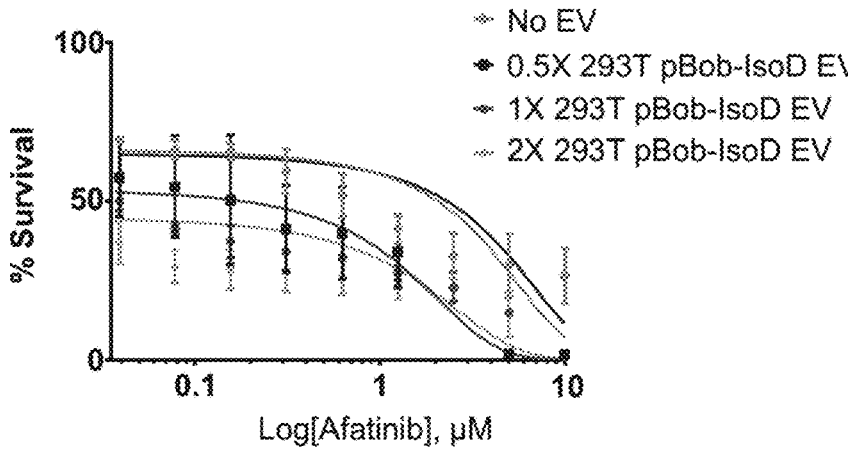
Figure 12B:
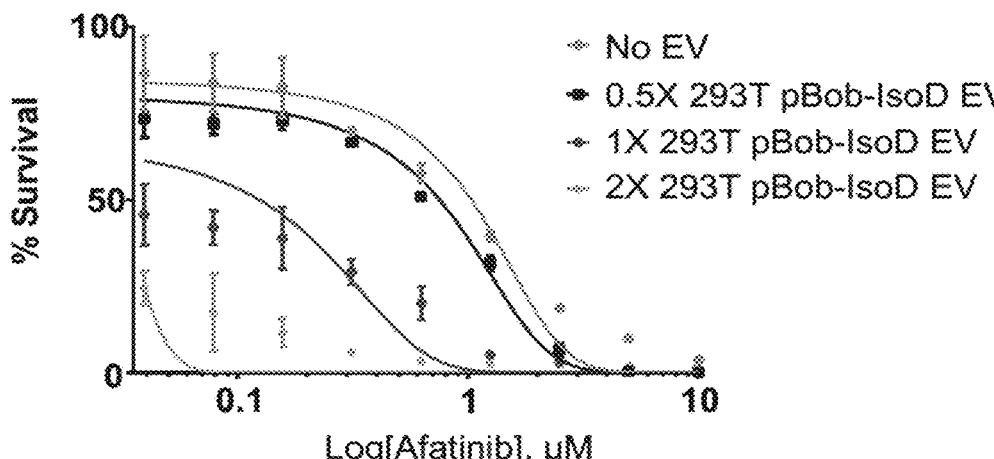
Figure 12B:
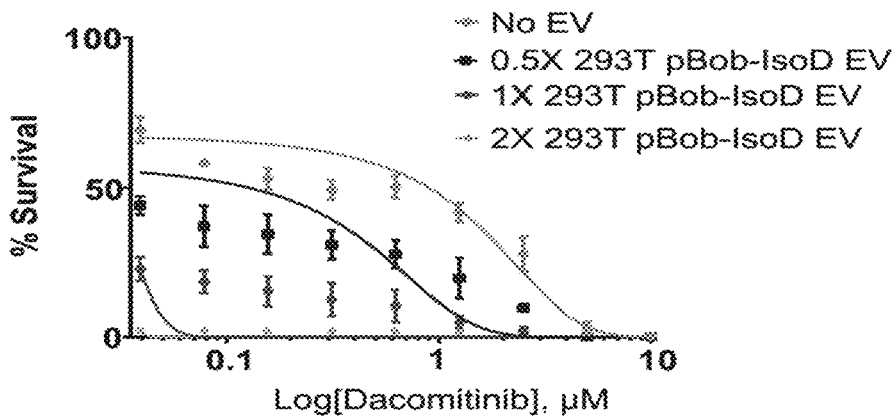
Figure 12B:
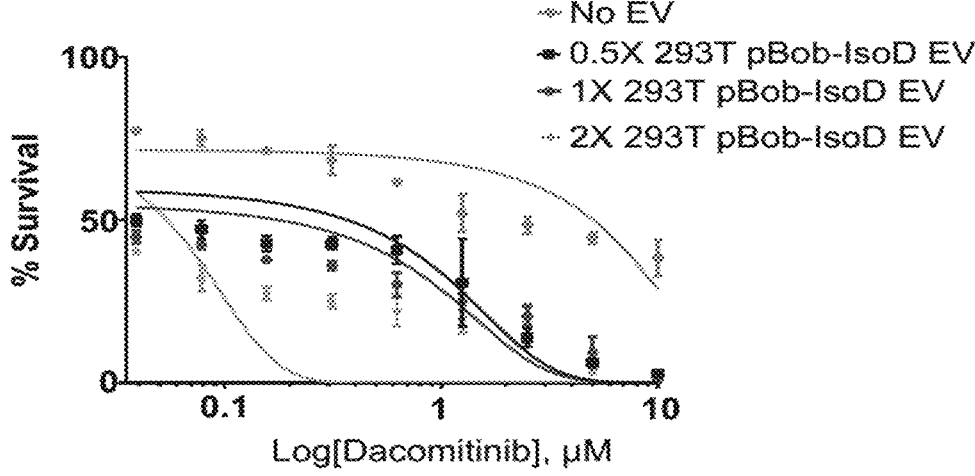
Figure 12B:
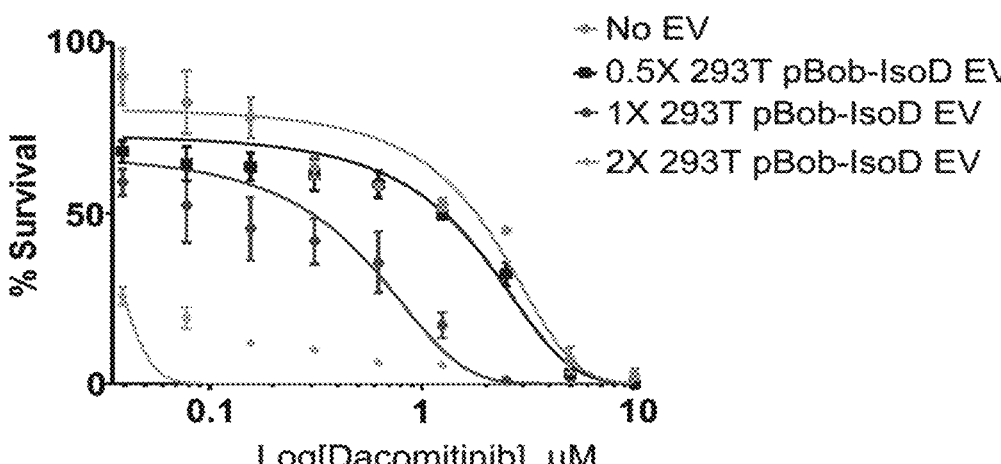
Figure 12C:
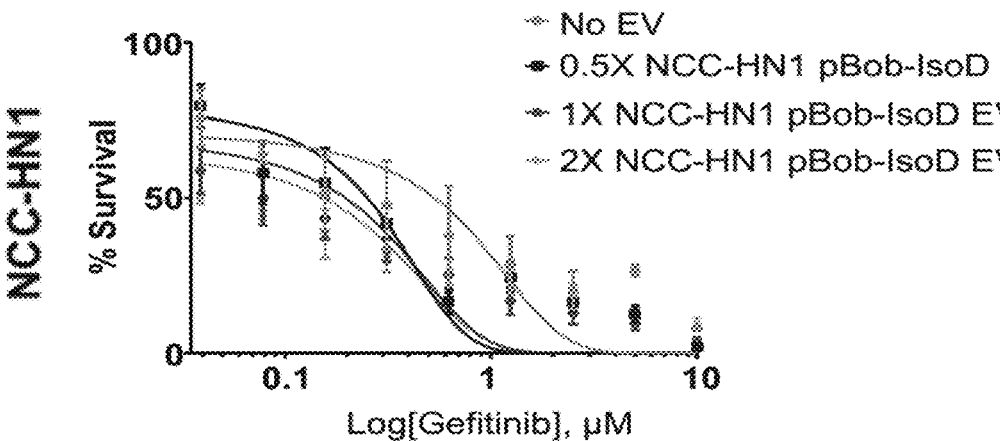
FIG. 12C shows the results of NCC-HN1, NCC-HN120M and NCC-HN182M cells co-treated with EV from NCC-HN1 with over-expressed isoform D, and gefitinib, afatinib or dacomitinib. Graphs show percentage survival of NCC-HN1, NCC-HN120M and NCC-HN182M cells treated without exosomes (No EV) or with 0.5× (0.5×NCC-HN1 pBob-IsoD EV), 1× (1×NCC-HN1 pBob-IsoD EV) or 2× (2×NCC-HN1 pBob-IsoD EV) relative quantity of exosomes from isoform D expressing NCC-HN1 cells in combination with a first generation tyrosine kinase inhibitor (gefitinib) or second generation tyrosine kinase inhibitors (afatinib or dacomitinib). This data shows that EV from either HNSCC cells with endogenously high EGFR isoform D expression (HN19), HNSCC cells with endogenously low, but engineered to over-express Isoform D (HN1 pBob-IsoD) or non-HNSCC cells with ectopically expressed EGFR isoform D (293T pBob-IsoD), can increase the sensitisation of cancer cells to tyrosine kinase inhibitors (TKIs) in a dose-dependent manner.
Figure 12C:
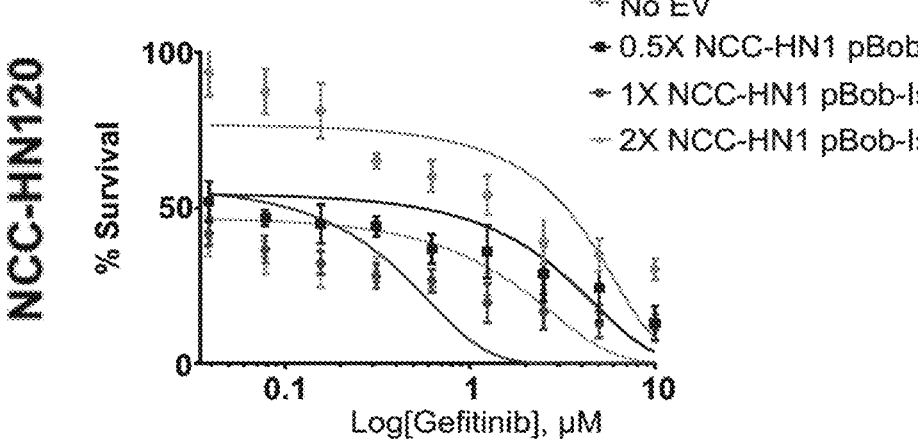
Figure 12C:
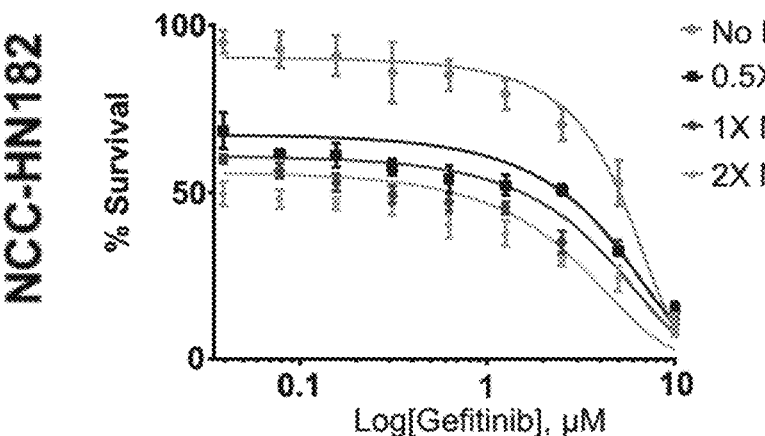
Figure 12C:
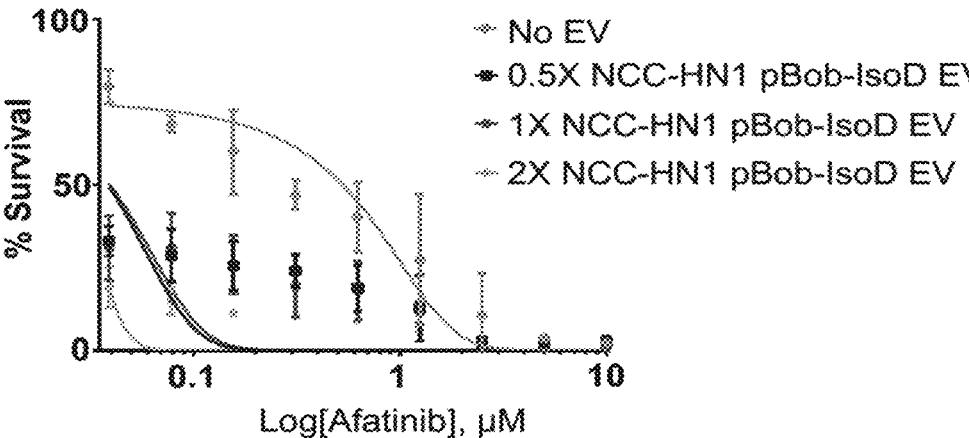
Figure 12C:
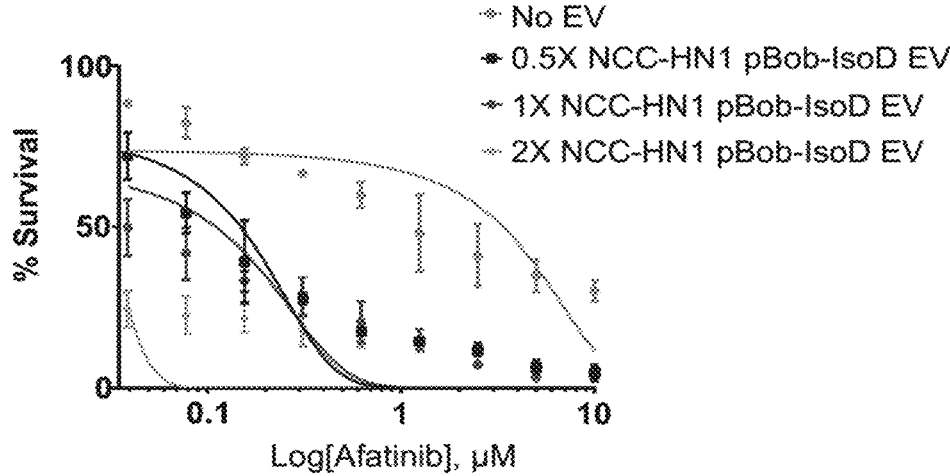
Figure 12C:
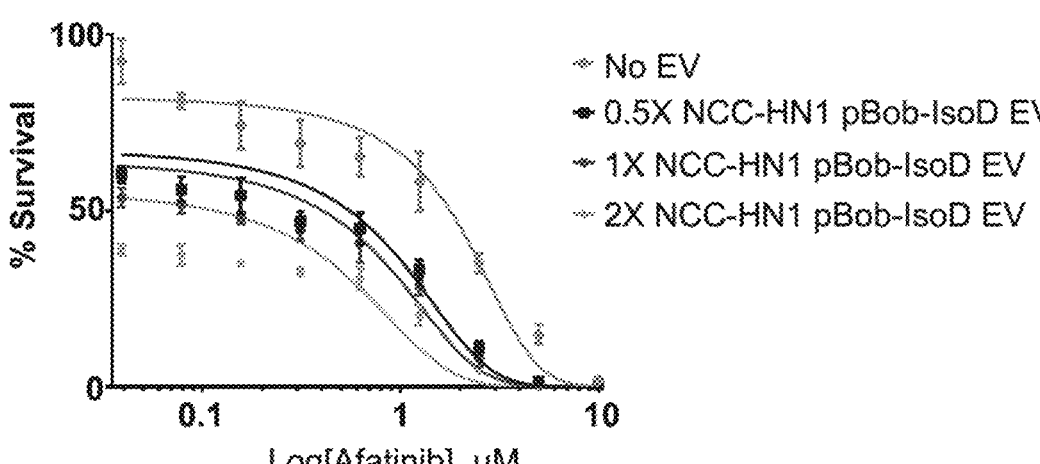
Figure 12C:
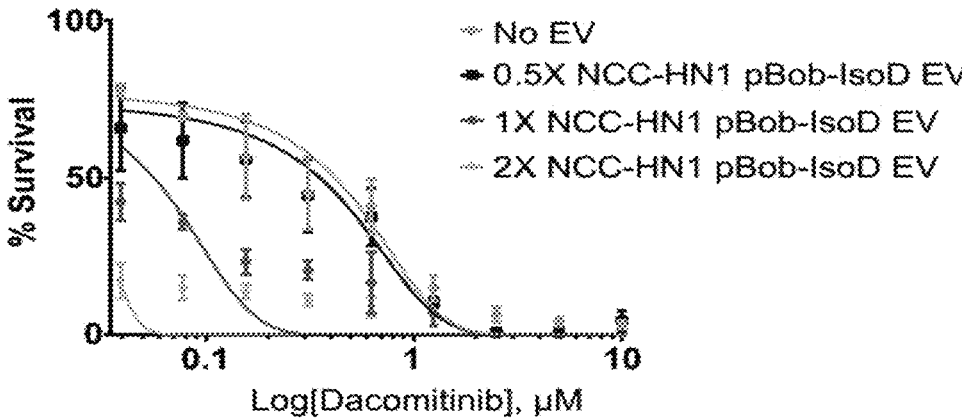
Figure 12C:
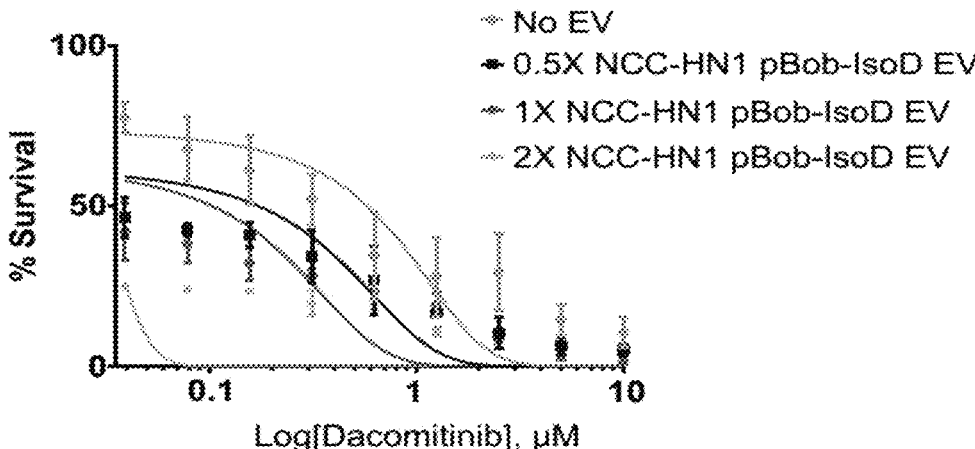
Figure 12C:
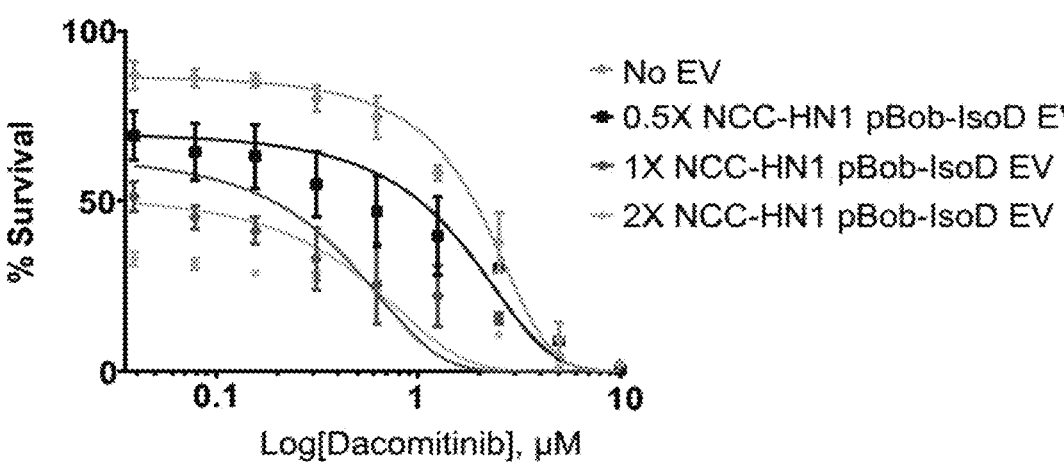

Data has shown that EGFR isoform D-dependent sensitisation of cells works across a range of different tyrosine kinase inhibitors (TKIs) that target the wild-type EGFR. To test the response of head and neck squamous cell carcinomas (HNSCC) cell lines to tyrosine kinase inhibitors (TKIs) in the presence of EGFR exosomal isoform D, three primary cell lines, namely NCC-HN1, NCC-HN120M and NCC-HN182M, were used. A panel of eight tyrosine kinase inhibitors (TKIs) that represented three generations of TKI used in the clinic, were selected, namely gefitinib and erlotinib (first generation); afatinib and dacomitinib (second generation); and lapatinib, nazartinib, WZ4002, and osimertinib (third generation). NCC-HN1, NCC-HN120M and NCC-HN182M cells were treated with eight tyrosine kinase inhibitors, each individually, in the presence of exosome (EV) derived from NCC-HN19 and NCC-HN137P cells. Results (as shown in FIG. 11) show that cells are sensitised most efficiently to first and second generation tyrosine kinase inhibitors, when co-treated with exosomes containing endogenously expressed EGFR isoform D (EV from NCC-HN19 and NCC-HN137P) (FIG. 11A-G). FIG. 11H shows HNSCC cells were also sensitized to first generation (gefitinib) and second generation (afatinib and dacomitinib) tyrosine kinase inhibitors when co-treated with exosomes containing overexpressed EGFR isoform D (EV from 293T).

Thus, in one example, tyrosine kinase inhibitor is an EGFR inhibitor. In another example, the tyrosine kinase inhibitor is a first-generation tyrosine kinase inhibitor. In yet another example, the tyrosine kinase inhibitor is a second-generation tyrosine kinase inhibitor. In further example, the tyrosine kinase inhibitor is a third-generation tyrosine kinase inhibitor.

Examples of tyrosine kinase inhibitors are, but are not limited to, gefitinib, erlotinib, erlotinib HCl, lapatinib, dacomitinib, TAE684, afatinib, dasatinib, saracatinib, veratinib, AEE788, WZ4002, icotinib, osimertinib, BI1482694, ASP8273, EGF816, AZD3759, nazartinib, and combinations thereof. Examples of first-generation tyrosine kinase inhibitors are, but are not limited to, gefitinib and erlotinib. Examples of second-generation tyrosine kinase inhibitors are, but are not limited to, afatinib and dacomitinib. Examples of third generation tyrosine kinase inhibitors are, but are not limited to, lapatinib, nazartinib, WZ4002, and osimertinib. In one example, the tyrosine kinase inhibitor is, but is not limited to, gefitinib, erlotinib and lapatinib, and combinations thereof. In another example, the tyrosine kinase inhibitor is, but is not limited to, gefitinib, afatinib and dacomitinib, and combinations thereof.

Further data shows the dose-response on degree of sensitisation compared to dose used (both arbitrary and expected quantification of EGFR isoform D). To see if increasing amount of exosomal isoform D modulate the sensitivity to tyrosine kinase inhibitor treatment, NCC-HN1, NCC-HN120M and NCC-HN182M cells were subjected to increasing doses of NCC-HN19 (endogenously expressed isoform D), 293T and NCC-HN1 (forced expression isoform D) derived EGFR isoform D containing exosomes (EV), with concurrent treatment of gefitinib, afatinib or dacomitinib. These experiments clearly show that there is a dose-dependent effect on cell sensitivity to tyrosine kinase inhibitor treatment, whereby increasing amounts of exosomal EGFR isoform D results in increasing sensitivity to EGFR tyrosine kinase inhibitors. This information is shown in FIG. 12.

Thus, in one example, there is disclosed a method of increasing sensitivity of an EGFR-related cancer to epidermal growth factor receptor (EGFR) tyrosine kinase inhibitor (TKI) comprising administering a therapeutically effective amount of epidermal growth factor receptor isoform D to a subject in need thereof. In another example, the method or the use further comprises administration of a tyrosine kinase inhibitor (TKI). Also disclosed herein is the use of epidermal growth factor receptor isoform D in the manufacture of a medicament for increasing sensitivity of an EGFR-related cancer to epidermal growth factor receptor (EGFR) tyrosine kinase inhibitor (TKI). Also disclosed is epidermal growth factor receptor isoform D for use in increasing sensitivity of an EGFR-related cancer to epidermal growth factor receptor (EGFR) tyrosine kinase inhibitor (TKI).

In another example, there is disclosed method of treating a subject suffering from an EGFR-related cancer, comprising administering to the subject an effective amount of epidermal growth factor receptor isoform D; and administering to the subject an effective amount of a tyrosine kinase inhibitor used to treat the EGFR-related cancer. Also, disclosed herein is the use of epidermal growth factor receptor isoform D in combination with a tyrosine kinase inhibitor in the manufacture of a medicament or for use in treating an EGFR-related cancer wherein the tyrosine kinase inhibitor is capable of treating the EGFR-related cancer. In combination means that the epidermal growth factor receptor isoform D and the tyrosine kinase inhibitor can be administered together or separately and/or can also be administered in separate or combined dosage form.

Figure 14B:
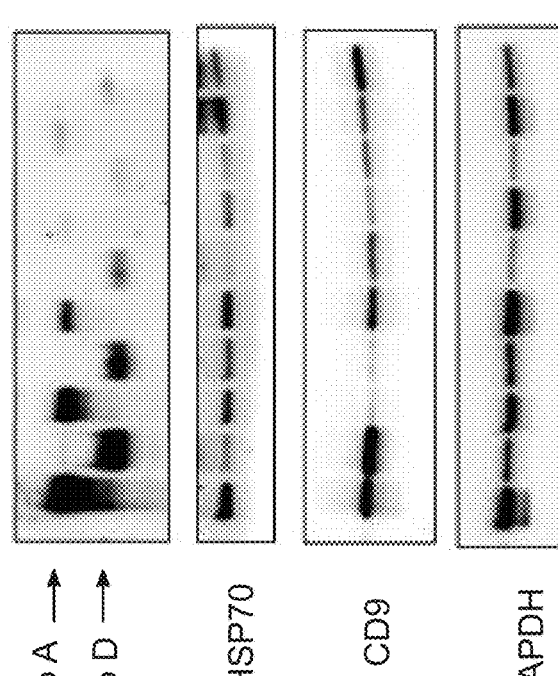
FIG. 14B shows a heatmap depicting the obtained $IC_{50}$ values of HNSCC cell line.
Figure 14A:
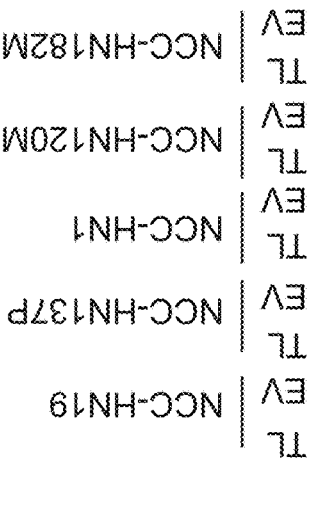
FIG. 14A shows the results of a Western blot analysis of total cell lysate (TL) and extracellular fraction (EV) from HNSCC cell lines.
Figure 14C:
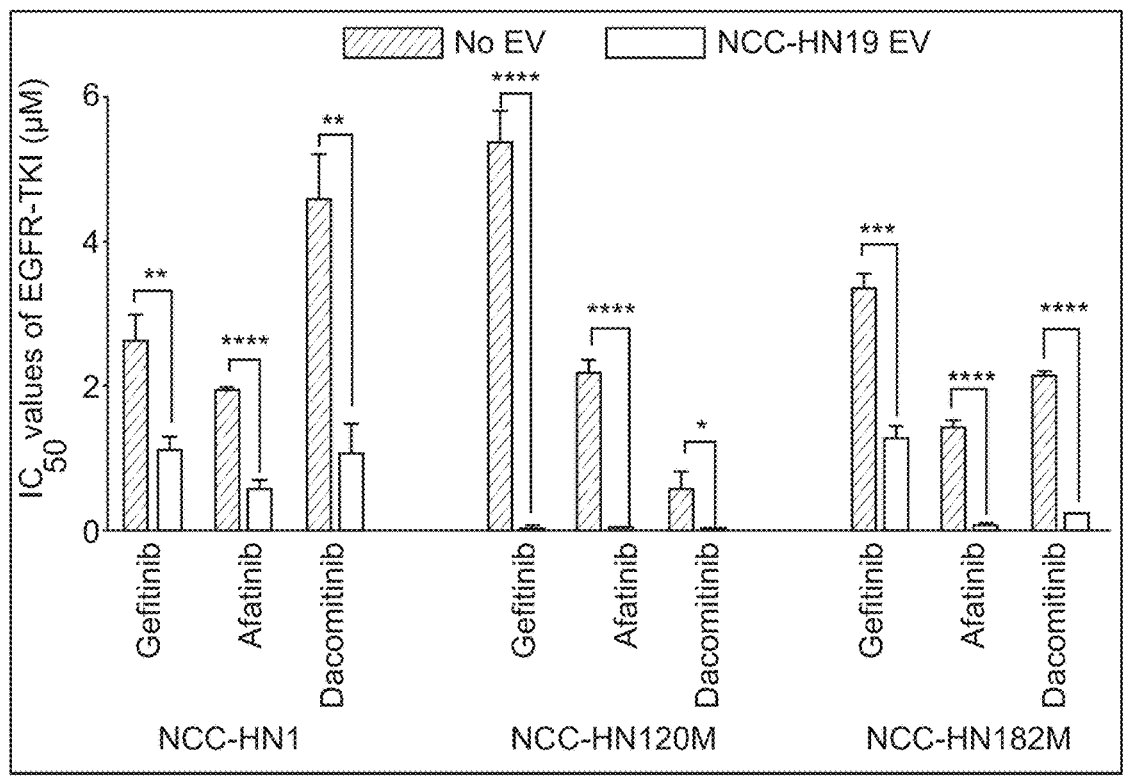
FIG. 14C shows the $IC_{50}$ values of the cell lines HNCC-HN1, NCC-HN120M and HCC-HN182M co-treated with NCC-HN19 EV (top panel), NCC-HN137P EV (bottom panel) or without EV (No EV). This data shows HNSCC cells, NCC-HN19 and NCC-HN137P, with higher relative levels of secreted EGFR isoform D, are more sensitive to EGFR-tyrosine kinase inhibitor (TKI) treatment. Additionally, co-application of exosomes/EVs derived from NCC-HN19 or NCC-HN137P with EGFR-tyrosine kinase inhibitors (TKIs) increases sensitization of cancer cell lines (HN1, HN120M and HN182M) that have intrinsically low EGFR isoform D expression.
Figure 14C:
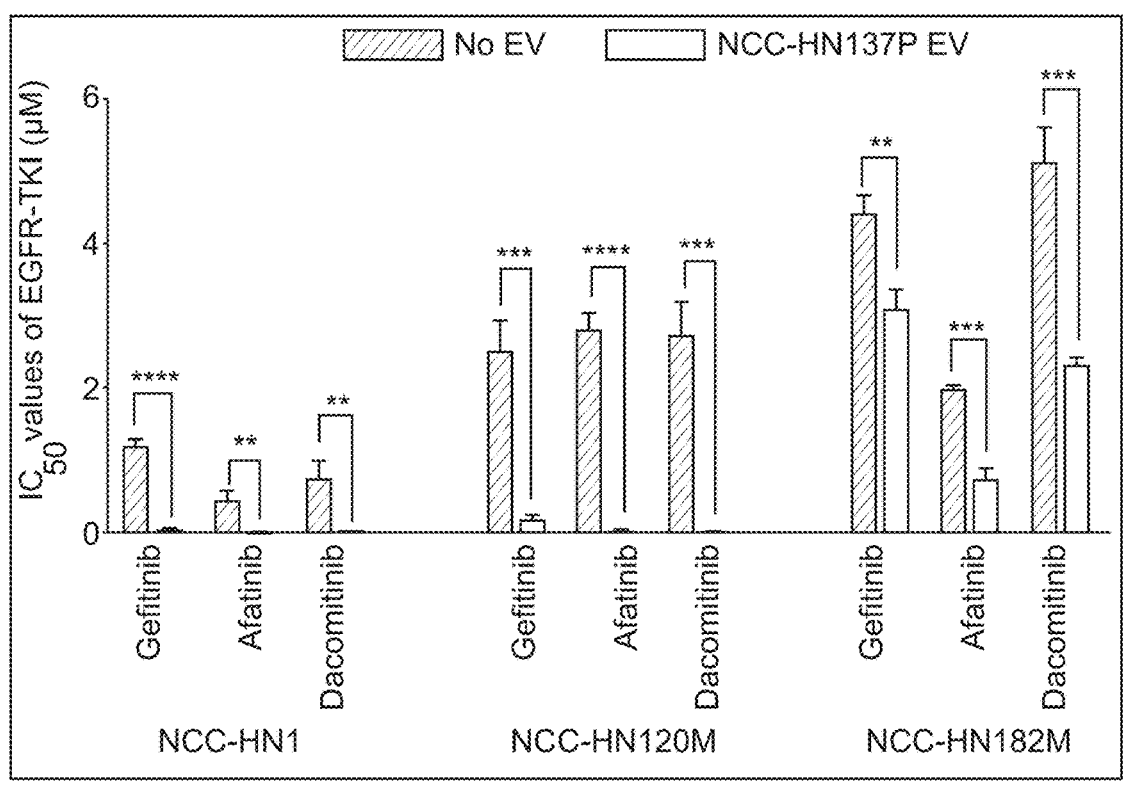

It is further shown that HNSCC cell lines with higher secreted EGFR isoform D (FIG. 14A) are more sensitive to tyrosine kinase inhibitors (TKIs; FIG. 14B). Application of extracellular vesicles from intrinsically (tyrosine kinase inhibitor-) sensitive cells (such as for example, and not limited to, HN19 and HN137P) to tyrosine kinase inhibitor-resistant cells (such as for example, and not limited to, HN1, HN120M, and HN182M) sensitises these resistant cells to gefitinib, afatinib, and dacomitinib (FIG. 14C). Co-treatment of the resistant cells with any one of the eight EGFR tyrosine kinase inhibitors disclosed herein showed a similar effect (FIG. 11G).

Figure 15:
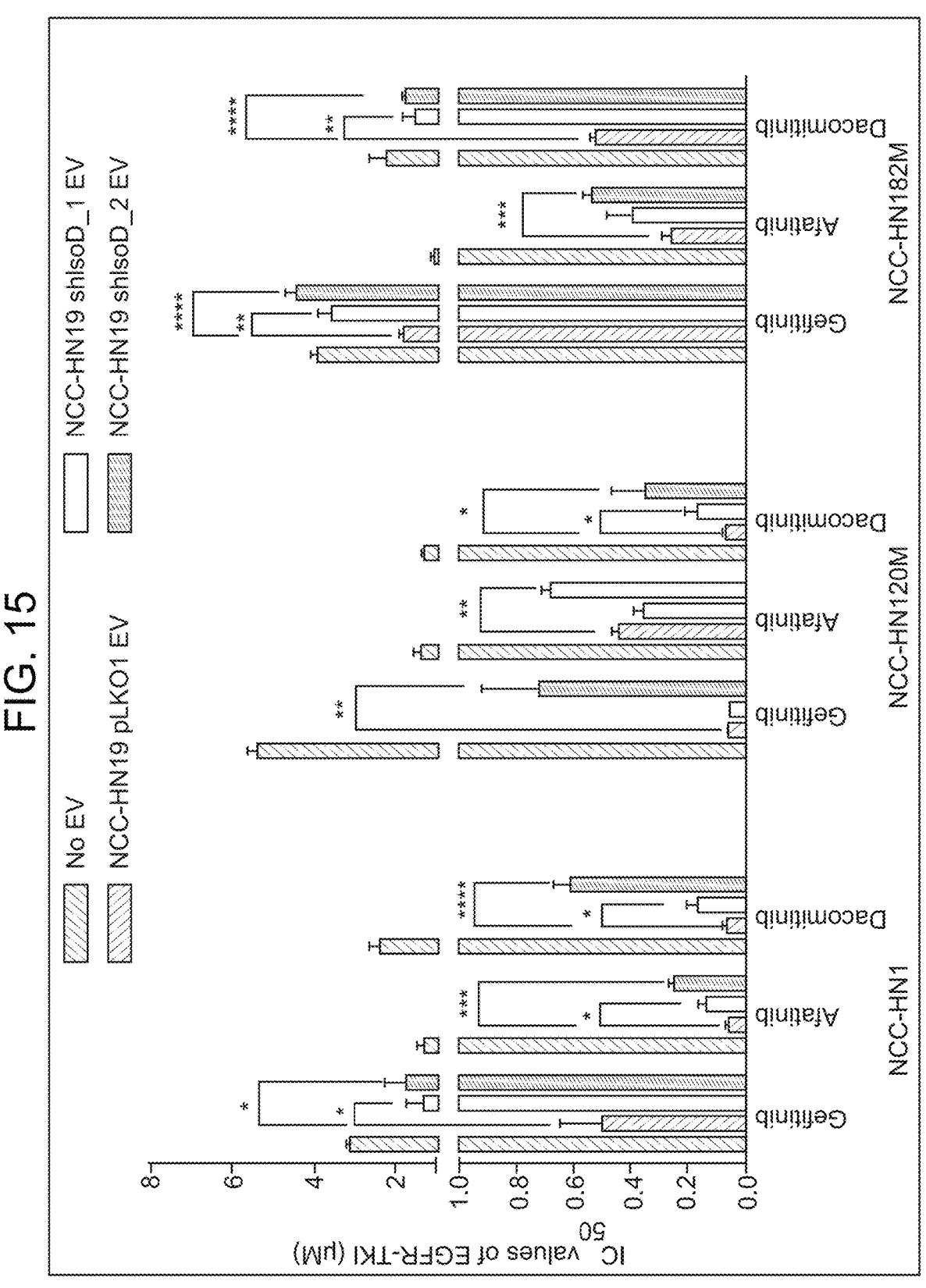
FIG. 15 shows $IC_{50}$ values of NCC-HN1, NCC-HN120M and NCC-HN182M treated with gefitinib, afatinib, or dacomitinib in the absence (No EV) or presence of NCC-HN19 EV (top panel) or NCC-HN137P (bottom panel) stably transfected with shRNA control (pLKO1 EV), shRNA strand #1 (shIsoD_1) or shRNA strand #2 (shIsoD_2) against EGFR Isoform D. Asterisks denote significance by student t-test: *p<0.05, p<0.01, *p<0.001, ****p<0.0001. This data demonstrates that EGFR isoform D on the exosome/EVs is necessary for the increased sensitising effect in EGFR tyrosine kinase inhibitor (TKI) co-treatment as the treatment of HNSCC cell lines with EVs containing knocked down EGFR isoform D has reduced sensitising effect.
Figure 15:
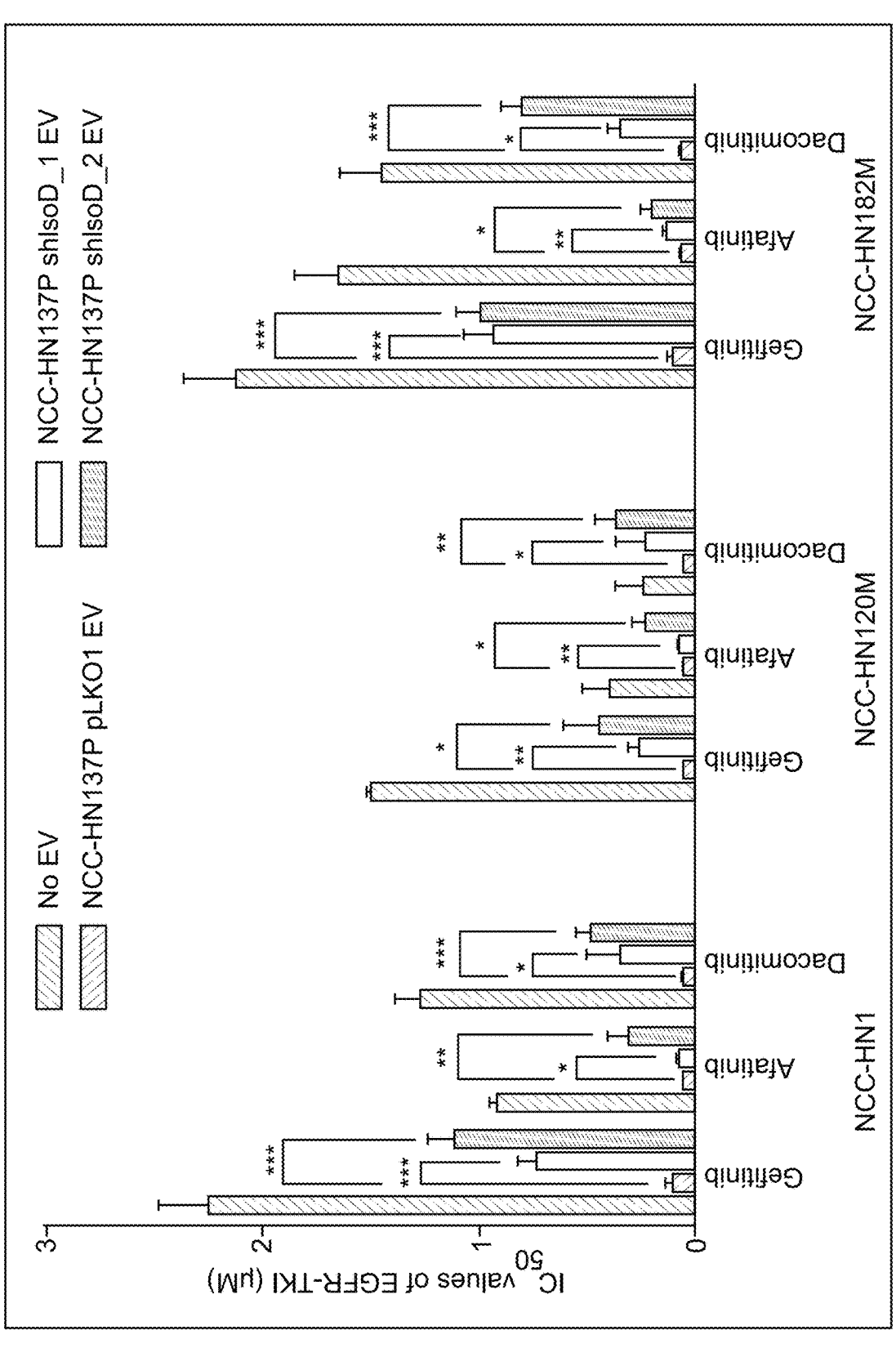
Figure 16A:
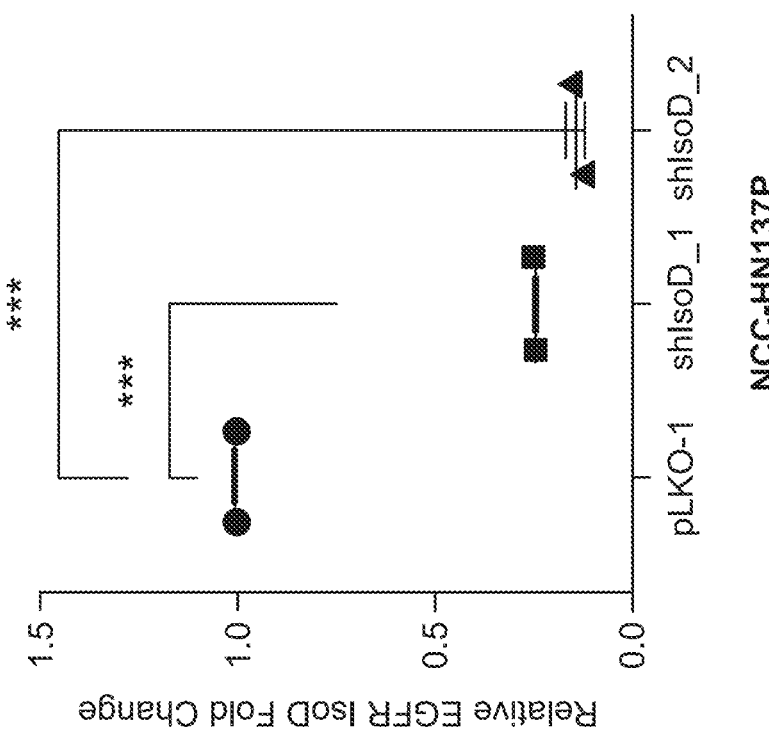
FIG. 16 shows the results of (A) relative mRNA levels and (B) Western blot analysis of NCC-HN1 and NCC-HN137P cells stably transfected with shRNA control (pLKO-1), shRNA strand #1 (shIsoD_1) or shRNA strand #2 (shIsoD_2) against EGFR Isoform D. TL: total cell lysate; EV: isolated extracellular vesicular fraction. For western blot, each lane is loaded with equal amount of protein. CD9 is used as an exosomal marker. Images show representative blots from three separate cell culture experiments. This data shows the decreased levels of isoform D relative to mRNA and protein for experiments in FIG. 15.
Figure 16A:
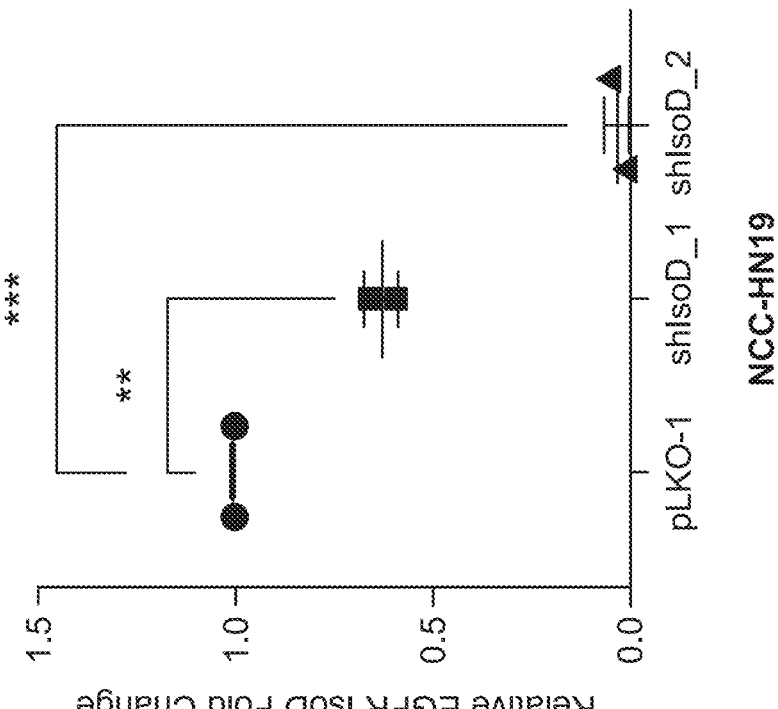
Figure 16B:
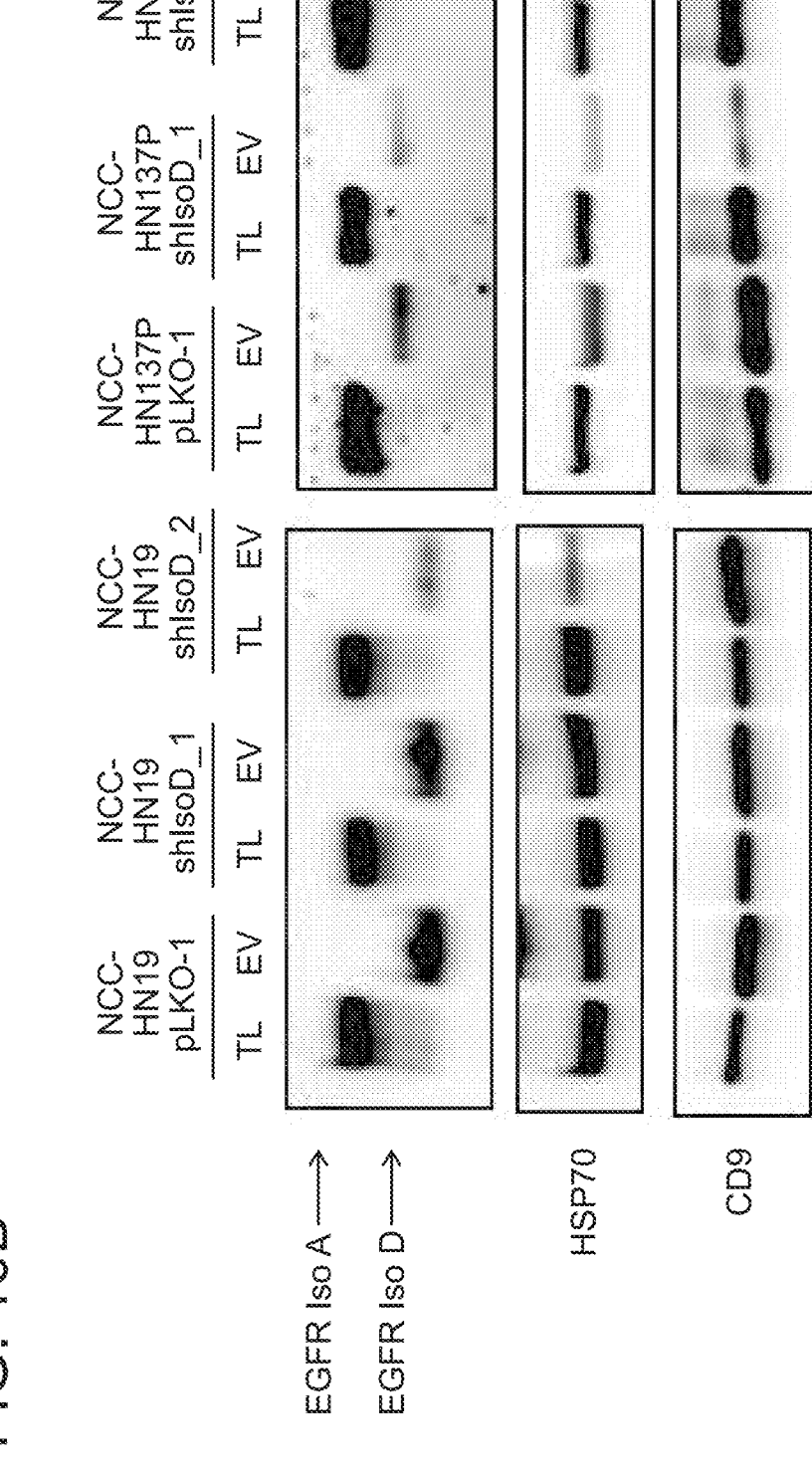

A knockdown study was performed by knocking down isoform D in an additional cell line (HN137P) using two shRNA strands (FIG. 15). FIG. 16 shows the results of the knock down by showing the relative mRNA (FIG. 16A) and protein (FIG. 16B) quantification. As shown in both HN19 and HN137P cell lines, the knockdown of isoform D decreases the ability of extracellular vesicles containing EGFR isoform D to confer increased sensitivity upon co-treatment with gefitinib, afatinib, and dacomitinib.

Figure 17A:
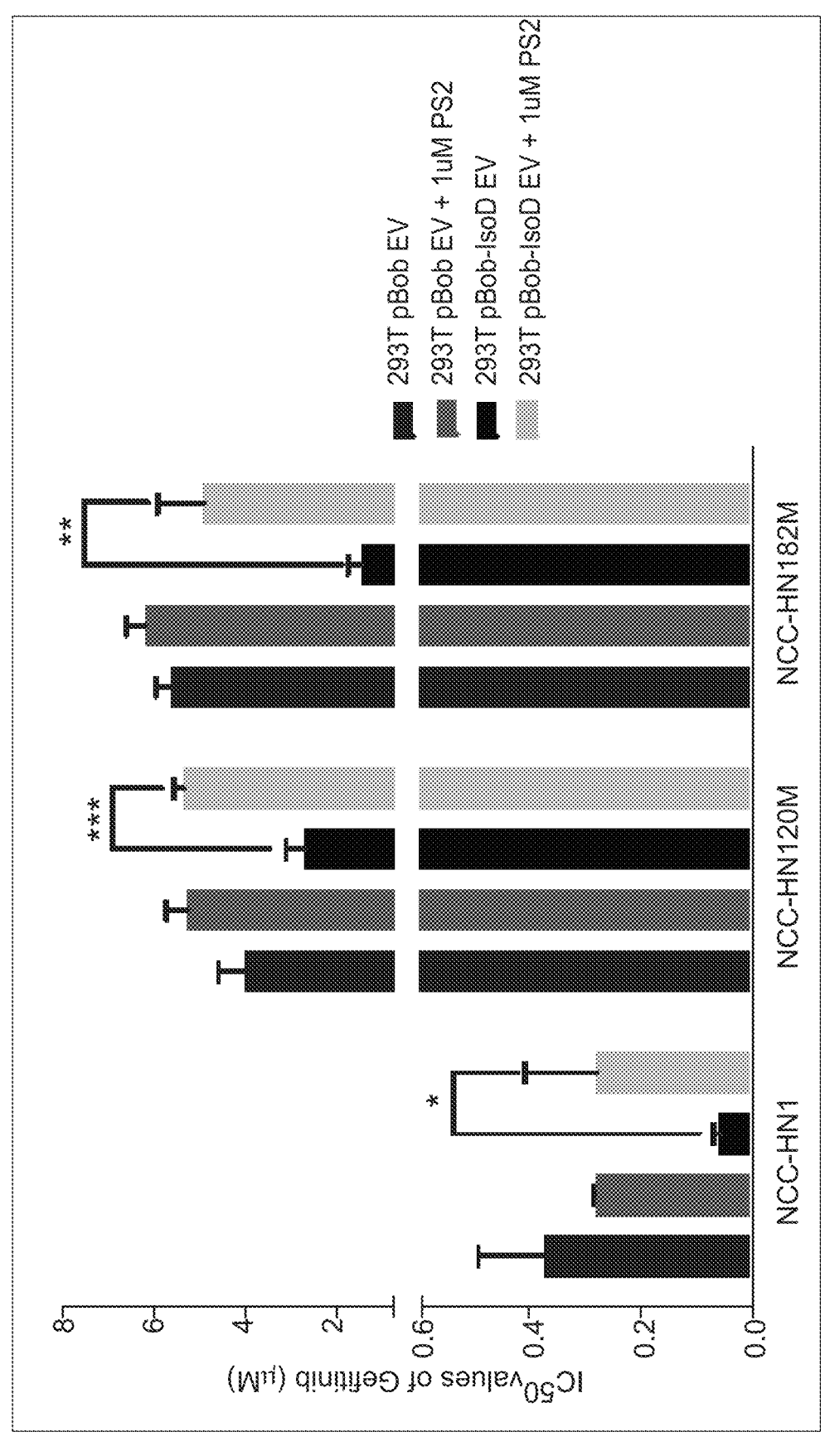
FIG. 17 shows $IC_{50}$ values obtained from NCC-HN1, NCC-HN120M and NCC-HN182M treated with (A) gefitinib, (B) afatinib, or (C) dacomitinib in the absence or presence of 1 μM Pitstop 2 (PS2), co-treated with EV from HEK293T over-expressing either vector control (pBob) or EGFR isoform D (pBob-IsoD). Asterisks denote significance by student t-test: *p<0.05, p<0.01, *p<0.001, ****p<0.0001. This data shows that the inhibition of clathrin-mediated endocytosis in HNSCC cells, reduces the sensitising effect of isoform D containing EV when co-treated with first or second generation EGFR tyrosine kinase inhibitors (TKIs).
Figure 17B:
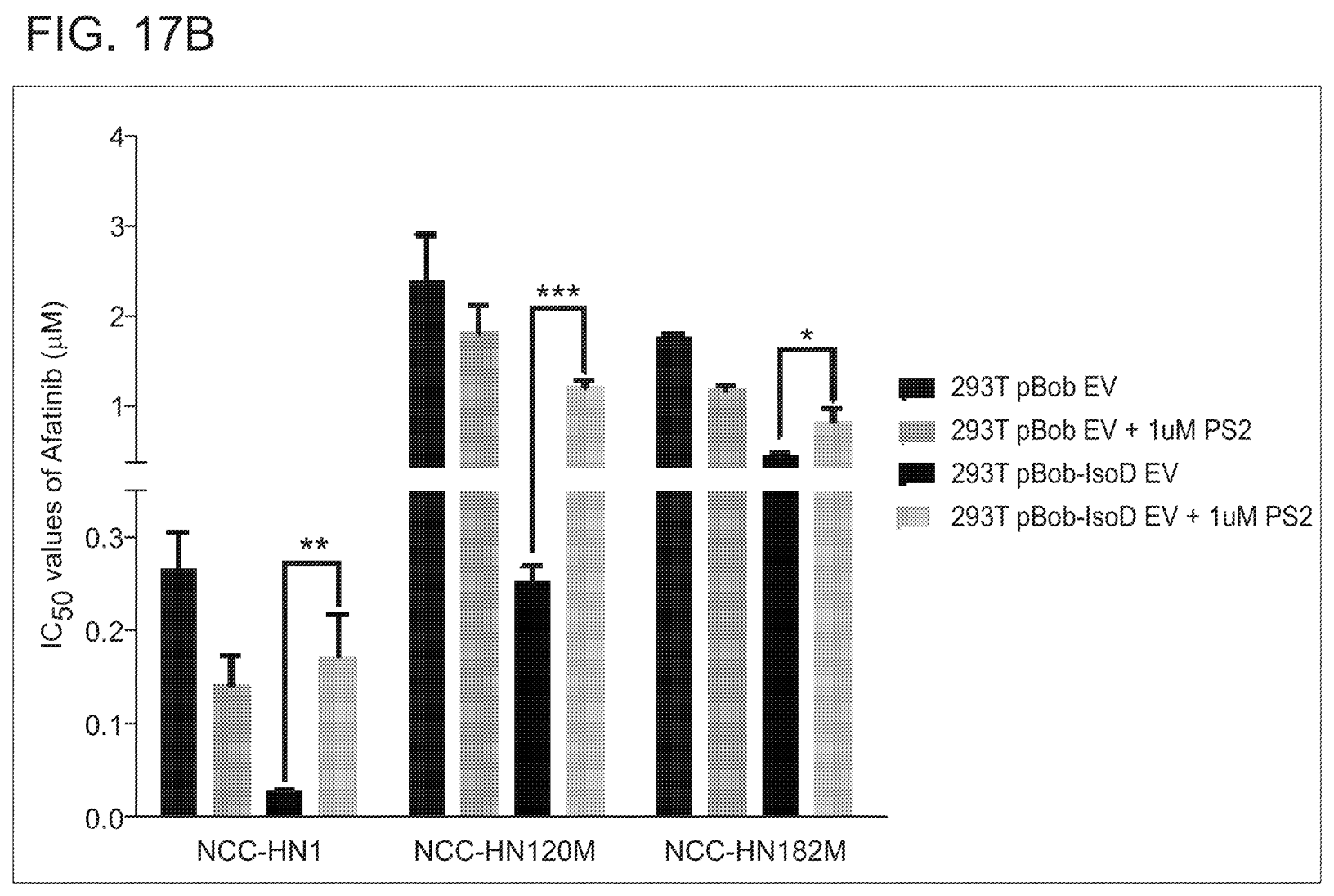
Figure 17C:
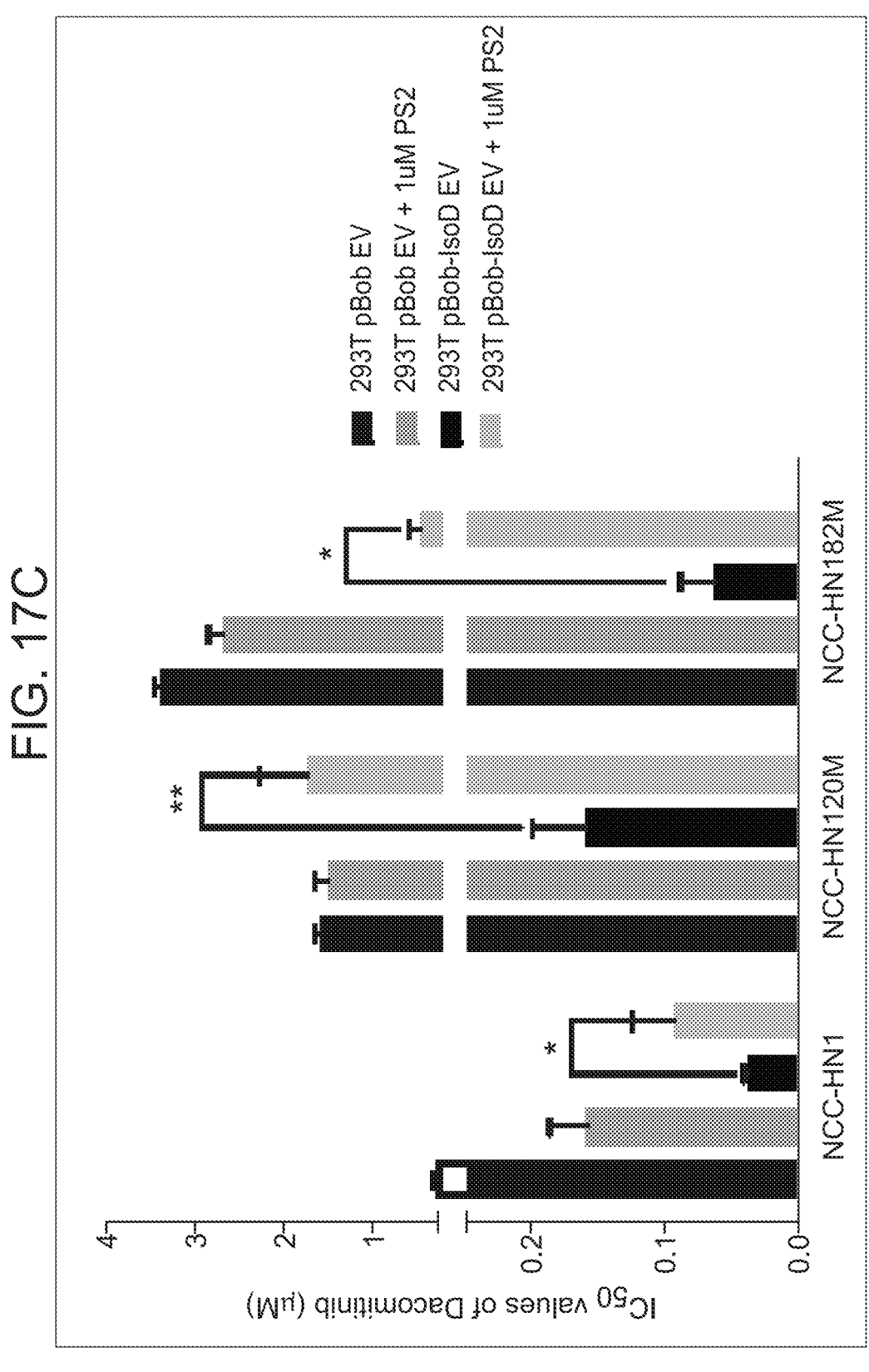
Figure 18:
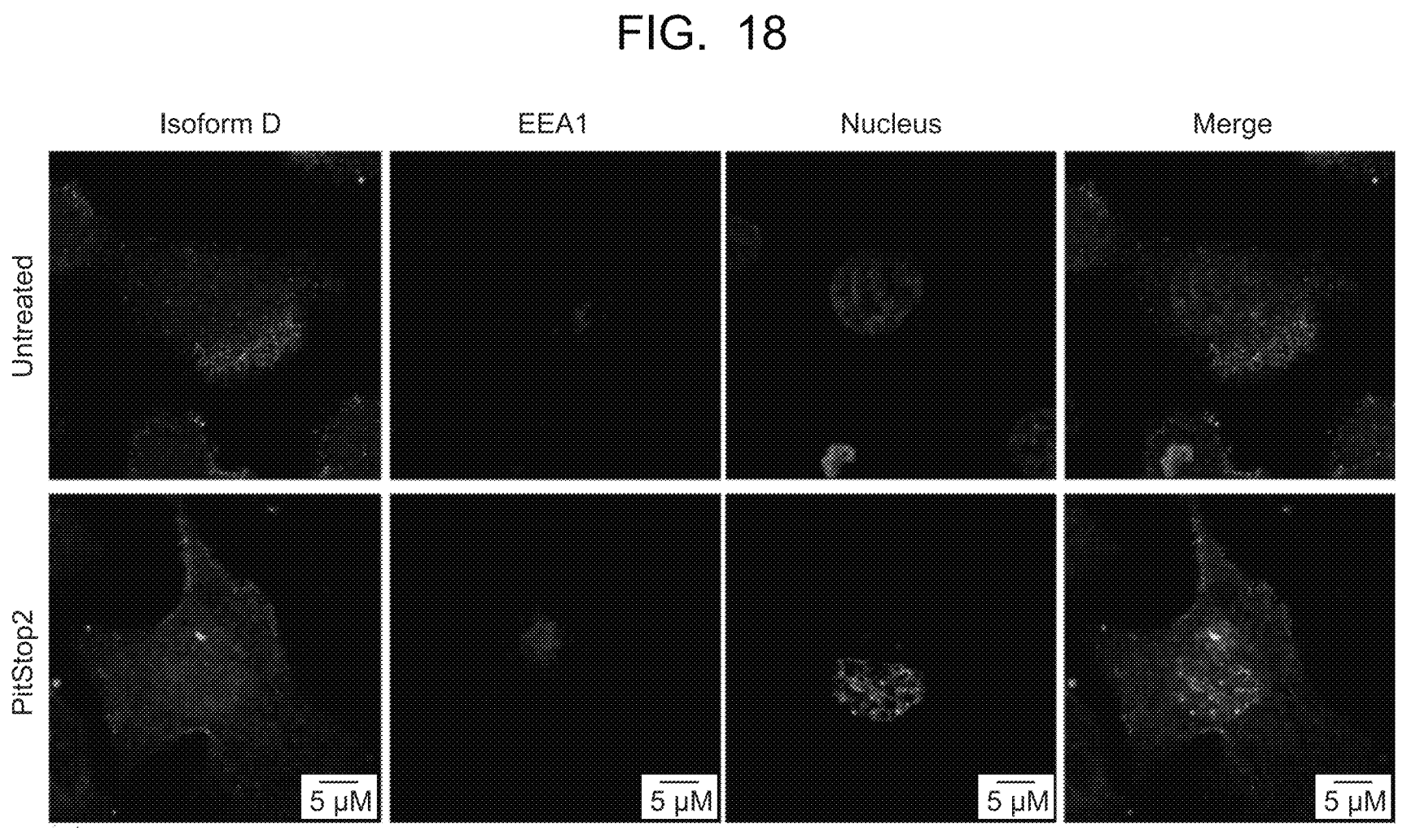

To show that the inhibition of clathrin-mediated endocytosis reduces the sensitizing effect of Isoform D containing extracellular vesicles when co-treated with TKIs, an experiment using a clathrin-mediated endocytosis inhibitor (PitStop2) was performed. In this experiment, two further cell lines, HN120M and HN182M cells (in addition to HN1) were included and co-treated with gefitinib (FIG. 17A), afatinib (FIG. 17B), and dacomitinib (FIG. 17C). In all three HNSCC cell lines, PitStop2 was shown to consistently reduces the sensitizing effect of EGFR isoform D extracellular vesicles. Without being bound by theory, it is thought that PitStop2 prevented the endocytosis of EGFR isoform D containing extracellular vesicles, thereby preventing EGFR isoform D from entering the target cells. This in turn is thought to decrease (or, at least, not increase) the target cell's sensitivity to tyrosine kinase inhibitors. Results of an immunofluorescence assay revealed that cells treated with Pit-Stop2 showed EGFR isoform D localised on the cell membrane, instead of in the internal cell compartments (FIG. 18).

To further determine the role and requirement of the endocytosis processes in target cells, which facilitates the sensitizing effect of EGFR isoform D, a series of proteins essential for transporting endocytic cargo from the cell membrane into the luminal compartments within the cells were systematically knocked down. One such protein, for example, is the protein Rab5A, which is important for the transport of cargo from the cell surface to early endosomal compartment. Another protein, Rab7A, is plays a role in transporting cargo from the early endosomal to the late endosomal compartment. EEA1 is a scaffold protein residing in the early endosomal compartment.

Figure 19A:
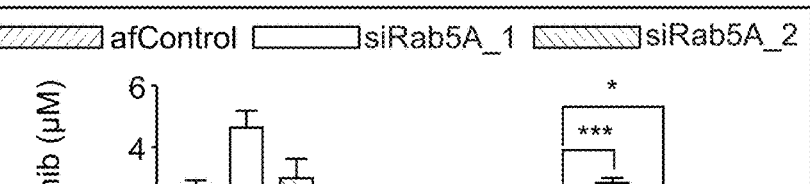
FIG. 19A shows the $IC_{50}$ values of NCC-HN1, NCC-HN120M and NCC-HN182M transfected with siRNA control (siCtrl), siRab5A strand #1 (siRab5A_1) or siRab5A strand #2 (siRab5A_2) and co-treated with gefitinib, afatinib, or dacomitinib, in the absence (No EV) or presence of EV from HEK293T over-expressing vector (pBob) or isoform D (pBob-Isoform D).
Figure 19A:
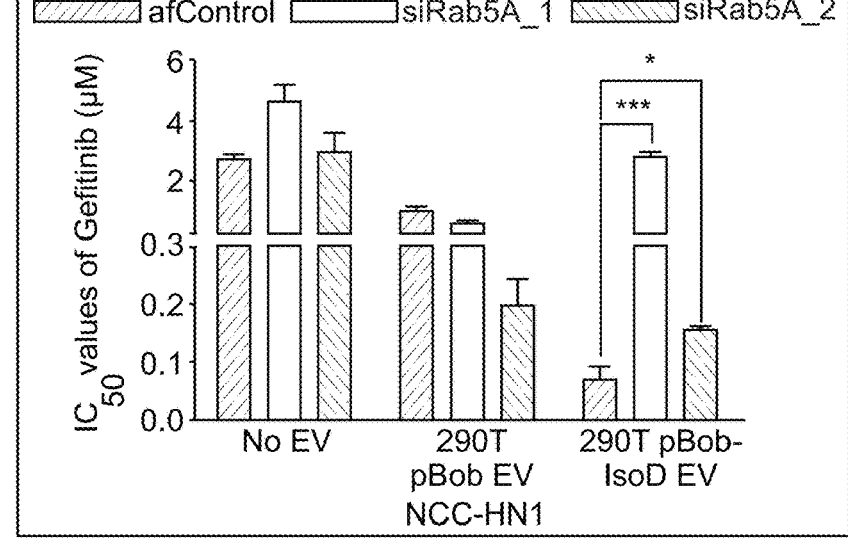
Figure 19A:
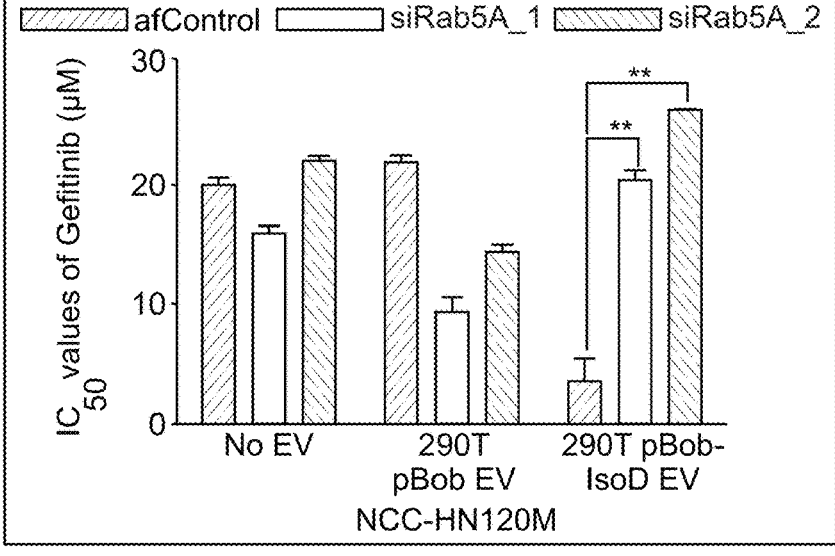
Figure 19A:
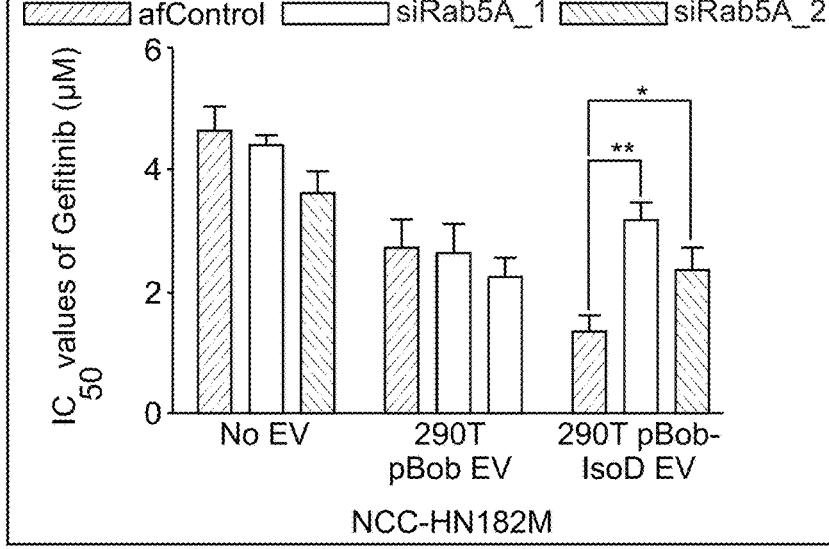
Figure 19A:
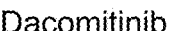
Figure 19A:
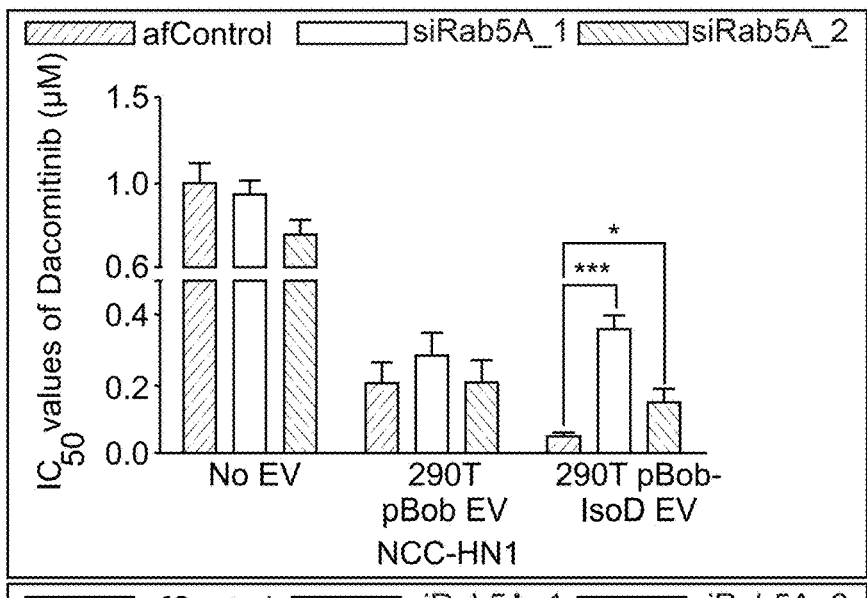
Figure 19A:
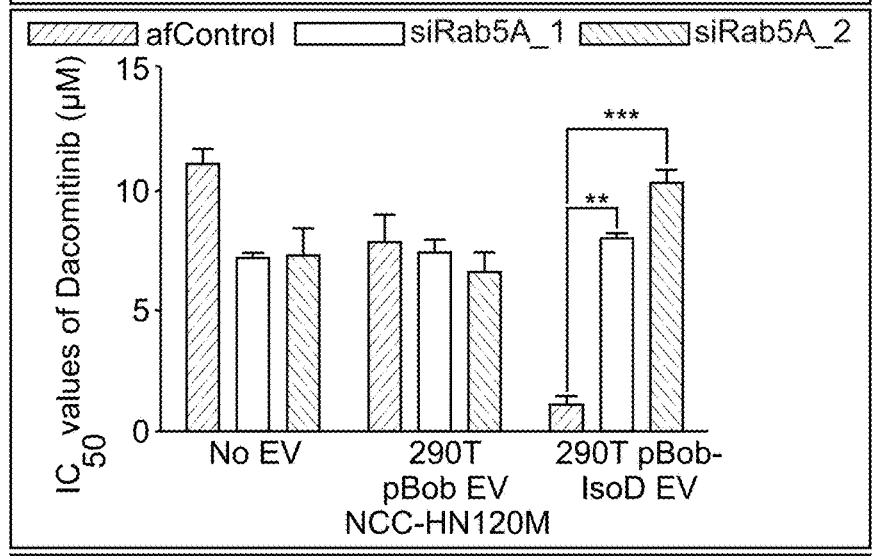
Figure 19A:
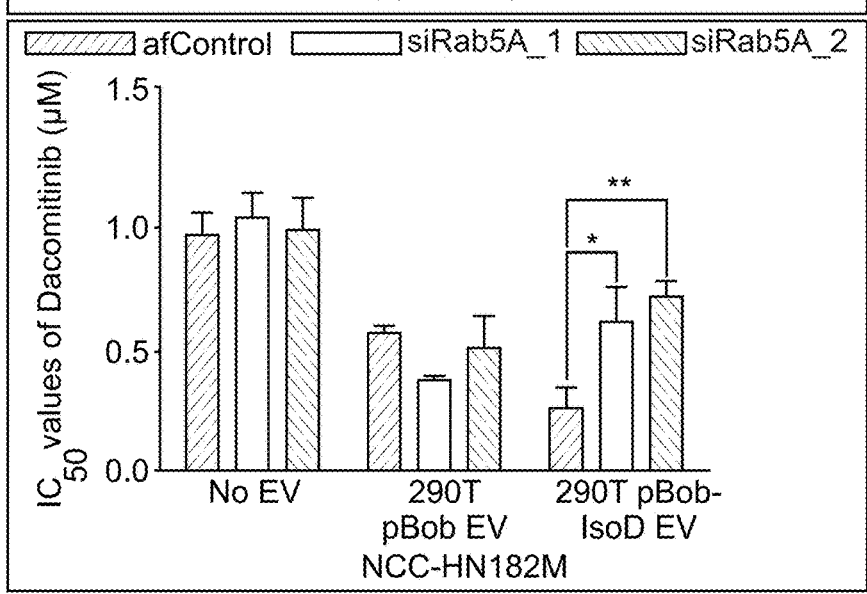
Figure 19B:
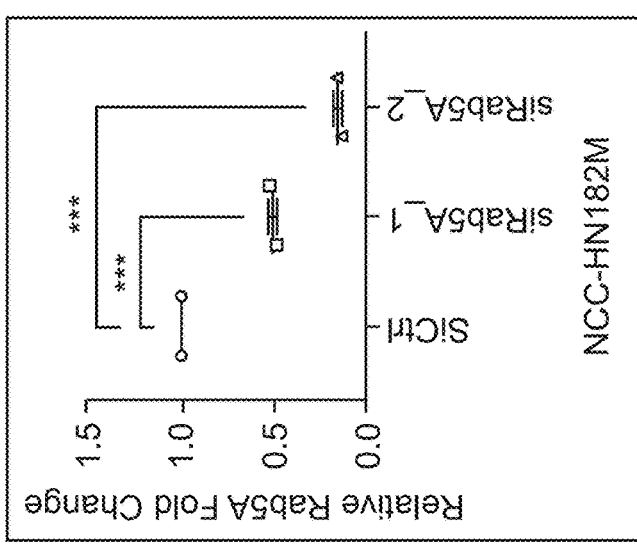
FIG. 19B shows the relative mRNA levels of Rab5A after transfection. Asterisks denote significance by student t-test: *p<0.05, p<0.01, *p<0.001, ****p<0.0001.
Figure 19B:
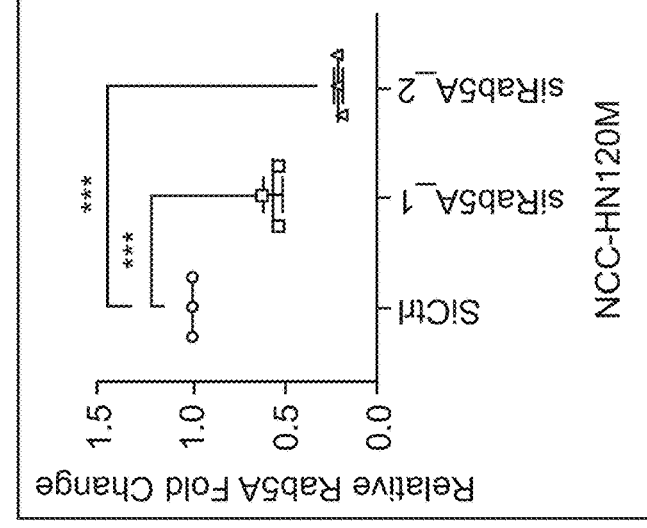
Figure 19B:
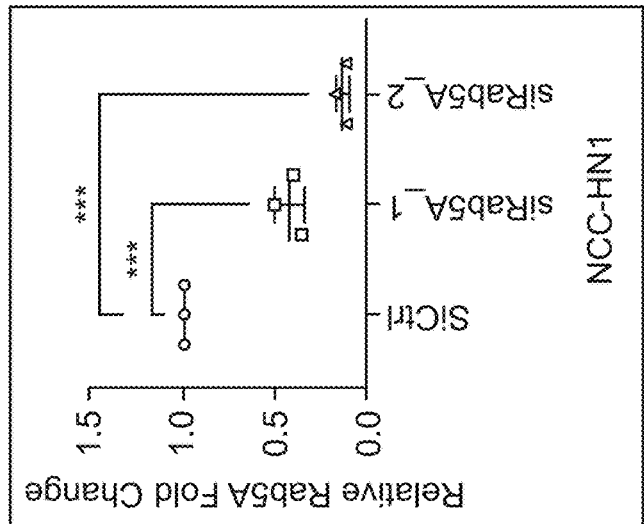

Firstly, Rab5A was knocked down in HN1, HN120M, and HN182M cells. These cells were subsequently co-treated with EGFR isoform D extracellular vesicles obtained from overexpressing HEK293T cells. A decrease in sensitization conferred by EGFR isoform D expressing extracellular vesicles was observed compared to a control (FIG. 19A). FIG. 19B shows the relative mRNA of siRab5A knockdown.

Figure 20A:
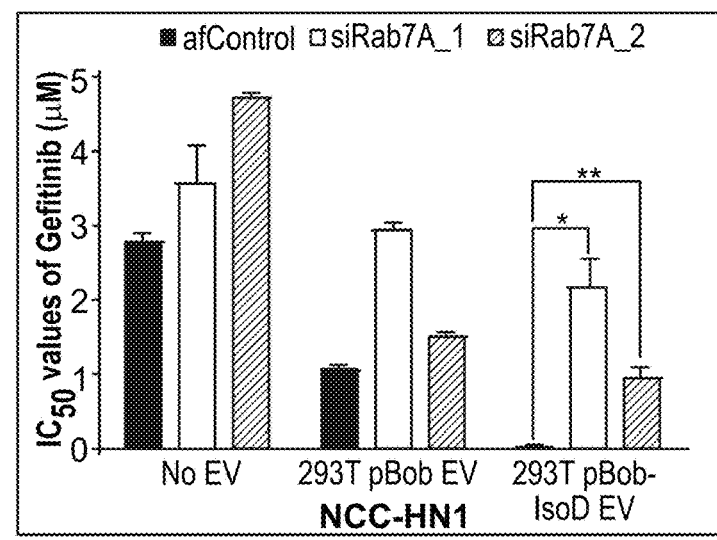
FIG. 20A shows the $IC_{50}$ values of NCC-HN1, NCC-HN120M and NCC-HN182M transfected with siRNA control (siCtrl), siRab7A strand #1 (siRab7A_1) or siRab7A strand #2 (siRab7A_2) and co-treated with gefitinib, afatinib, or dacomitinib, in the absence (No EV) or presence of EV from HEK293T over-expressing vector (pBob) or isoform D (pBob-Isoform D).
Figure 20A:
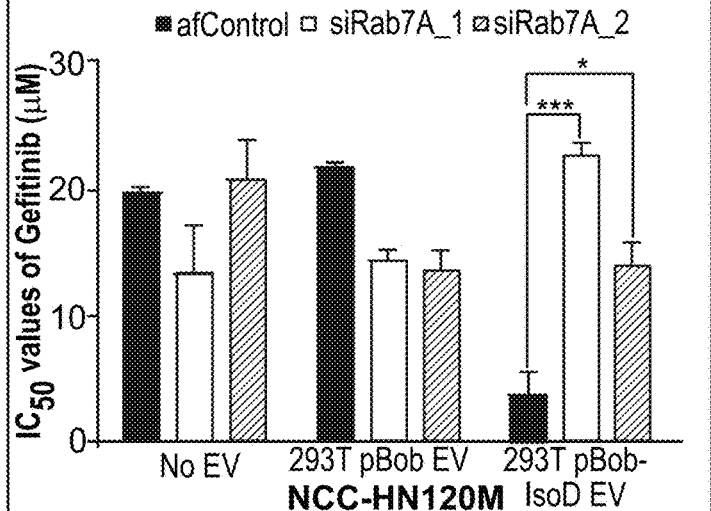
Figure 20A:
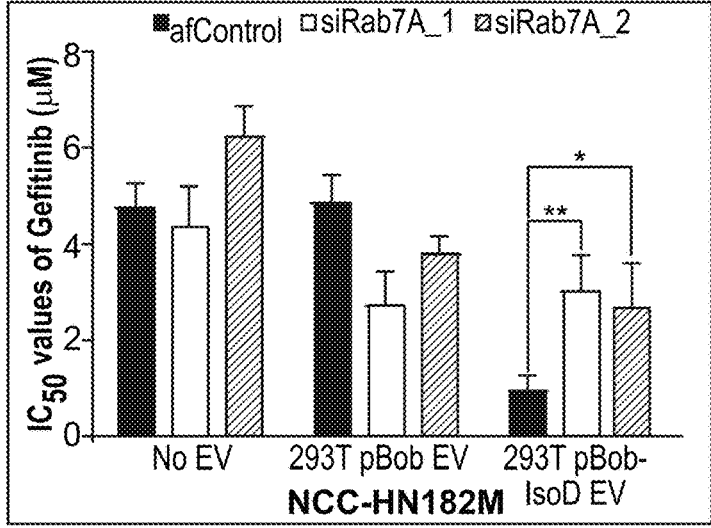
Figure 20A:
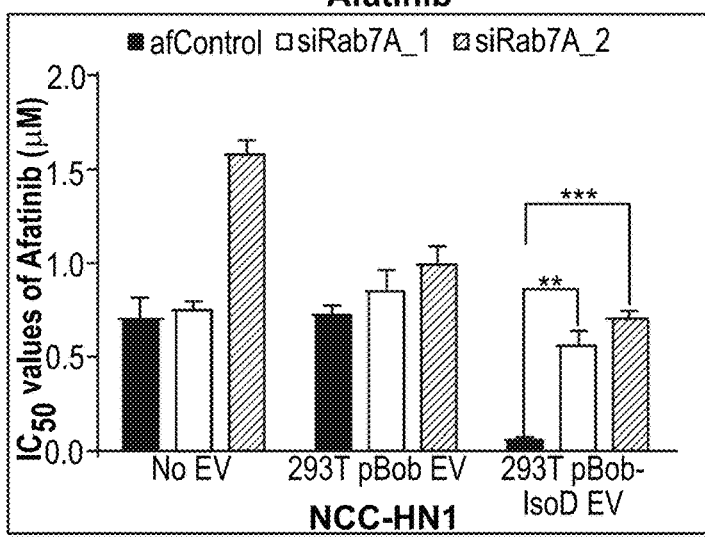
Figure 20A:
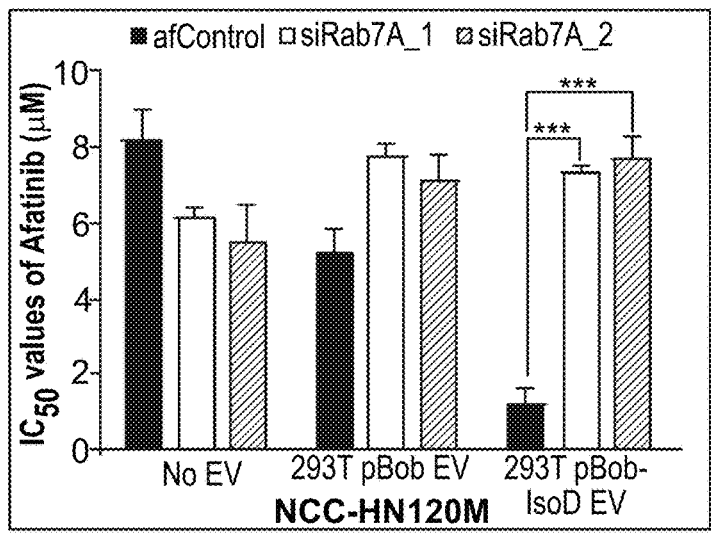
Figure 20A:
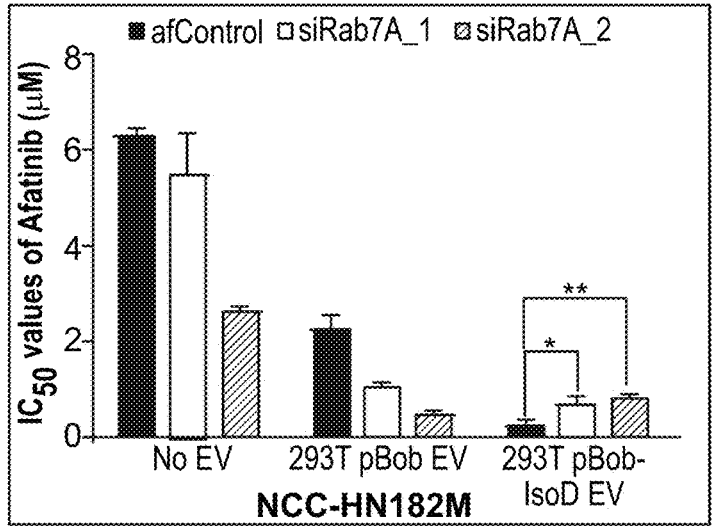
Figure 20A:
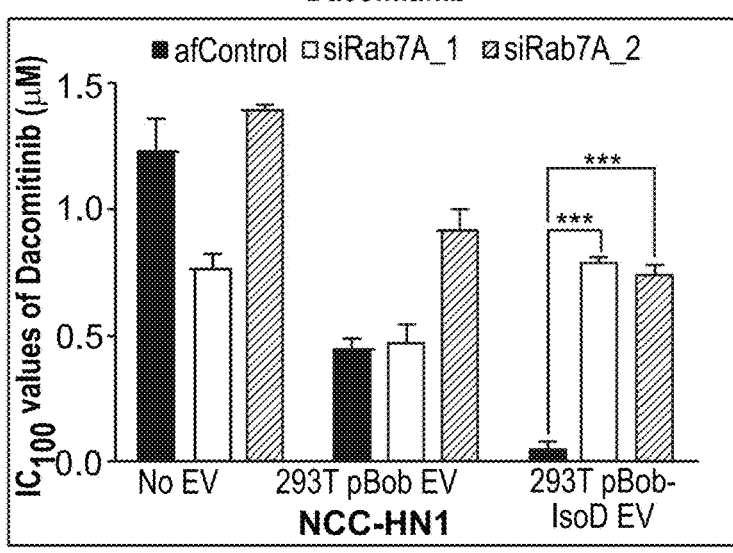
Figure 20A:
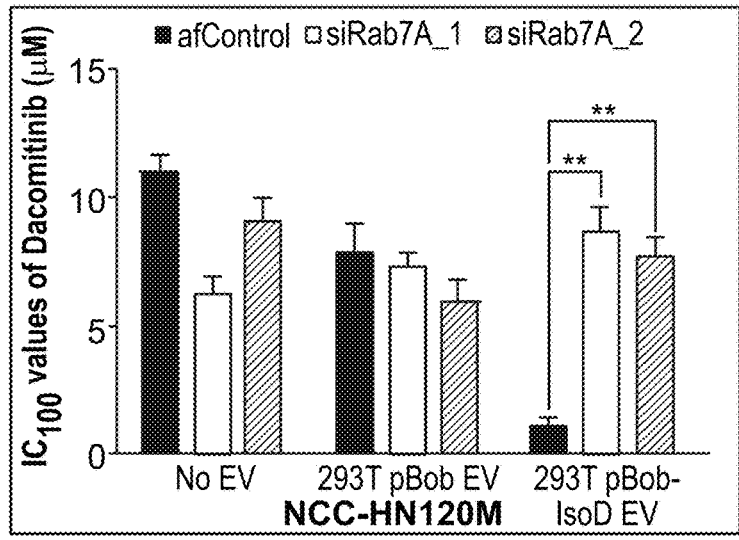
Figure 20A:
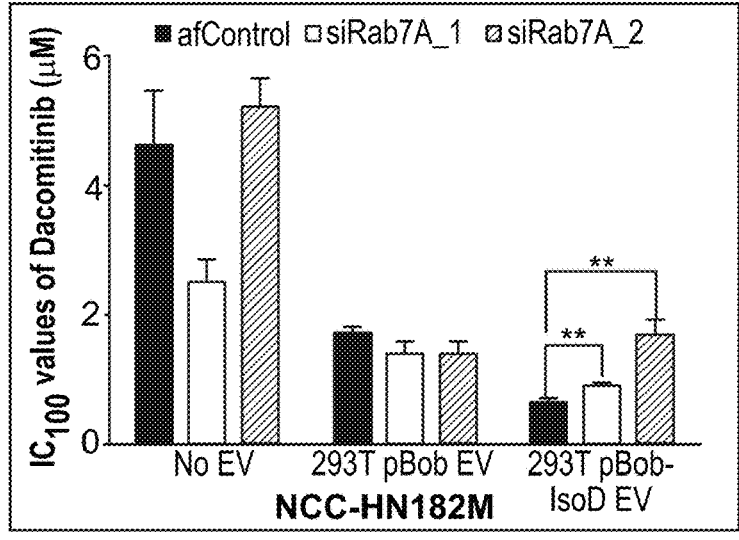
Figure 20B:
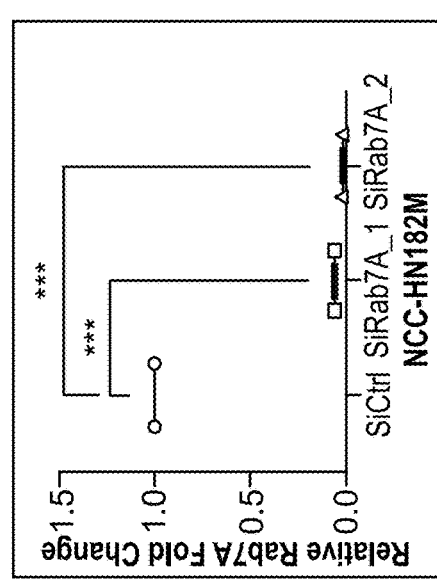
FIG. 20B shows the relative mRNA levels of Rab7A after transfection. Asterisks denote significance by student t-test: *p<0.05, p<0.01, *p<0.001, ****p<0.0001.
Figure 20B:
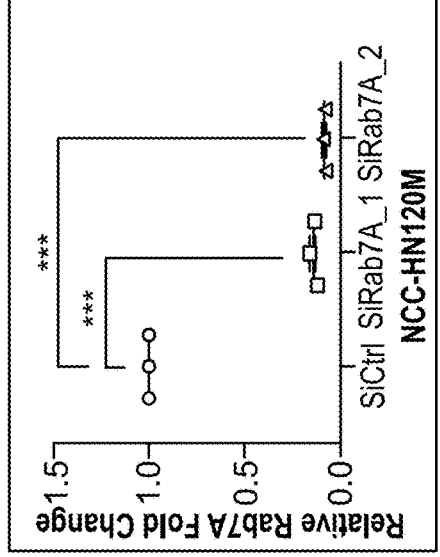
Figure 20B:
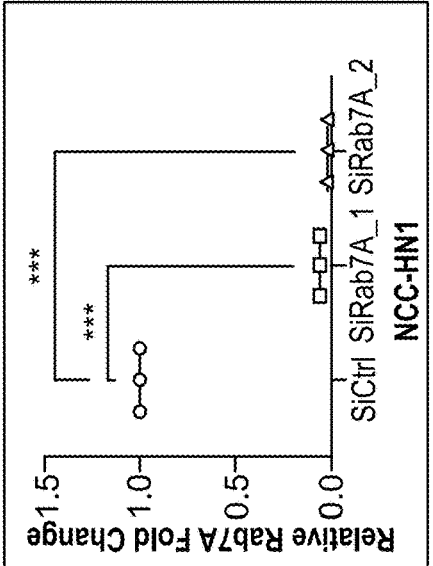

Secondly, Rab7A in HN1, HN120M, and HN182M cells was knocked down, and the cells were subsequently co-treated with HEK293T over-expressing EGFR isoform D extracellular vesicles. Like with siRab5A, a decreased sensitization conferred by Isoform D expressing EV was observed compared to a control (FIG. 20A). FIG. 20B shows the relative mRNA of siRab7A knockdown.

Figure 21A:
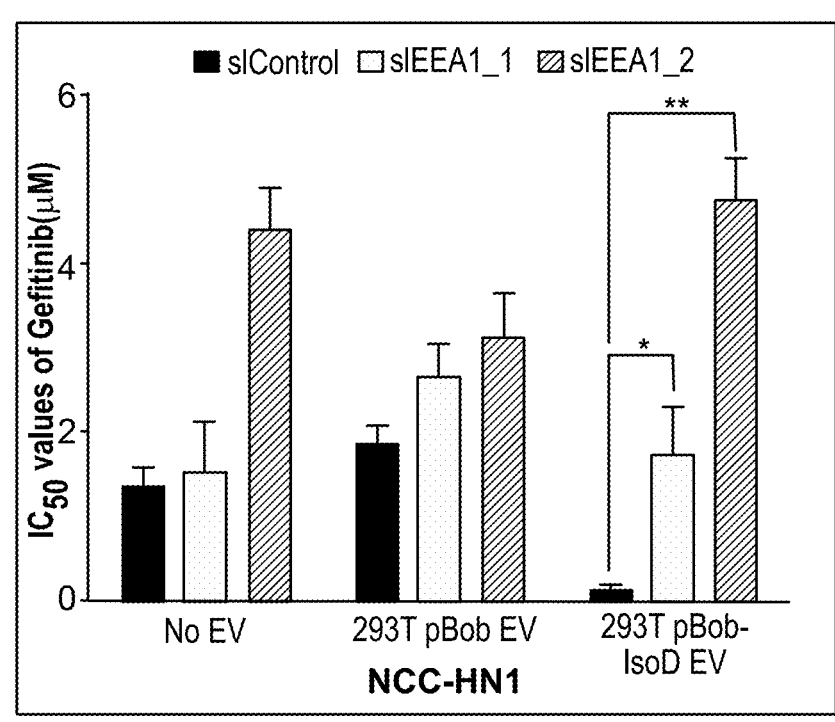
FIG. 21A shows the $IC_{50}$ values of NCC-HN1 and NCC-HN182M transfected with siRNA control (siCtrl), siEEA1 strand #1 (siEEA_1) or siEEA1 strand #2 (siEEA_2) and co-treated with gefitinib, afatinib, or dacomitinib, in the absence (no EV) or presence of EV from HEK293T over-expressing vector (pBob) or EGFR isoform D (pBob-Isoform D).
Figure 21A:
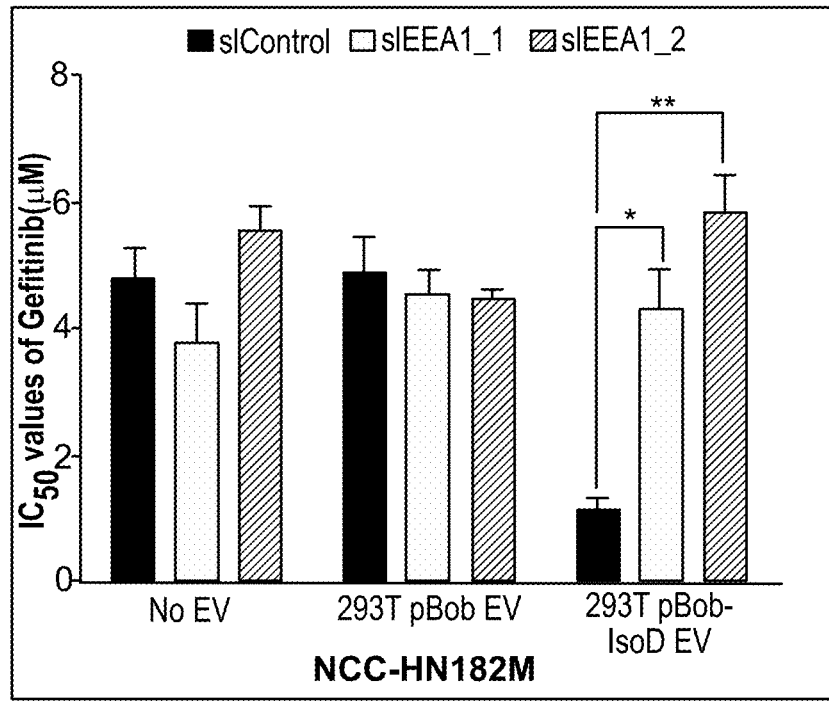
Figure 21A:
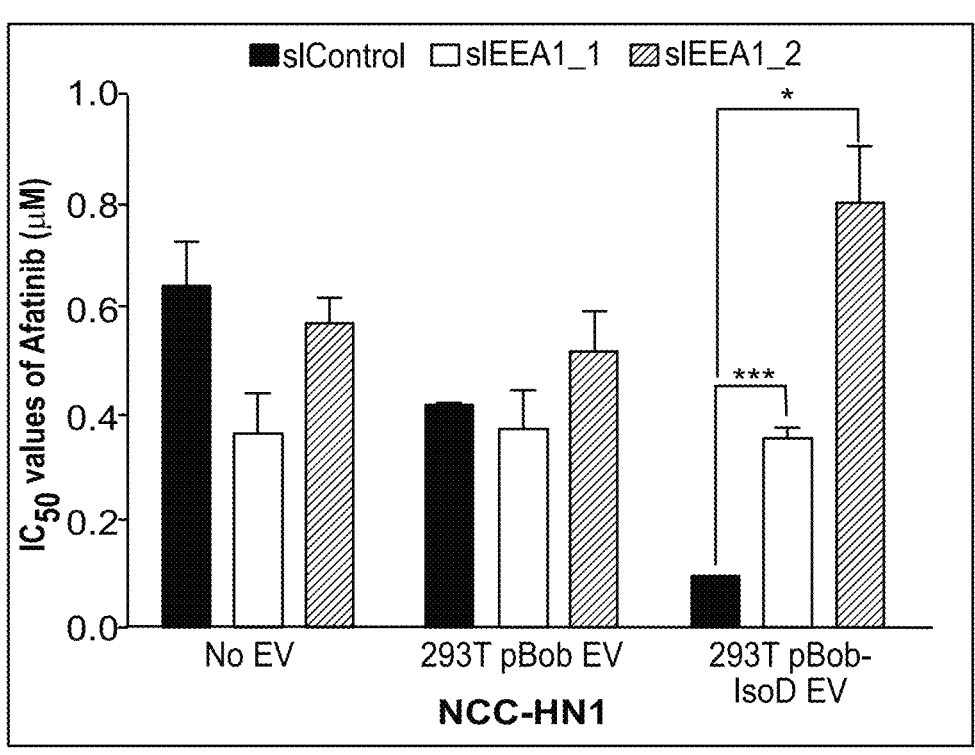
Figure 21A:
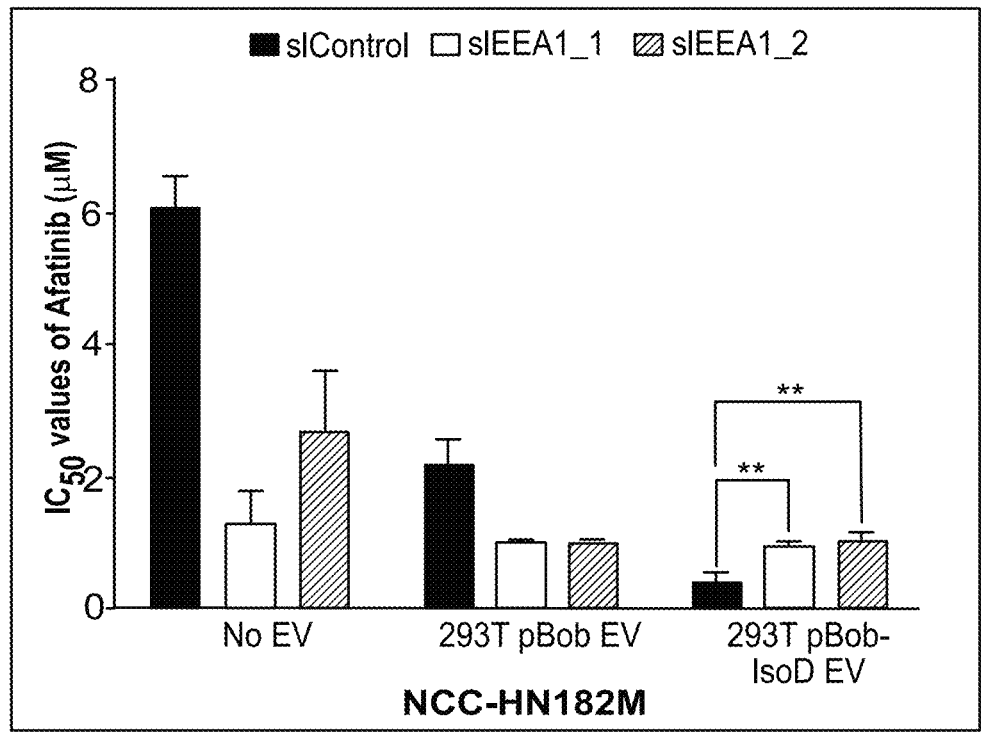
Figure 21A:
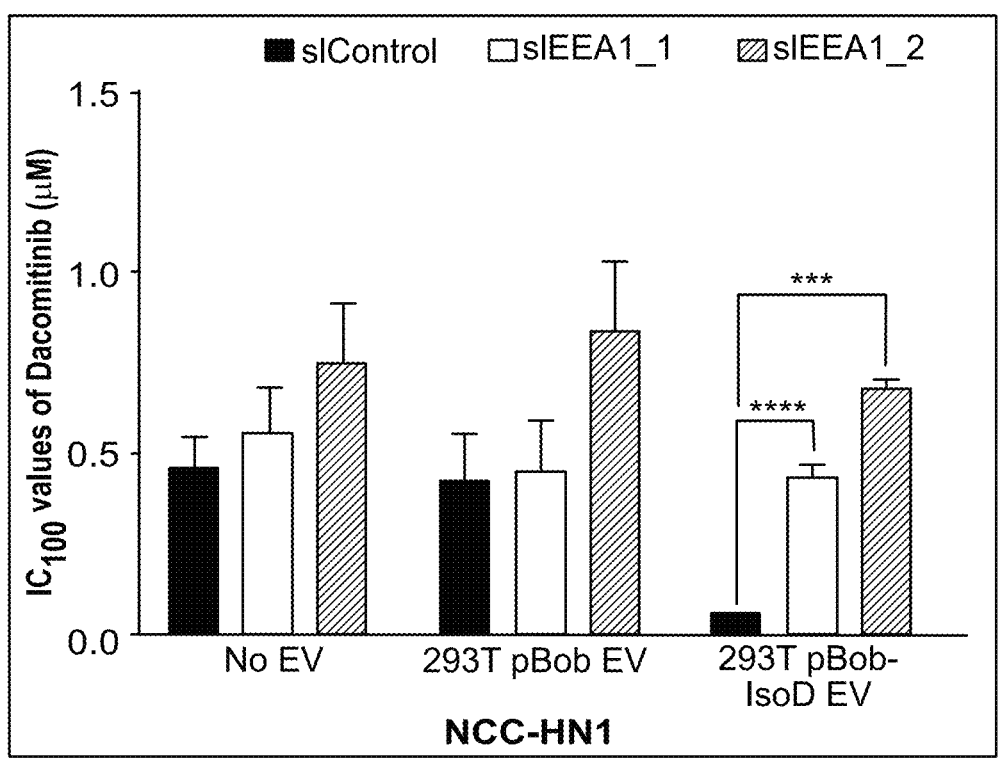
Figure 21A:
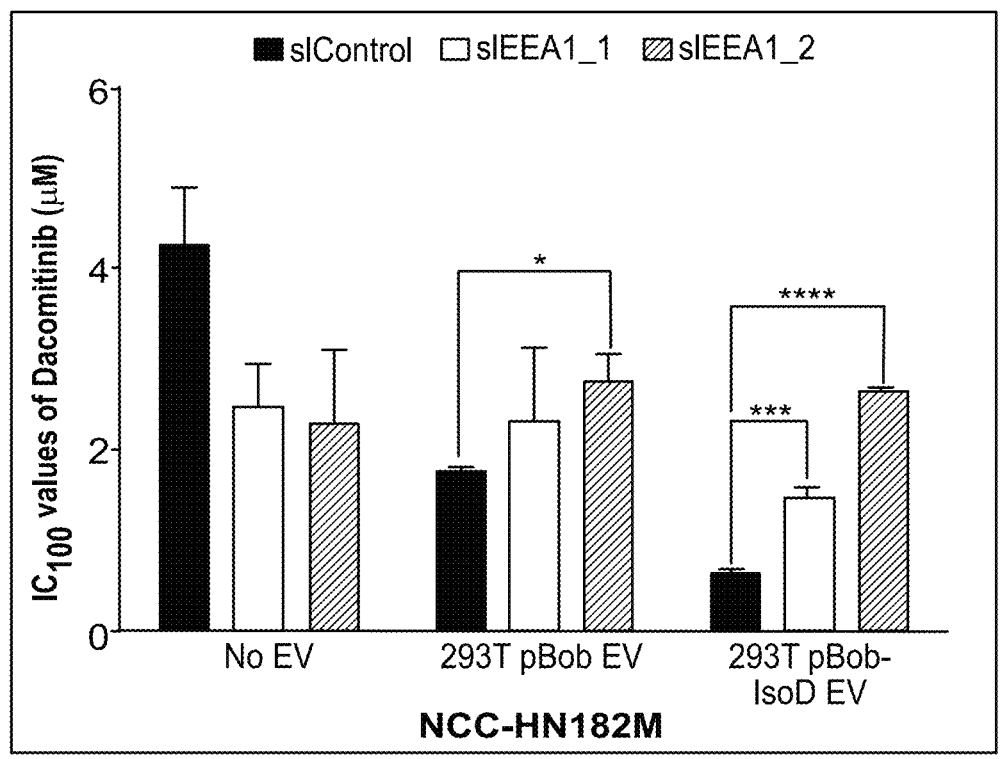
Figure 21B:
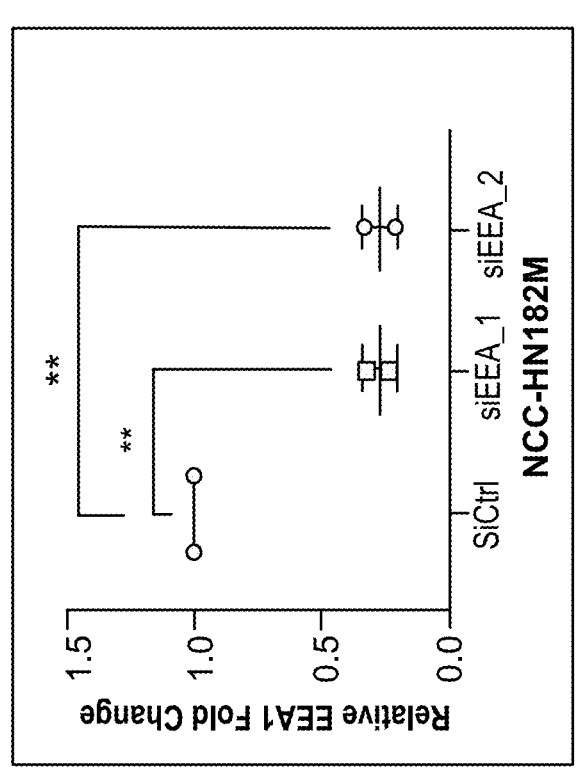
FIG. 21B shows the relative mRNA levels of EEA1 after transfection. Asterisks denote significance by student t-test: *p<0.05, p<0.01, *p<0.001, **p<0.0001. Taken together.
Figure 21B:
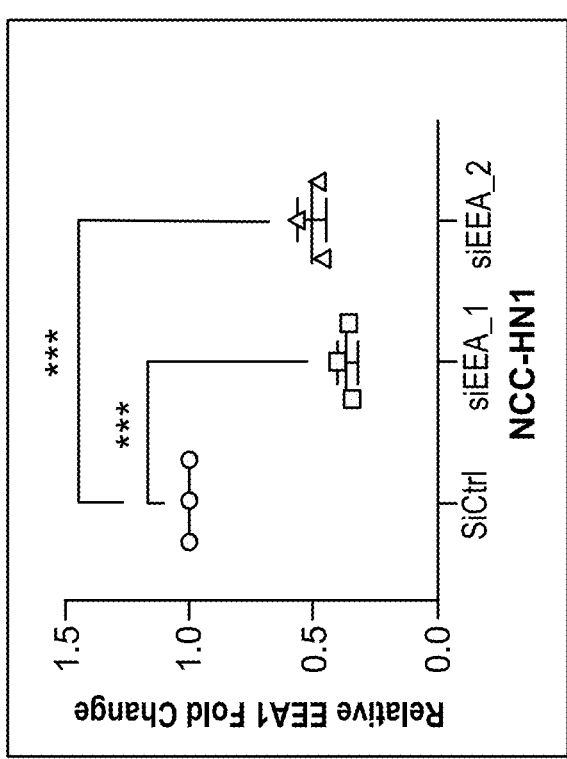

Finally, EEA1 was knocked down in HN1 and HN182M cells, and these cells were subsequently co-treated with HEK293T over-expressing EGFR isoform D extracellular vesicles. Consistent with the above, a decrease in sensitization conferred by EGFR isoform D extracellular vesicles compared to a control (FIG. 21A). FIG. 21B shows the relative mRNA of siEEA1 knockdown.

Figure 22:
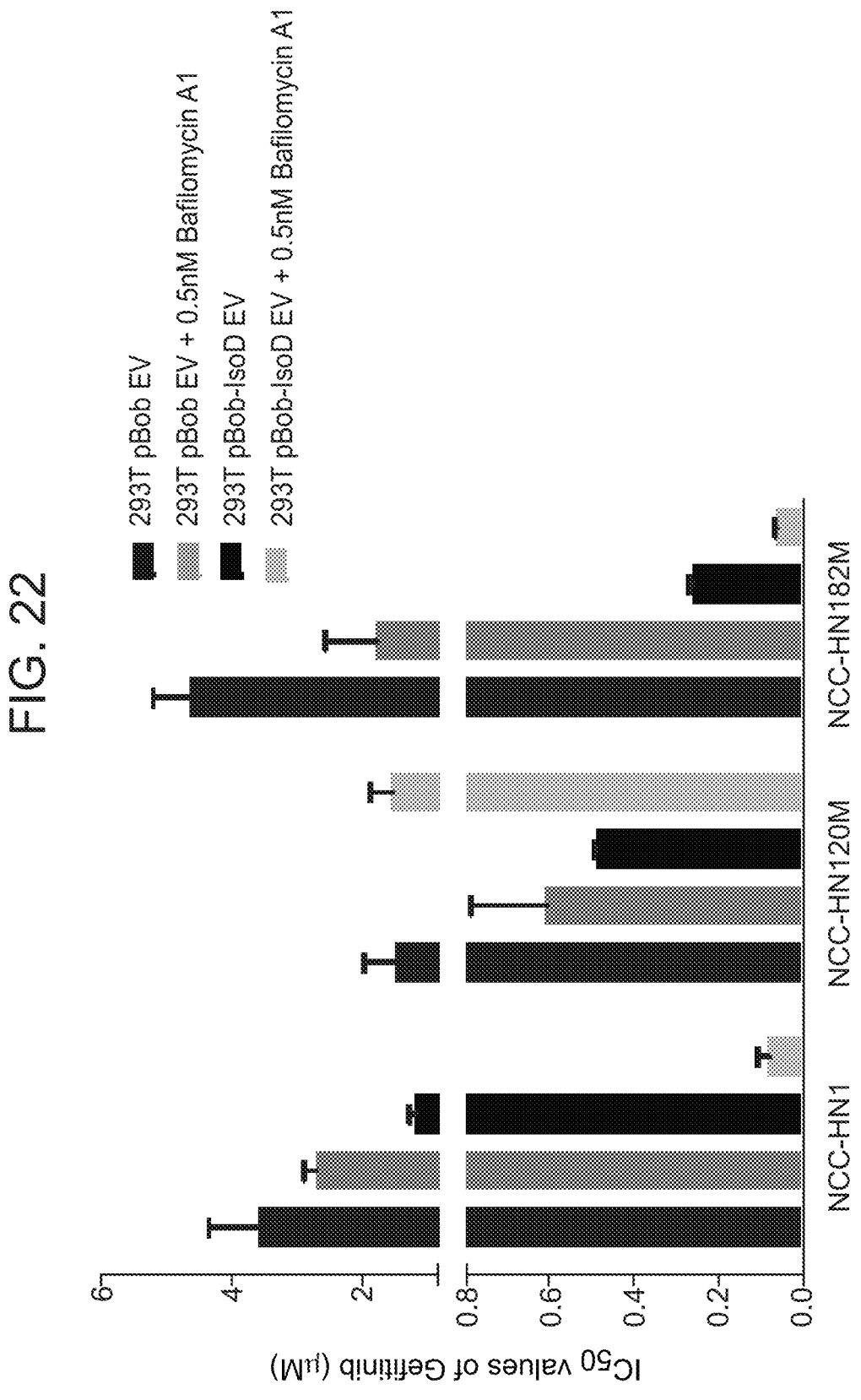
FIG. 22 shows $IC_{50}$ values of NCC-HN1, NCC-HN120M and NCC-HN182M treated with gefitinib in the absence or presence of 0.5 nM bafilomycin A1 and co-treated with EV from HEK293T over-expressing either vector control (pBob) or isoform D (pBob-IsoD) were obtained. This data shows that lysosomal inhibition increases the sensitizing effect of EGFR isoform D exosomes (EV) on the cells when co-treated with gefitinib.

The data from FIGS. 20, 21 and 22, when taken together, indicate the necessity of retrograde transport of the extracellular vesicles into the cellular compartment, in order for EGFR isoform D extracellular vesicles to confer their sensitising effect on the cell.

To elucidate the role played by the lysosome, a compartment downstream to the endosomes, in mediating the sensitivity of EGFR isoform D extracellular vesicle co-treatment, the lysosomal compartment was disrupted using an inhibitor, bafilomycin. The endocytic recycling processes were further disrupted by knocking down siRab1A, which is important for the anterograde transport of cargo from endocytic compartments to the cellular surface.

Earlier in this application, it had been shown that lysosomal inhibition by bafilomycin, when co-applied with EGFR isoform D extracellular vesicles increased the sensitivity of HN1 to gefitinib. Here, a similar observation is made with another cell line, HN182M (FIG. 22).

Figure 23:
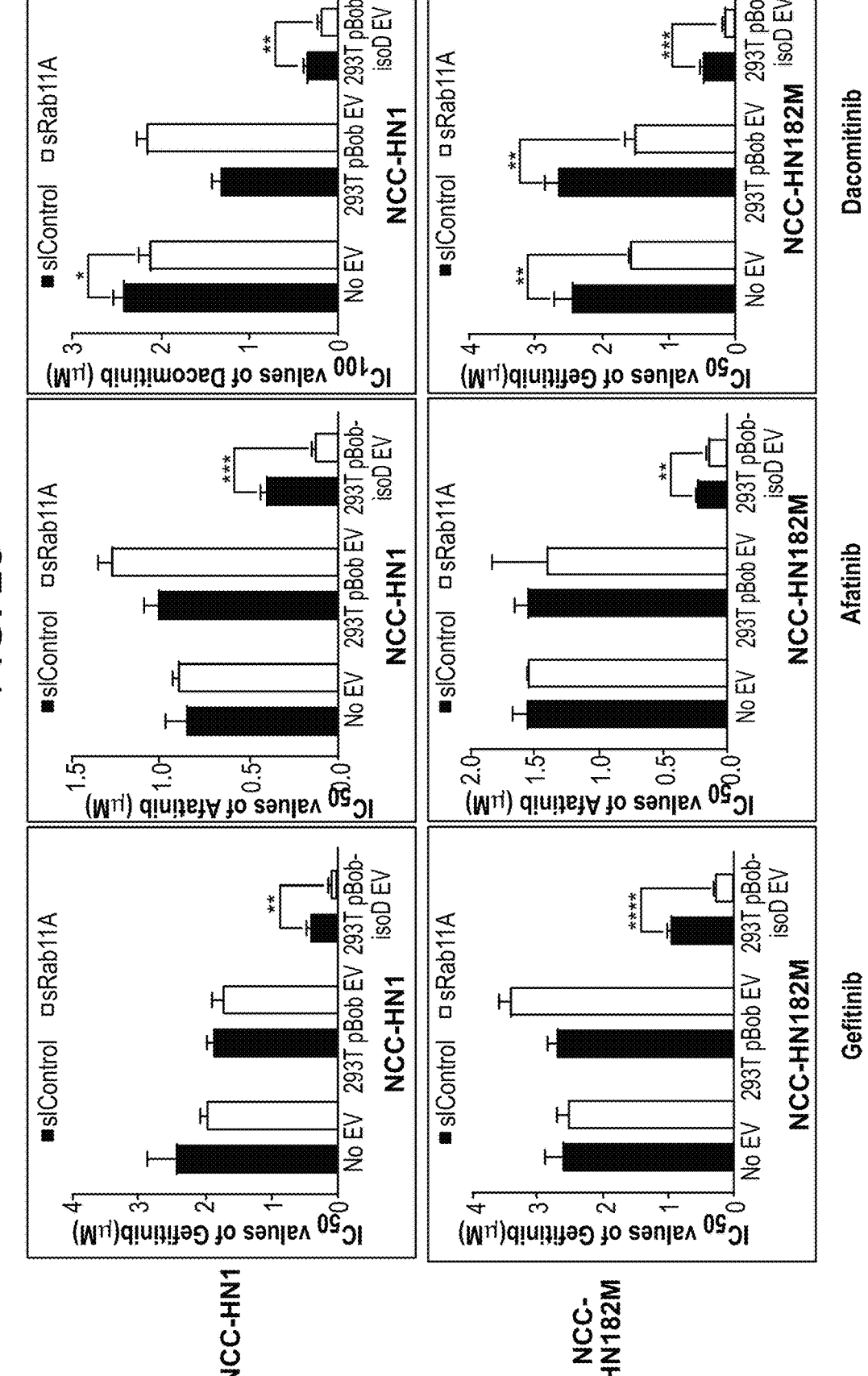
FIG. 23 shows data indicating that a knock-down of Rab11A in target cells increases the sensitizing effect conferred by EGFR isoform D exosomes (EV). The $IC_{50}$ values of NCC-HN1 and NCC-HN182M transfected with siRNA control (siControl) or siRab11A and co-treated with gefitinib, afatinib, or dacomitinib, in the absence (no EV) or presence of EV from HEK293T over-expressing vector (pBob) or Isoform D (pBob-Isoform D) are shown. This data shows that disrupting the recycling of endosomes to the cell surface increases EGFR isoform D EV sensitizing effect. Without being bound by theory, this is thought to be due to the retention of EGFR isoform D EV in endosomal compartments.

When the recycling process was disrupted with siRab11A, EGFR isoform D extracellular vesicle treated cells showed increased sensitivity to gefitinib, afatinib, and dacomitinib (FIG. 23).

Figure 25:
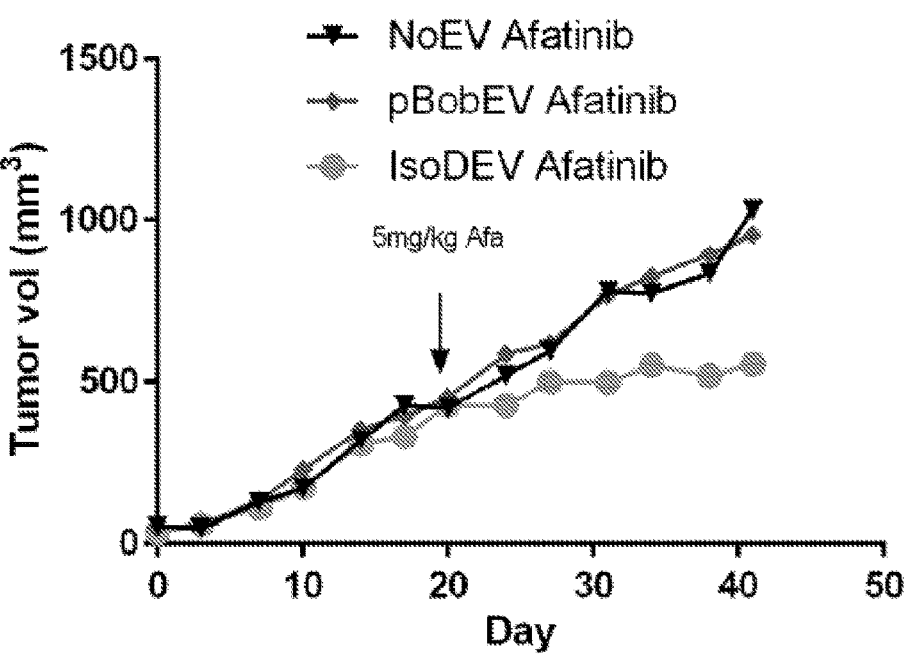
FIG. 25 shows a line graph indicating a reduced tumour burden of HNSCC xenograft when co-treated with EGFR isoform D exosomes (EV) and afatinib. Bulb/c Nude mice subcutaneously implanted with NCC-HN120M were started on a daily oral dose of 5 mg/kg afatinib and a 72-hour interval regime of peri-tumoral injection of EV from HEK293T over-expressing vector (pBobEV) or EGFR isoform D (IsoDEV). This demonstrates that the tyrosine kinase inhibitor-sensitisation effect of EGFR isoform D-containing EV can be replicated in an in vivo patient-derived xenograft model.
Figure 26:
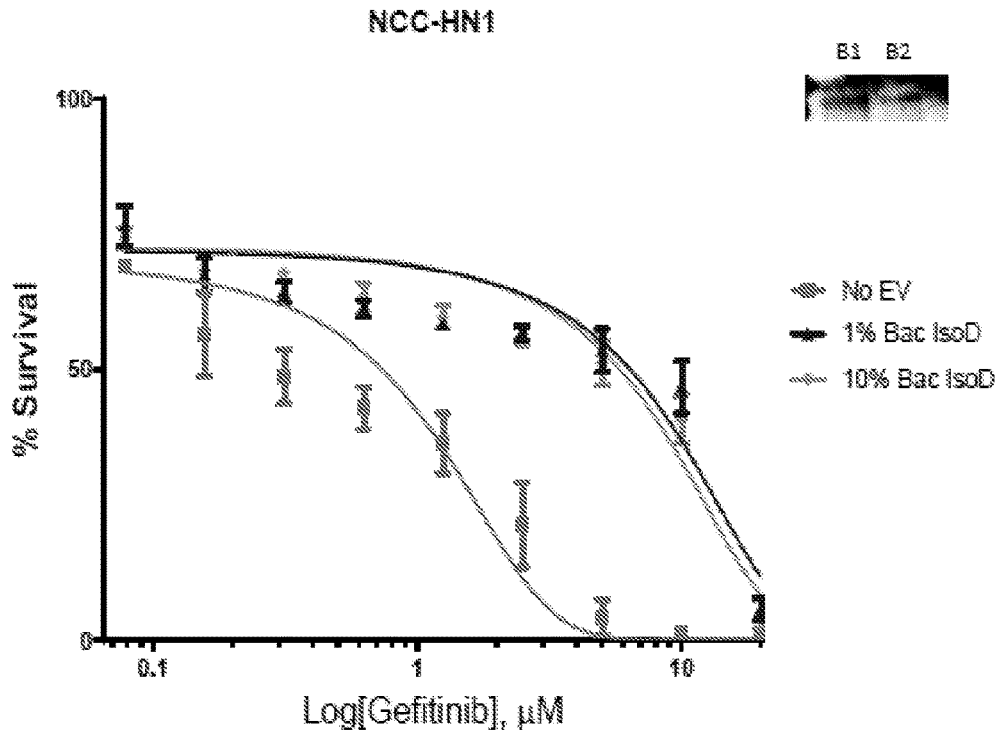
FIG. 26 shows data indicating that purified EGFR isoform D protein alone does not sensitize cells to gefitinib. Results are shown of a viability assay of NCC-HN1 cells when co-treated with gefitinib and human EGFR isoform D protein that had been produced in, and purified from, bacteria (A) or in mammalian HEK293F cells (B). Exosomes (EV) from HEK293T over-expressing Isoform D (10% 293T pBob-IsoDEV) were used as a control (B). This confirms that EGFR isoform D protein alone (that is to say, EGFR protein which is not asoociated with an EV) is unable to sensitise cells to tyrosine kinase inhibitors (TKIs), regardless of whether the protein is produce in a bacterial or mammalian system.
Figure 26:
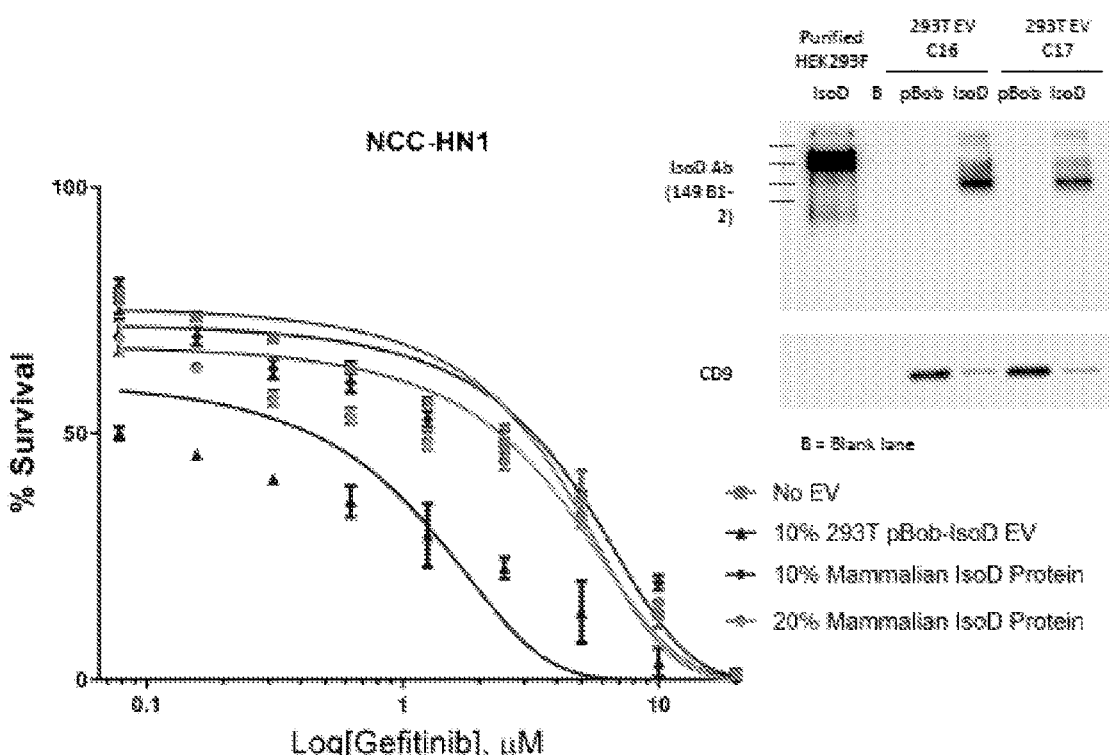
Figure 27:
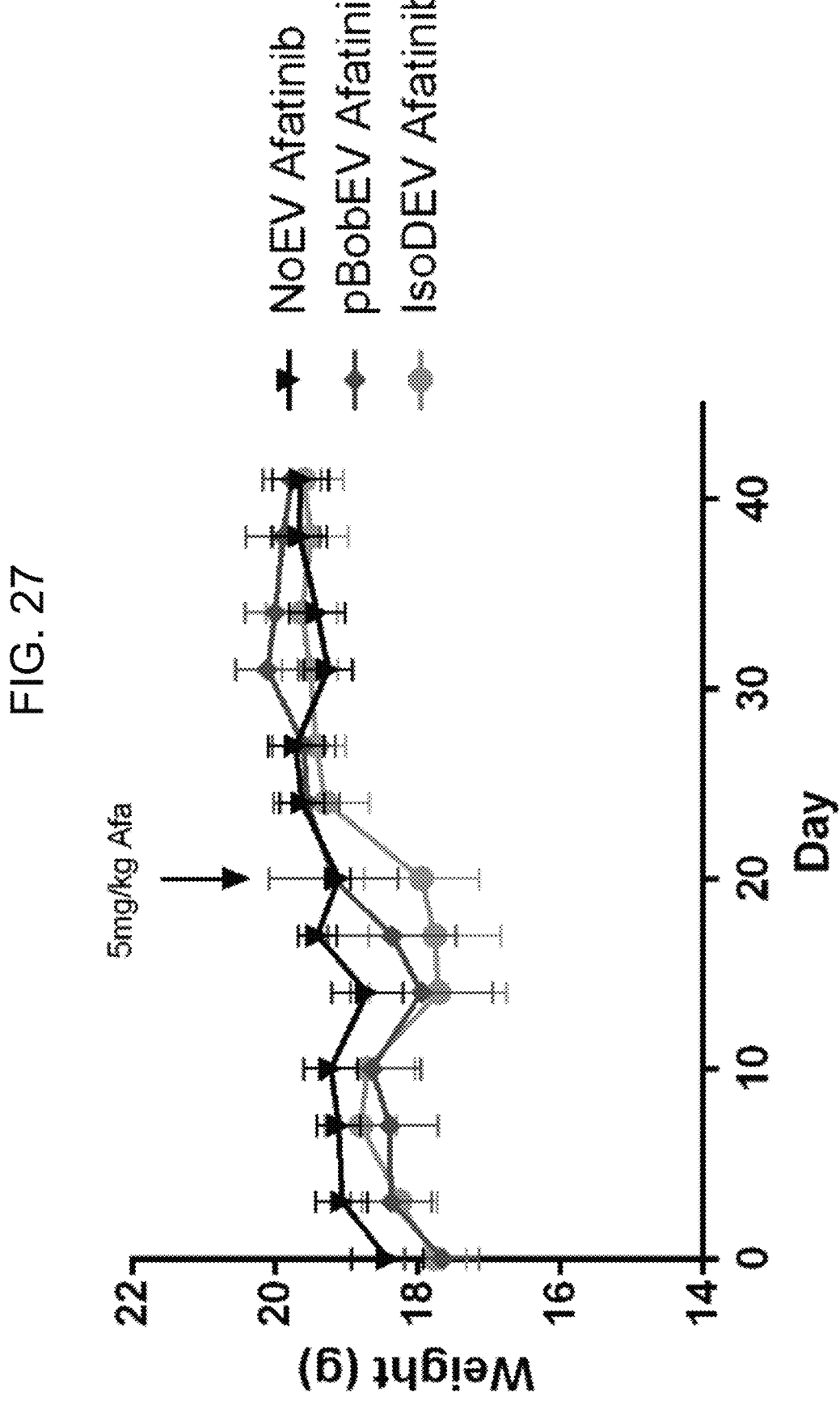
FIG. 27 shows data indicating that after afatinib and extracellular vesicle co-treatment, no changes in mouse body weight was observed. Arrow indicates commencement of daily oral afatinib administration with 72-hourly peri-tumoural extracellular vesicle (EV) injection. This confirms that the therapy delivered to the mice in FIG. 25 had minimal side effects/toxicity during the course of the experiment.

The data from FIGS. 25 and 26 indicate that the retention of EGFR isoform D extracellular vesicles within the intracellular compartments of target cells increases the sensitizing effect.

Figure 24A:
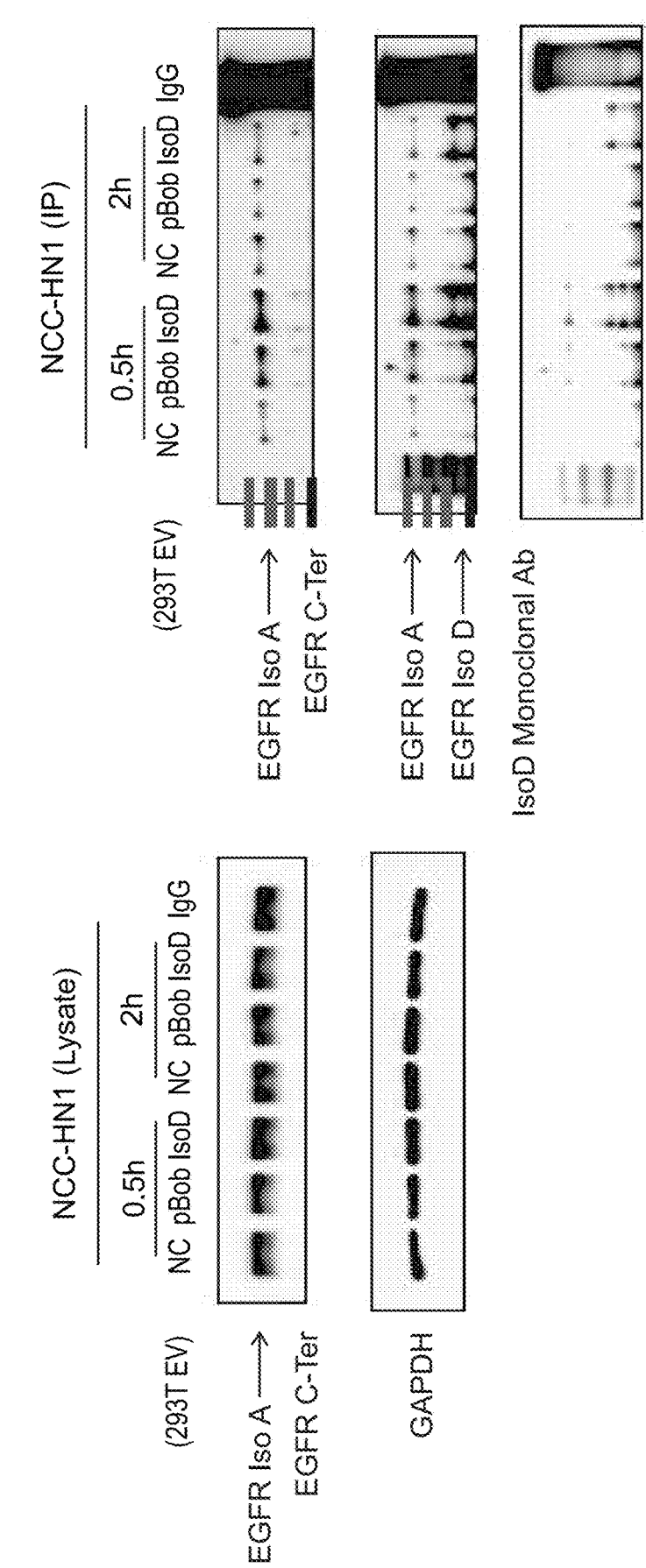
Figure 24B:
FIG. 24B shows the results of using EGFR isoform A antibody for precipitation, in NCC-HN1 cells treated with EV from HEK293T over-expressing vector (pBob) or Isoform D (IsoD). NC: Non-treated negative control. Without being bound by theory, it is thought that EGFR isoform A is a likely binding partner for EGFR isoform D on the cell surface.

To understand the downstream target of EGFR isoform D extracellular vesicles and given presence of a conserved N-terminal domain between EGFR isoform D and EGFR isoform A, an immunoprecipitation assay was performed to address ascertain whether these two proteins interacted. FIG. 24A shows the results of a pull-down of EGFR isoform A by EGFR isoform D in 30 minutes. When the reverse pull-down (FIG. 24B) was performed, the concentration of EGFR isoform D was increased when using EGFR isoform A protein to pull down. This data indicates that EGFR isoform A and EGFR isoform D interacted with each other.

To address the therapeutic effects of EGFR isoform D in an in vivo setting, a xenograft model in Bulb/c nude mice was generated by implanting HN120M subcutaneously. The data of FIG. 25 shows that the co-administration of afatinib with EGFR isoform D reduced the tumour growth rate compared to control.

Additionally, the necessity and effect of extracellular vesicle packaging on the effectiveness of EGFR isoform D to confer its sensitizing effect was ascertained. EGFR isoform D protein alone was produced and introduced to cancer cells. FIG. 26 shows that the EGFR isoform D protein produced in bacteria or mammalian cells, HEK293F, failed to confer its sensitizing effect. This data indicated that packaging into extracellular vesicles or exosomes is required for EGFR isoform D to confer its sensitizing effect.

The data provided herein highlights the use and application of exosomal epidermal growth factor receptor (EGFR) Isoform D as an agent that increases a cell's sensitivity to EGFR tyrosine kinase inhibitors (TKI), thereby confirming its use as a drug or a co-drug. It was also shown through knockdown and over-expression studies that the presence of EGFR Isoform D in the form of extracellular vesicles (EV) or exosomes is necessary and sufficient to confer an increased sensitivity of the cell to various EGFR TKIs. In one example, it was also shown that extracellular vesicles (EVs) from HEK293T cells over-expressing Isoform D can sensitize head and neck small cell carcinoma (HNSCC) cells to a panel of eight tyrosine kinase inhibitors. It was further demonstrated that an increasing amount of extracellular vesicles (EV) or exosomes containing EGFR isoform D enhances the sensitizing effect of the extracellular vesicles (EV) or exosomes in a dose-dependent manner. Finally, the necessity of endocytosis in conferring the Isoform D sensitizing effect was shown using PitStop 2, a clathrin-mediated endocytosis inhibitor.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Apart from HEK 293T cells, the experiments disclosed herein were performed using exosomes applied to unmodified patient-derived tumour cultures or cell lines. The identities of these patient-derived tumour cultures or cell lines have been validated by matching them to individual patient's tumour from whom they were derived, thereby, confirming their provenance (Chia et al., 2017). These cell lines are not commercial, immortalized, nor modified.
Extracellular Vesicles (EVs)

Extracellular vesicle (EV) collection and isolation were carried out as previously described*. Briefly, cells were grown in T-175 tissue culture flasks with conditioning medium (NCM). After 72 hours incubation, the NCM was collected and spun down at 1,200 rpm for 10 minutes to remove cell debris. The supernatant was then filtered through a 0.22 um filter (PES) and the filtrate was loaded into Amicon® Ultra-15 Centrifugal Filter Unit (Merck Millipore, Kenilworth, NJ). The medium was concentrated and subjected to a final wash with 1×PBS before reconstituting to 1/60 of the original volume. To reduce extracellular vesicle batch variation, every five extracellular vesicle batches were pooled into a single batch for analysis and treatment.
*Reference: Rodrigues-Junior, D. M. et al. Circulating extracellular vesicle-associated TGFβ3 modulates response to cytotoxic therapy in head and neck squamous cell carcinoma. Carcinogenesis 1-13 (2019). doi:10.1093/carcin/bgz148
Cell Proliferation Assay and Determination of $IC_{50}$ Values Cells were seeded in 100 μl complete growth medium at a density of 1,000-3,000 cells/well in 96-well tissue culture plates. Cells were washed with 1×PBS to remove remaining medium residue prior treatment. After serial dilutions of EGFR tyrosine kinase inhibitors (TKIs) in complete growth medium, respective proportions of extracellular vesicle-containing medium were added to the cells as co-treatment. EGFR tyrosine kinase inhibitors (TKIs) used are gefitinib, erlotinib, afatinib, lapatinib, dacomitinib, nazartinib, WZ4002 or osimertinib (Selleck Chemicals, Houston, TX), while dimethyl sulfoxide (DMSO) was used as controls. Plates were incubated for 72 hours at 37° C. after which cell viability was assessed using CellTitre-Glo® Luminescent Assay according to the manufacturer's protocol (Promega, Madison, WI).
RNA Analysis Total mRNA was extracted using Qiagen RNeasy Mini Kit (Qiagen, Valencia, CA) as per manufacturer's instruction. mRNA was converted to cDNA using SuperScript II (Thermo Fisher Scientific, Waltham, MA) as per manufacturer's instruction and quantified using iTaq Universal SYBR Green Supermix (Bio-Rad Laboratories, Hercules, CA) real-time PCR reagents according to manufacturer's instructions. Reactions were carried out in triplicate with TBP served as the normalizing control as previously described.
Protein Analysis For Western blot analysis, cell pellet or extracellular vesicle (EV) samples were lysed in RIPA buffer (1% Triton X-100, 0.5% sodium deoxycholate, 0.1% SDS, 1×PBS), clarified by centrifugation at 14,000 g for 30 minutes and proteins were quantitated by Pierce BCA Protein Assay kit (Thermo Fisher Scientific, Waltham, MA) according to manufacturer's instructions. Equal amounts of proteins were loaded into each lane in the SDS-PAGE gel (Bio-Rad Laboratories, Hercules, CA). Antibodies used were as previously described*, with the addition of CD9 (#13174, Cell Signaling, Danvers, MA), EpCAM (#2626, Cell Signaling) and ALIX (#2171, Cell Signaling).
shRNA Knockdown and RNA Transfection shRNA lentivirus particles containing plasmids pLKO.1 vector, pLKO.1-shIsoD_A: TTGCTGAGTGAAT-GAACAAAT (SEQ ID NO: 1), pLKO.1-shIsoD_B: AGCCAGCTGTGGGACAATTAT (SEQ ID NO: 2) and pLKO.1-shIsoD_C: GCCAGCCTTCTCCGTAATTAG (SEQ ID NO: 3) were purchase from Sigma (St. Louis, MO). EGFR isoform D knockdown cells shIsoD_1 were generated by infection with pLKO.1-shIsoD_A particles; and shIsoD_2 cells were generated by co-infection with pLKO.1-shIsoD_B and pLKO.1-shIsoD_C particles according to manufacturer's instruction.
Overexpression of EGFR Isoform D EGFR isoform D open reading frame (NM_201284) was PCR cloned into NheI and XhoI site of the modified pCSC-SP-PW (aka:pBOB, Addgene) with primers GGATC-CATGGCTAGCATGCGACCCTCCGGGACG (SEQ ID NO: 4) and CCTGCAGCTGCTCGAGTCAGTGGCAG-GAGGAGGCC (SEQ ID NO: 5). The construct was cotransfected into HEK 293T cells with ViraPower Lentiviral expression systems (Invitrogen) as per manufacturer instruction, to produce lentiviral particles. NCC-HN1 and HEK 293T were transduced as per manufacturer's instruction and stable cells were selected using 0.2 ug/ml zeocin.

Bacterial EGFR Isoform D Production

EGFR isoform D open reading frame (NM_201284) was PCR cloned into NdeI and XhoI site of pet15b (Merck) with primers CGCGCGGCAGCCATAT-GATGCGACCCTCCGGGACG (SEQ ID NO: 6) and CAGCCGGATCCTCGAGTCAGTGGCAGGAG-GAGGCC (SEQ ID NO: 7). The construct was transformed into BL21DE3 cell (Invitrogen) as per manufacturer instruction. EGFR isoform D protein was induced with 1 uM IPTG and harvested with lysis buffer (50 mM Tris.HCl pH7.4, 150 mM NaCl, 5 mM βME, 0.1% Triton X-100, 10% Glycerol). Bacterial lysate containing EGFR isoform D was affinity purified with HisPur Ni-NTA Chromatography Cartridges (ThermoFisher) with sequential wash with buffer A (50 mM Tris.HCl pH7.4, 150 mM NaCl, 5 mM βME, 0.1% Triton X-100, 10% Glycerol, 10 mM Imidazole), buffer B (50 mM Tris.HCl pH7.4, 1M NaCl, 5 mM βME, 0.1% Triton X-100, 10% Glycerol) and buffer A again. EGFR isoform D protein was eluted in elution buffer (50 mM Tris.HCl pH7.4, 150 mM NaCl, 5 mM βME, 0.1% Triton X-100, 10% Glycerol, 250 mM Imidazole). Western blot verified EGFR isoform D fractions were pooled and desalted with Amicon® Ultra-15 Centrifugal Filter Unit (Merck Millipore, Kenilworth, NJ).

Proteinase K Digestion

70 μg of isolated exosome was subjected to 1 μg/ml proteinase K treatment at 37° C. for the indicated time (see FIG. 13) in the presence or absence of 1% v/v Triton X-100. Upon the expiry of the indicated time, 2× Laemmli loading buffer (Bio-rad) was added to stop the proteinase K activity. Samples were subsequently analysed by western blotting.

The invention claimed is:

1. A method of increasing sensitivity of an EGFR-related cancer to epidermal growth factor receptor (EGFR) tyrosine kinase inhibitor (TKI) comprising administering a therapeutically effective amount of epidermal growth factor receptor isoform D to a subject in need thereof, wherein the epidermal growth factor receptor isoform D is exosomal epidermal growth factor receptor isoform D.

2. The method of claim 1 further comprising administration of a TKI.

3. The method of claim 1, wherein the epidermal growth factor receptor isoform D is provided as one or more of the following: exosomal formulations, liposomal formulations, nanocarriers and nanoparticles.

4. A method of treating a subject suffering from an EGFR-related cancer, comprising:

administering to the subject an effective amount of epidermal growth factor receptor isoform D; and administering to the subject an effective amount of a tyrosine kinase inhibitor used to treat the EGFR-related cancer, wherein the epidermal growth factor receptor isoform D is exosomal epidermal growth factor receptor isoform D.

5. The method of claim 4, wherein the epidermal growth factor receptor isoform D is provided as one or more of the following: exosomal formulations, liposomal formulations, nanocarriers and nanoparticles.

6. The method of claim 4, wherein the tyrosine kinase inhibitor is administered separately, before, after, or in combination with, the epidermal growth factor receptor isoform D.

7. The method of claim 4, wherein the tyrosine kinase inhibitor is an EGFR inhibitor.

8. The method of any one of claim 4, wherein the tyrosine kinase inhibitor is selected from the group consisting of gefitinib, erlotinib, erlotinib HCl, lapatinib, dacomitinib, TAE684, afatinib, dasatinib, saracatinib, veratinib, AEE788, WZ4002, icotinib, osimertinib, BI1482694, ASP8273, EGF816, AZD3759, nazartinib, and combinations thereof.

9. The method of claim 8, wherein the tyrosine kinase inhibitor is selected from the group consisting of gefitinib, erlotinib and lapatinib, and combinations thereof; or wherein the tyrosine kinase inhibitor is selected from the group consisting of gefitinib, afatinib and dacomitinib, and combinations thereof.

10. The method of claim 4, wherein the EGFR-related cancer selected from the group consisting of head and neck cancer, esophagus, bladder, cervix, skin cancer and lung cancer.

11. The method of claim 10, wherein the head and neck cancer is head and neck squamous cell carcinoma (HNSCC) or oral squamous cell carcinoma (OSCC).

12. The method of claim 10, wherein the lung cancer is non-small cell lung cancer (NSCLC).

13. The method of claim 10, wherein the skin cancer is squamous-cell skin cancer.

* * * * *

```
                      SEQUENCE LISTING

<160> NUMBER OF SEQ ID NOS: 7

<210> SEQ ID NO 1
<211> LENGTH: 21
<212> TYPE: DNA
<213> ORGANISM: Artificial sequence
<220> FEATURE:
<223> OTHER INFORMATION: pLKO.1-shIsoD_A

<400> SEQUENCE: 1
ttgctgagtg aatgaacaaa t                                            21

<210> SEQ ID NO 2
<211> LENGTH: 21
<212> TYPE: DNA
<213> ORGANISM: Artificial sequence
<220> FEATURE:
<223> OTHER INFORMATION: pLKO.1-shIsoD_B

<400> SEQUENCE: 2
agccagctgt gggacaatta t                                            21

<210> SEQ ID NO 3
<211> LENGTH: 21
<212> TYPE: DNA
<213> ORGANISM: Artificial sequence
<220> FEATURE:
<223> OTHER INFORMATION: pLKO.1-shIsoD_C

<400> SEQUENCE: 3
gccagccttc tccgtaatta g                                            21

<210> SEQ ID NO 4
<211> LENGTH: 34
<212> TYPE: DNA
<213> ORGANISM: Artificial sequence
<220> FEATURE:
<223> OTHER INFORMATION: EGFR isoform D open reading frame cloning
      primer 1, for cloning into modified pCSC-SP-PW

<400> SEQUENCE: 4
ggatccattg gctagcatgc gaccctccgg gacg                              34

<210> SEQ ID NO 5
<211> LENGTH: 35
<212> TYPE: DNA
<213> ORGANISM: Artificial sequence
```

-continued

```
<220> FEATURE:
<223> OTHER INFORMATION: EGFR isoform D open reading frame cloning
      primer 2, for cloning into modified pCSC-SP-PW

<400> SEQUENCE: 5
cctgcagctg ctcgagtcag tggcaggagg aggcc                              35

<210> SEQ ID NO 6
<211> LENGTH: 35
<212> TYPE: DNA
<213> ORGANISM: Artificial sequence
<220> FEATURE:
<223> OTHER INFORMATION: EGFR isoform D open reading frame cloning
      primer 1, for cloning into pet15b

<400> SEQUENCE: 6
cgcgcggcag ccatatgatg cgaccctccg ggacg                              35

<210> SEQ ID NO 7
<211> LENGTH: 35
<212> TYPE: DNA
<213> ORGANISM: Artificial sequence
<220> FEATURE:
<223> OTHER INFORMATION: EGFR isoform D open reading frame cloning
      primer 2, for cloning into pet15b

<400> SEQUENCE: 7
cagccggatc ctcgagtcag tggcaggagg aggcc                              35
```